(12) United States Patent
Nissim et al.

(10) Patent No.: US 9,844,602 B2
(45) Date of Patent: *Dec. 19, 2017

(54) ANTIBODY AND USE IN DIAGNOSIS AND THERAPY OF ARTHROPATHIES

(75) Inventors: Ahuva Nissim, London (GB); Yuti Chernajovsky, London (GB); Bjarne Faurholm, Cape Town (ZA); David Perrett, London (GB); Paul Winyard, Exeter (GB); Christopher Hughes, London (GB); Stephen Mather, London (GB); Francesco Dell'Accio, London (GB)

(73) Assignee: Queen Mary & Westfield College, London (GB)

( * ) Notice: Subject to any disclaimer, the term of this patent is extended or adjusted under 35 U.S.C. 154(b) by 1195 days.

This patent is subject to a terminal disclaimer.

(21) Appl. No.: 12/598,671

(22) PCT Filed: May 2, 2008

(86) PCT No.: PCT/GB2008/001526
§ 371 (c)(1),
(2), (4) Date: Feb. 11, 2010

(87) PCT Pub. No.: WO2008/135734
PCT Pub. Date: Nov. 13, 2008

(65) Prior Publication Data
US 2011/0129415 A1 Jun. 2, 2011

(30) Foreign Application Priority Data
May 3, 2007 (GB) .................................. 0708585.5

(51) Int. Cl.
A61K 47/48 (2006.01)
A61K 51/10 (2006.01)
C07K 16/18 (2006.01)

(52) U.S. Cl.
CPC .. *A61K 47/48538* (2013.01); *A61K 47/48415* (2013.01); *A61K 47/48423* (2013.01); *A61K 47/48438* (2013.01); *A61K 51/1096* (2013.01); *C07K 16/18* (2013.01); *C07K 2317/55* (2013.01); *C07K 2317/565* (2013.01); *C07K 2317/569* (2013.01); *C07K 2317/622* (2013.01); *C07K 2317/76* (2013.01)

(58) Field of Classification Search
None
See application file for complete search history.

(56) References Cited

U.S. PATENT DOCUMENTS 6,642,007 B1 11/2003 Saltarelli et al.

FOREIGN PATENT DOCUMENTS

| WO | 94/18563 A1 | 8/1994 |
|---|---|---|
| WO | 2007/017556 A1 | 2/2007 |
| WO | 2010/115745 A2 | 10/2010 |
| WO | 2012/156313 A1 | 11/2012 |

OTHER PUBLICATIONS

De Pascalis, R., et al. J. Immunol. 2002;169:3076-3084.*
Lamminmaki, U., et al. J. Biol. Chem. 2001;276(39):36687-36694.*
Johnson, G. and Wu, T.T. Nuc.Acid Res. 2000;28(1):214-218.*
Carroll, M. C., The role of complement and complement receptors in induction and regulation of immunity, Annu Rev Immunol. 1998;16:545-68.
Chernajovsky, Y., et al., Development of new molecules, vectors and cells for therapy of arthritis, Joint Bone Spine. Dec. 2003;70(6):474-6.
Cohen-Saidon, C., et al., A novel strategy using single-chain antibody to show the importance of Bcl-2 in mast cell survival, Blood. Oct. 1, 2003;102(7):2506-12.
Coombs, G. H., et al., Parasite proteinases and amino acid metabolism: possibilities for chemotherapeutic exploitation, Parasitology. 1997;114 Suppl:S61-80.
Dell'Accio, F. et al., Activation of WNT and BMP signaling in adult human articular cartilage following mechanical injury, Arthritis Res Ther. 2006;8(5):R139.
De Wildt, R. M. T., et al., Antibody arrays for high-throughput screening of antibody-antigen interactions, Nat Biotechnol. Sep. 2000;18(9):989-94.
Harrison, J. L., et al., Screen of Phage Antibody Libraries, Methods in Enzymology, 1996;267:83-109.
Hawkins, C. L., et al., Generation and propagation of radical reactions on proteins, ochim Biophys Acta. Apr. 2, 2001;1504(2-3):196-219.
Hawkins, C. L., et al., Superoxide radicals can act synergistically with hypochlorite to induce damage to proteins, FEBS Lett. Jan. 2, 2002;510(1-2):41-4.
Holliger, P., et al., Engineered antibody fragments and the rise of single domains, Nat Biotechnol. Sep. 2005;23(9):1126-36.
Massova, I., et al., Structural Insights into the Catalytic Domains of Human Matrix Metalloprotease-2 and Human Matrix Metalloprotese-9: Implications for Substrate Specificities, J. Mol. Model, 1997;3:17-30.
McKerrow, J. H., Development of cysteine protease inhibitors as chemotherapy for parasitic diseases: insights on safety, target validation, and mechanism of action, Int J Parasitol. Jun. 1999;29(6):833-7.
Miller, E. J., Structural studies on cartilage collagen employing limited cleavage and solubilization with pepsin, Biochemistry. Dec. 19, 1972;11(26):4903-9.

(Continued)

*Primary Examiner* — Gerald R Ewoldt
(74) *Attorney, Agent, or Firm* — Stradley Ronon Stevens & Young, LLP

(57) ABSTRACT

The present invention provides a composition comprising an antibody or fragment thereof against oxidized Collagen II (CII) in which the antibody or fragment thereof is conjugated to a pharmaceutically active moiety. The invention also provides a composition comprising an antibody or fragment thereof against oxidized Collagen II (Gil) and a detectable label. The invention further provides the use of such compositions in medicine, in particular for the treatment of an arthropathy, and in methods of diagnosis.

21 Claims, 13 Drawing Sheets

(56) References Cited

OTHER PUBLICATIONS

Nagai, T., et al., In vitro and in vivo efficacy of a recombinant immunotoxin against folate receptor beta on the activation and proliferation of rheumatoid arthritis synovial cells, Arhritis Rheum. Oct. 2006;54(10):3126-34.

Nagase, H., et al., Human matrix metalloproteinase specificity studies using collagen sequence-based synthetic peptides, Biopolymers. 1996;40(4):399-416.

Nissim, A., et al., Generation of neoantigenic epitopes after post-translational modification of type II collagen by factors present within the inflamed joint, Arthritis Rheum. Dec. 2005;52(12):3829-38.

Rosenberg, L., Chemical basis for the histological use of safranin O in the study of articular cartilage, J Bone Joint Surg Am. Jan. 1971;53(1):69-82.

Tort, J., et al., Proteinases and associated genes of parasitic helminths, Adv Parasitol. 1999;43:161-266.

Trachsel, E., et al., Antibody-mediated delivery of IL-10 inhibits the progression of established collagen-induced arthritis, Arthritis Res Ther. 2007;9(1):R9.

Uhlmann, E., Peptide nucleic acids (PNA) and PNA-DNA chimeras: from high binding affinity towards biological function, ol Chem. Aug.-Sep. 1998;379(8-9):1045-52.

Voth, B. R., et al., Differentially expressed Leishmania major gp63 genes encode cell surface leishmanolysin with distinct signals for glycosylphosphatidylinositol attachment, Mol Biochem Parasitol. May 15, 1998;93(1):31-41.

Vu, T. H., et al., Matrix metalloproteinases: effectors of development and normal physiology, Genes Dev. Sep. 1, 2000;14(17):2123-33.

Williams, L. W., et al., Complement: function and clinical relevance, Ann Allergy. Apr. 1988;60(4):293-300.

Winter, G., et al., Making antibodies by phage display technology, Annu Rev Immunol. 1994;12:433-55.

Wu, A. M., et al., Arming antibodies: prospects and challenges for immunoconjugates, Nat Biotechnol. Sep. 2005;23(9):1137-46.

Wyman, T. B., et al., Design, synthesis, and characterization of a cationic peptide that binds to nucleic acids and permeabilizes bilayers, Biochemistry. Mar. 11, 1997;36(10):3008-17.

Yoshioka, M., et al., Effect of proteases from Porphyromogingivalis on adhesion molecules of human periodontal ligament fibroblast cells, Folia Pharmacol., 1997;110:347-55.

Young A. R., et al., Biochemical aspects of egg hatch in endo- and ectoparasites: potential for rational drug design, Int J Parasitol. Jun. 1999;29(6):861-7.

Yu, Q., et al., Cell surface-localized matrix metalloproteinase-9 proteolytically activates TGF-beta and promotes tumor invasion and angiogenesis, Genes Dev. Jan. 15, 2000;14(2):163-76.

Zhang, Y., Molecular characterization of a protease secreted by Erwinia amylovora, J Mol Biol. Jun. 25, 1999;289(5):1239-51.

Burkhardt, H., et al., Epitope-specific recognition of type II collagen by rheumatoid arthritis antibodies is shared with recognition by antibodies that are arthritogenic in collagen-induced arthritis in the mouse, Arthritis Rheum. Sep. 2002;46(9):2339-48.

Ferrari-Lacraz, S., et al., Targeting IL-15 receptor-bearing cells with an antagonist mutant IL-15/Fc protein prevents disease development and progression in murine collagen-induced arthritis, J Immunol. Nov. 1, 2004;173(9):5818-26.

Quattrocchi, E., et al., Paradoxical effects of adenovirus-mediated blockade of TNF activity in murine collagen-induced arthritis, J Immunol. Jul. 15, 1999;163(2):1000-9.

Zuo, L., et al., A single-chain class II MHC-IgG3 fusion protein inhibits autoimmune arthritis by induction of antigen-specific hyporesponsiveness, J Immunol. Mar. 1, 2002;168(5)2554-9.

Altman et al., Development of criteria for the classification and reporting of osteoarthritis, Arthritis and Rheumatism 1986 29(8):1039-1049.

Fransen et al., Isometric muscle force measurement for clinicians treating patients with osteoarthritis of the knee, Arthritis Care & Research 2003 49(1):29-35.

Nissim et al., Generation of neoantigenic epitopes after postranslational modification of type II collagen by factors present within the inflamed joint, Arthritis & Rheumatism 2005 52(12):3829-3838.

Pruijn et al., The use of citrullinated peptides and proteins for the diagnosis of rheumatoid arthritis, Arthritis Res & Ther 2010 12(1):203.

Strollo et al., Autoantibodies to prosttranslationally modified type II collagen as potentail biomarkers for rheumatoid arthritis, Arthritis & Rheumatism 2013 65(7):1702-1712.

Office Action dated Aug. 9, 2017 in related U.S. Appl. No. 14/765,863.

* cited by examiner

Special Localisation of 1-11E in inflamed paw

FIG. 5

| Protein | Sequence |
| --- | --- |
| MMP-1/MMP-8 | |
| Human type I collagen (α1) | Ala-Pro-Gln-Gly$_{775}$~Ile$_{776}$-Ala-Gly-Gln (SEQ ID NO: 151) |
| Human type I collagen (α2) | Gly-Pro-Gln-Gly$_{775}$~Leu$_{776}$-Leu-Gly-Ala (SEQ ID NO: 152) |
| Human type II collagen | Gly-Pro-Gln-Gly$_{775}$~Leu$_{776}$-Ala-Gly-Gln (SEQ ID NO: 153) |
| Human type III collagen | Gly-Pro-Leu- Gly$_{775}$~Ile$_{776}$-Ala-Gly-Ile (SEQ ID NO: 154) |
| Human α$_2$-macroglobulin | Gly-Pro-Glu-Gly$_{679}$~Leu$_{680}$-Arg-Val-Gly (SEQ ID NO: 155) |
| Rat α$_2$-macroglobulin | Ala-Ala-Tyr-His$_{681}$~Leu$_{682}$-Val-Ser-Gln (SEQ ID NO: 156) |
| Rat α$_2$-macroglobulin | Met-Asp-Ala-Phe$_{691}$~Leu$_{692}$-Glu-Ser-Ser (SEQ ID NO: 157) |
| Rat α$_1$-macroglobulin | Glu-Pro-Gln-Ala$_{683}$~Leu$_{684}$-Ala-Met-Ser (SEQ ID NO: 158) |
| Rat α$_1$-macroglobulin | Gln-Ala-Leu-Ala$_{685}$~Met$_{686}$-Ser-Ala-Ile (SEQ ID NO: 159) |
| Chicken ovostatin | Pro-Ser-Tyr-Phe$_{673}$~Leu$_{674}$-Asn-Ala-Gly (SEQ ID NO: 160) |
| Human pregnancy zone protein | Tyr-Glu-Ala-Gly$_{685}$~Leu$_{686}$-Gly-Val-Val (SEQ ID NO: 161) |
| Human pregnancy zone protein | Ala-Gly-Leu-Gly$_{687}$~Val$_{688}$-Val-Glu-Arg (SEQ ID NO: 162) |
| Human pregnancy zone protein | Ala-Gly-Leu-Gly$_{757}$~Ile$_{758}$-Ser-Ser-Thr (SEQ ID NO: 163) |
| α$_1$-protease inhibitor | Gly-Ala-Met-Phe$_{352}$~Leu$_{353}$-Glu-Ala-Ile (SEQ ID NO: 164) |
| Human aggrecan | Ile-Pro-Glu-Asn$_{341}$~Phe$_{342}$-Phe-Gly-Val (SEQ ID NO: 165) |
| Human aggrecan | Thr-Glu-Gly-Glu$_{373}$~Ala$_{374}$-Arg-Gly-Ser (SEQ ID NO: 166) |
| Human cartilage link | Arg-Ala-Ile-His$_{16}$~Ile$_{17}$-Gln-Ala-Glu (SEQ ID NO: 167) |
| Human insulin-like growth factor binding protein-3 | Leu-Arg-Ala-Tyr$_{99}$~Leu$_{100}$-Leu-Pro-Ala (SEQ ID NO: 168) |

A
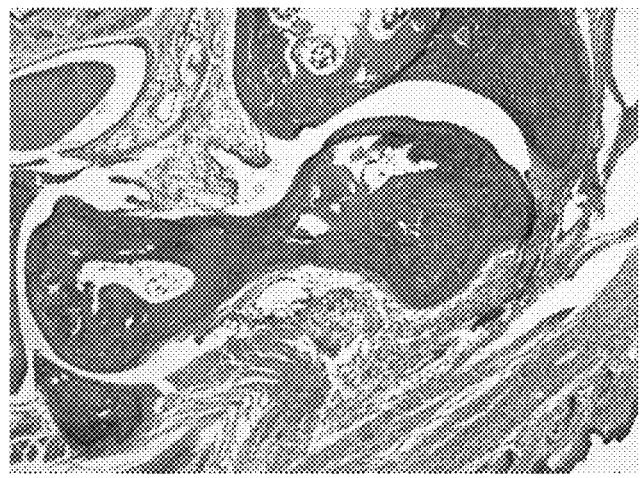
B
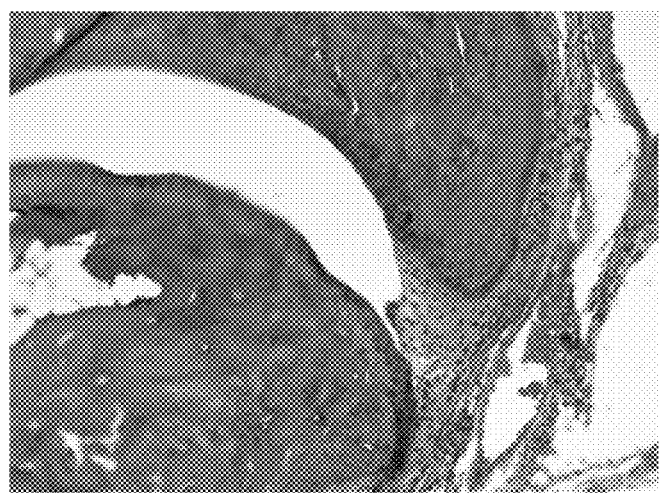
Figure 8

C
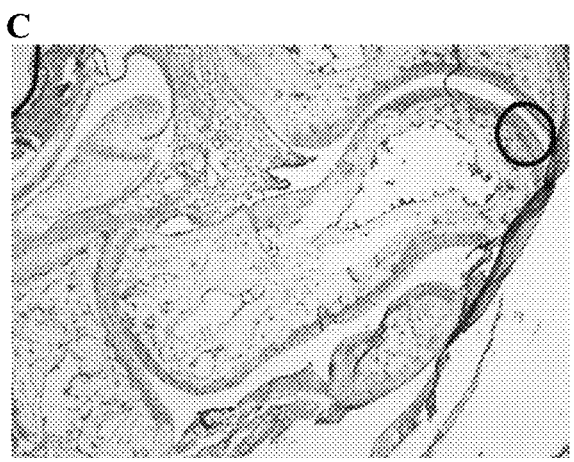
D
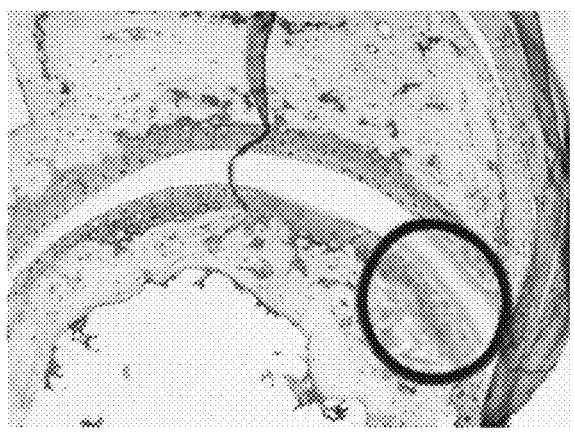
E
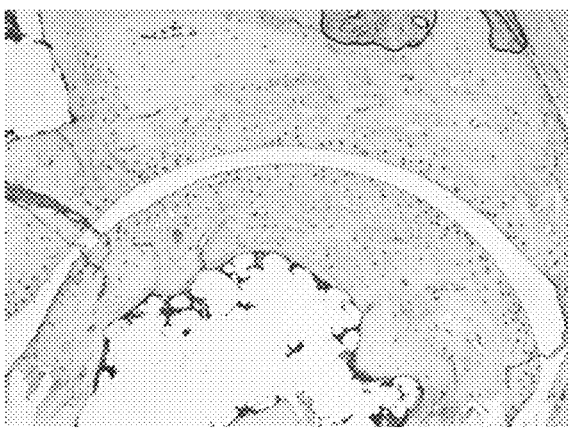
Figure 8
Cont'd

A
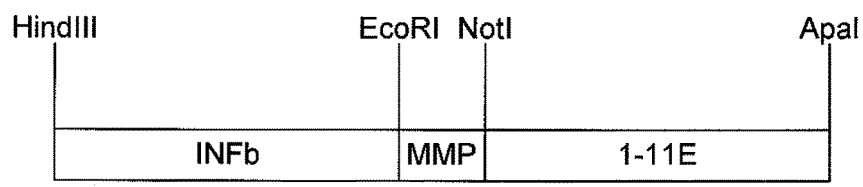
B
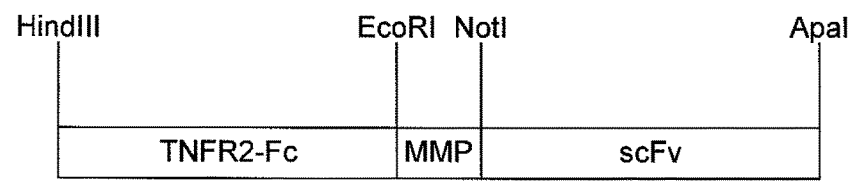
Figure 10
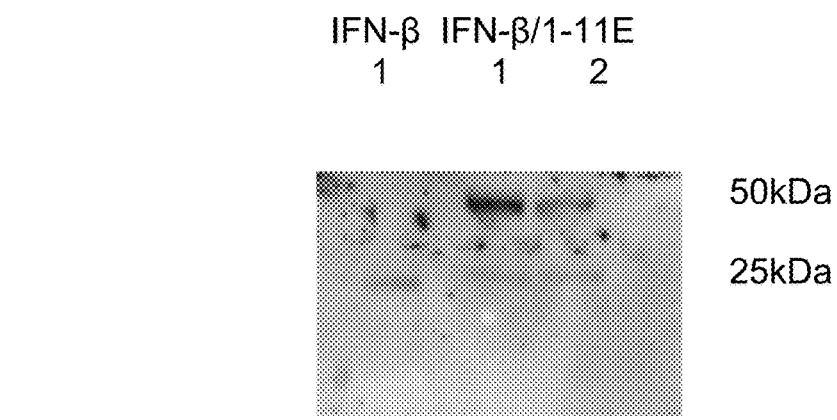
IFN-beta (23.2kDa) + scFv (26.6kDa) = 50.4kDa
Figure 12

Large-scale protein expression using the Bac-to-Bac system

FIG. 13
A
TNFR2Fc/1-11E Clone 1
BV: 100 50 25 12 6 0
75kDa
50kDa
37kDa
B
TNFR2Fc/1-11E Clone 3
BV: 100 50 25 12 6 0
75kDa
50kDa
37kDa
C
TNFR2Fc/C7 Clone
BV: 100 50 25 12 6 0
75kDa
50kDa
37kDa

ANTIBODY AND USE IN DIAGNOSIS AND THERAPY OF ARTHROPATHIES

CROSS-REFERENCE TO RELATED APPLICATIONS

This application is the U.S. National Stage filing of International Application Serial No. PCT/GB2008/001526 filed May 2, 2008, which claims priority to Great Britain Application No. GB 0708585.5 filed May 3, 2007, each of which is incorporated herein by reference in its entirety.

The present invention relates to a novel antibody and its use in the diagnosis and therapy of inflammatory diseases of the joints such as rheumatoid arthritis (RA) and osteoarthritis (OA).

INTRODUCTION

The final outcome of most rheumatic conditions, the leading cause of disabilities in the western world, is breakdown of articular cartilage. This breakdown is the final outcome of inflammatory events in both rheumatoid arthritis (RA) and osteoarthritis (OA) mediated by either influx of activated leukocytes (RA) or activated chondrocytes (OA). Pro-inflammatory cytokine blockade such as anti-TNFa and IL-1Ra is therefore currently used to treat arthritic conditions, mainly RA. These treatments however, are not consistently effective and the number of patients that fail anti-TNF therapy is increasing. Especially for anti-TNFa treatment there is a risk of serious infections and malignancies. These systemic side effects could be minimised by the development of technologies to target therapeutic agents specifically to the inflamed tissues, but has so far been impeded by the lack of proper target epitope(s) that would be present uniquely in the diseased joint and not in the healthy joint.

RA is a classic inflammatory form of arthritis, which is a chronic autoimmune disease with extensive synovial inflammation. Influx of activated leukocytes infiltrating the inflamed synovial membrane results in up-regulation of inflammatory cytokines such as TNFa, interleukin-1 (IL-1) and interleukin-6 (IL-6) leading to increase in the levels of matrix metalloproteases (MMP). Moreover, infiltrated inflammatory cells consume increased amounts of oxygen, resulting in the generation of reactive oxidant species (ROS) including superoxide radicals ($O_2$), hydrogen peroxide ($H_2O_2$), hydroxyl radicals (OH), hypochlorous acid (HOCl), nitric oxide (NO) and peroxynitrite (ONOO). In addition, sequential oxidative reactions generate reactive oxidants such as advanced glycation end-products (AGE). The combined activities of MMP and ROS may be the cause of the excessive degradation of the extracellular matrix leading to cartilage destruction.

The immuno-pathological events following the ROS reactivity with cartilage specific collagen type II (CII) protein have been studied recently. A substantial increase in binding of RA sera to CII after chemical post-translational modification in vitro by ROS has been demonstrated in comparison to binding to native non-modified CII, which is significantly greater than in non-RA sera. Post-translational modification in the acute and chronic inflammation by ROS has also been postulated by the presence of other ROS damaged proteins and auto-antibodies against other auto-antigens that are post-translationally modified by ROS. Generation of neoantigenic epitopes on modified CII has been reported in Nissim et al *Arthritis & Rheumatism*, volume 52 (12) pages 3829-3838 (2005)). Antibodies against IgG-AGE and a T cell response against IgG modified by HOCl and peroxynitrite have also been observed.

Although synovial inflammation in OA is not as extensive as in RA and inflammatory cells are not significant in numbers, low grade synovitis is nearly a constant feature in OA. Abnormal mechanical force appears to stimulate chondrocytes to produce the same inflammatory mediators and ROS as the infiltrated leukocytes present in inflamed RA joints leading to post translational modifications of CII. There is a report of elevated levels of nitrated CII peptide in sera of patients with OA. The presence of strong staining of nitrotyrosine and low antioxidative capacity in the degenerative region of OA cartilage compared with the intact region from the same sample suggests a possible correlation between oxidative damage and cartilage degradation. As in RA, indirect involvement of oxidative stress has also been evidenced in OA by the fact that: (i) OA is strongly linked with age and in aged cartilage there is accumulation of AGE; and (ii) there is accumulation of lipid peroxidation product and nitrotyrosine.

There is a need for improved means for diagnosing inflammatory diseases of the joints and for improved therapies for arthropathies such as rheumatoid arthritis (RA) and osteoarthritis (OA).

It has been found that an antibody raised against post-translationally modified Collagen II (CII) can specifically target the antibody to the sites of inflammation in the joints. This degree of specificity is important since native CII may be present in both inflamed and healthy joints also.

According to a first aspect of the invention, there is provided a composition comprising an antibody or fragment thereof against oxidised Collagen II (CII) in which the antibody or fragment thereof is conjugated to a pharmaceutically active moiety.

The present invention therefore provides a novel approach to the targeting of drugs to self-epitopes on Collagen II that are a normal component of the tissue but which become immunogenic after post-translational modification by free radicals as part of a disease process affecting Collagen II.

The antibody may be a polyclonal antibody or a monoclonal antibody. It may be a human or humanized or chimeric antibody with sequences, residues or domains derived from more than one animal species. Fragments of antibodies include Fc, Fab, scFv, single domain (dAb) antibody, diabody, minibody, and scFv-Fc fragments In one embodiment of the invention, the antibody comprises CDR sequences in the Variable Heavy (VH) Chains and Variable Light (VL) chains as shown in Table 1. CDRH2 and CDRH3 are in the VH chain and CDRL2 and CDRL3 are in the VL chain.

TABLE 1

| CDRH2 | CDRH3 | CDRL2 | CDRL3 |
|---|---|---|---|
| DISSTGSYTAYADSVKG (SEQ ID NO: 1) | GAGSFDY (SEQ ID NO: 39) | AASALQS (SEQ ID NO: 61) | QQSSSTPTT (SEQ ID NO: 86) |

TABLE 1-continued

| CDRH2 | CDRH3 | CDRL2 | CDRL3 |
|---|---|---|---|
| AISAAGTATAYADSVKG (SEQ ID NO: 2) | GYDTFDY (SEQ ID NO: 40) | AASSLQS (SEQ ID NO: 62) | QQNYGYPNT (SEQ ID NO: 87) |
| SISNSGSYTDYADSVKG (SEQ ID NO: 3) | GYGSFDY (SEQ ID NO: 41) | AASTLQS (SEQ ID NO: 63) | QQANSSPDT (SEQ ID NO: 88) |
| SINNYGSNTAYADSVKG (SEQ ID NO: 4) | GYSSFDY (SEQ ID NO: 42) | AASYLQS (SEQ ID NO: 64) | QQTSSSPDT (SEQ ID NO: 89) |
| SINNYGSNTAYADSVKG (SEQ ID NO: 4) | GYSSFDY (SEQ ID NO: 42) | AASYLQS (SEQ ID NO: 64) | QQTSSSPDT (SEQ ID NO: 89) |
| SISYTGNSTDYADSVKG (SEQ ID NO: 5) | GYTAFDY (SEQ ID NO: 43) | YASYLQS (SEQ ID NO: 65) | QQADSTPTT (SEQ ID NO: 90) |
| SISYTGNSTDYADSVKG (SEQ ID NO: 5) | GYTAFDY (SEQ ID NO: 43) | YASYLQS (SEQ ID NO: 65) | QQADSTPTT (SEQ ID NO: 90) |
| SISYTGNSTDYADSVKG (SEQ ID NO: 5) | GYTAFDY (SEQ ID NO: 43) | YASYLQS (SEQ ID NO: 65) | QQADSTPTT (SEQ ID NO: 90) |
| SISYTGNSTDYADSVKG (SEQ ID NO: 5) | GYTAFDY (SEQ ID NO: 43) | YASYLQS (SEQ ID NO: 65) | QQADSTPTT (SEQ ID NO: 90) |
| SISYTGNSTDYASVKG (SEQ ID NO: 5) | GYTAFDY (SEQ ID NO: 43) | YASYLQS (SEQ ID NO: 65) | QQADSTPTT (SEQ ID NO: 90) |
| NIATDGTTTYYADSVKG (SEQ ID NO: 6) | NSTYFDY (SEQ ID NO: 44) | SASTLQS (SEQ ID NO: 66) | QQAATSPTT (SEQ ID NO: 91) |
| SISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| SISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| SISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| SISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| SISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| SISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| SISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| SISYTGDSTYYADSVKG (SEQ ID NO: 8) | NYSAFDY (SEQ ID NO: 46) | YASYLQS (SEQ ID NO: 65) | QQADSTPTT (SEQ ID NO: 90) |
| SINDSGTTTYYADSVKG (SEQ ID NO: 9) | NYSAFDY (SEQ ID NO: 46) | AASDLQS (SEQ ID NO: 67) | QQSDSAPTT (SEQ ID NO: 93) |
| SIDSAGASTYYADSVKG (SEQ ID NO: 10) | NYSAFDY (SEQ ID NO: 46) | NASSLQS (SEQ ID NO: 68) | QQSDTYPST (SEQ ID NO: 94) |
| SISYTGDSTYYADSVKG (SEQ ID NO: 8) | NYSAFDY (SEQ ID NO: 46) | TASNLQS (SEQ ID NO: 69) | QQSYASPTT (SEQ ID NO: 95) |
| SISYTGDSTYYADSVKG (SEQ ID NO: 8) | NYSAFDY (SEQ ID NO: 46) | TASNLQS (SEQ ID NO: 69) | QQSYASPTT (SEQ ID NO: 95) |
| SISYTGDSTYYADSVKG (SEQ ID NO: 8) | NYSAFDY (SEQ ID NO: 46) | TASNLQS (SEQ ID NO: 69) | QQTGSYPTT (SEQ ID NO: 96) |
| SINATGYGTYYADSVKG (SEQ ID NO: 11) | NYSDFDY (SEQ ID NO: 47) | SASALQS (SEQ ID NO: 70) | QQGDSYPTT (SEQ ID NO: 97) |
| SINSNGTDTYYADSVKG (SEQ ID NO: 12) | NYSDFDY (SEQ ID NO: 47) | TASALQS (SEQ ID NO: 71) | QQGYGAPTT (SEQ ID NO: 98) |
| SISATGSSTYYADSVKG (SEQ ID NO: 13) | NYSDFDY (SEQ ID NO: 47) | SASDLQS (SEQ ID NO: 72) | QQSSYTPTT (SEQ ID NO: 99) |

TABLE 1-continued

| CDRH2 | CDRH3 | CDRL2 | CDRL3 |
| --- | --- | --- | --- |
| SISATGSSTYYADSVKG (SEQ ID NO: 13) | NYSDFDY (SEQ ID NO: 47) | SASDLQS (SEQ ID NO: 72) | QQSSYTPTT (SEQ ID NO: 99) |
| SIDDSGATTYYADSVKG (SEQ ID NO: 14) | NYSSFDY (SEQ ID NO: 48) | YASSLQS (SEQ ID NO: 73) | QQAANYPTT (SEQ ID NO: 100) |
| SIDDSGATTYYADSVKG (SEQ ID NO: 14) | NYSSFDY (SEQ ID NO: 48) | YASSLQS (SEQ ID NO: 73) | QQAANYPTT (SEQ ID NO: 100) |
| SIDDSGATTYYADSVKG (SEQ ID NO: 14) | NYSSFDY (SEQ ID NO: 48) | YASSLQS (SEQ ID NO: 73) | QQAANYPTT (SEQ ID NO: 100) |
| SIDDSGATTYYADSVKG (SEQ ID NO: 14) | NYSSFDY (SEQ ID NO: 48) | YASSLQS (SEQ ID NO: 73) | QQAANYPTT (SEQ ID NO: 100) |
| SIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| SIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| SIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| SIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| SIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| SIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| SISTNGSSTYYADSVKG (SEQ ID NO: 16) | NYSSFDY (SEQ ID NO: 48) | DASGLQS (SEQ ID NO: 74) | QQGDTSPTT (SEQ ID NO: 102) |
| SISTNGSSTYYADSVKG (SEQ ID NO: 16) | NYSSFDY (SEQ ID NO: 48) | DASGLQS (SEQ ID NO: 74) | QQGDTSPTT (SEQ ID NO: 102) |
| SISTNGSSTYYADSVKG (SEQ ID NO: 16) | NYSSFDY (SEQ ID NO: 48) | DASGLQS (SEQ ID NO: 74) | QQGDTSPTT (SEQ ID NO: 102) |
| SISTNGSSTYYADSVKG (SEQ ID NO: 16) | NYSSFDY (SEQ ID NO: 48) | DASGLQS (SEQ ID NO: 74) | QQGDTSPTT (SEQ ID NO: 102) |
| SIDTTGTTTYFADSVKG (SEQ ID NO: 17) | NYSSFDY (SEQ ID NO: 48) | SASYLQS (SEQ ID NO: 75) | QQGYSAPTT (SEQ ID NO: 103) |
| TISYSGNNTYYADSVKG (SEQ ID NO: 18) | NYSSFDY (SEQ ID NO: 48) | TASSLQS (SEQ ID NO: 76) | QQGYTSPTT (SEQ ID NO: 104) |
| SIDAGGNGTYYADSVKG (SEQ ID NO: 19) | NYSSFDY (SEQ ID NO: 48) | TASNLQS (SEQ ID NO: 77) | QQNNYYPTT (SEQ ID NO: 105) |
| SIDAGGNGTYYADSVKG (SEQ ID NO: 19) | NYSSFDY (SEQ ID NO: 48) | YASSLQS (SEQ ID NO: 73) | QQSDAYPTT (SEQ ID NO: 106) |
| SIDAGGNGTYYADSVKG (SEQ ID NO: 19) | NYSSFDY (SEQ ID NO: 48) | YASSLQS (SEQ ID NO: 73) | QQSDAYPTT (SEQ ID NO: 106) |
| SIDAGGNGTYYADSVKG (SEQ ID NO: 19) | NYSSFDY (SEQ ID NO: 48) | YASSLQS (SEQ ID NO: 73) | QQSDAYPTT (SEQ ID NO: 106) |
| SIDAGGNGTYYADSVKG (SEQ ID NO: 19) | NYSSFDY (SEQ ID NO: 48) | YASSLQS (SEQ ID NO: 73) | QQSDAYPTT (SEQ ID NO: 106) |
| SIDSAGNATYYADSVKG (SEQ ID NO: 20) | NYSSFDY (SEQ ID NO: 48) | AASTLQS (SEQ ID NO: 78) | TSNYPTTQQ (SEQ ID NO: 107) |
| SITDSGDTTYYADSVKG (SEQ ID NO: 21) | NYSTFDY (SEQ ID NO: 49) | SASSLQS (SEQ ID NO: 79) | QQSNATPTT (SEQ ID NO: 108) |
| SITDSGDTTYYADSVKG (SEQ ID NO: 21) | NYSTFDY (SEQ ID NO: 49) | SASSLQS (SEQ ID NO: 79) | QQSNATPTT (SEQ ID NO: 108) |
| SITDSGDTTYYADSVKG (SEQ ID NO: 21) | NYSTFDY (SEQ ID NO: 49) | SASSLQS (SEQ ID NO: 79) | QQSNATPTT (SEQ ID NO: 108) |

TABLE 1-continued

| CDRH2 | CDRH3 | CDRL2 | CDRL3 |
|---|---|---|---|
| SITDSGDTTYYADSVKG (SEQ ID NO: 21) | NYSTFDY (SEQ ID NO: 49) | SASSLQS (SEQ ID NO: 79) | QQSNATPTT (SEQ ID NO: 108) |
| SITDSGDTTYYADSVKG (SEQ ID NO: 21) | NYSTFDY (SEQ ID NO: 49) | SASSLQS (SEQ ID NO: 79) | QQSNATPTT (SEQ ID NO: 108) |
| SIATTGDNTYYADSVKG (SEQ ID NO: 22) | NYSYFDY (SEQ ID NO: 50) | TASTLQS (SEQ ID NO: 80) | QQAAGNPTT (SEQ ID NO: 109) |
| AINAYGGSTYYADSVKG (SEQ ID NO: 23) | NYSYFDY (SEQ ID NO: 50) | AASSLQS (SEQ ID NO: 62) | QQGSDYPTT (SEQ ID NO: 110) |
| AINAYGGSTYYADSVKG (SEQ ID NO: 23) | NYSYFDY (SEQ ID NO: 50) | AASSLQS (SEQ ID NO: 62) | QQGSDYPTT (SEQ ID NO: 110) |
| SIATTGTSTTYYADSVKG (SEQ ID NO: 24) | NYSYFDY (SEQ ID NO: 50) | TASSLQS (SEQ ID NO: 76) | QQGSTAPTT (SEQ ID NO: 111) |
| SIATTGTSTTYYADSVKG (SEQ ID NO: 24) | NYSYFDY (SEQ ID NO: 50) | TASSLQS (SEQ ID NO: 76) | QQGSTAPTT (SEQ ID NO: 111) |
| TIDTAGSYTDYADSVKG (SEQ ID NO: 25) | NYSYFDY (SEQ ID NO: 50) | GASTLQS (SEQ ID NO: 81) | QQSTASPST (SEQ ID NO: 112) |
| SISNNGSSTYYADSVKG (SEQ ID NO: 26) | NYSYFDY (SEQ ID NO: 50) | AASNLQS (SEQ ID NO: 82) | QQTSSYPTT (SEQ ID NO: 113) |
| SIAYGGAGTDYADSVKG (SEQ ID NO: 27) | NYTAFDY (SEQ ID NO: 51) | AASYLQS (SEQ ID NO: 64) | QQGAGSPST (SEQ ID NO: 114) |
| AIANTGSATNYADSVKG (SEQ ID NO: 28) | NYTAFDY (SEQ ID NO: 51) | DASTLQS (SEQ ID NO: 83) | QQRNTSPTT (SEQ ID NO: 115) |
| SISTAGTYTDYADSVKG (SEQ ID NO: 29) | NYTDFDY (SEQ ID NO: 52) | SASYLQS (SEQ ID NO: 75) | QQSNTSPAT (SEQ ID NO: 116) |
| SISTAGTYTDYADSVKG (SEQ ID NO: 29) | NYTDFDY (SEQ ID NO: 52) | SASYLQS (SEQ ID NO: 75) | QQSNTSPAT (SEQ ID NO: 116) |
| SINDTGYTTYYADSVKG (SEQ ID NO: 30) | NYTYFDY (SEQ ID NO: 53) | TASTLQS (SEQ ID NO: 80) | QQAYTAPTT (SEQ ID NO: 117) |
| SIASSGTTTYYADSVKG (SEQ ID NO: 31) | SYADFDY (SEQ ID NO: 54) | AASNLQS (SEQ ID NO: 82) | QQADTYPTT (SEQ ID NO: 118) |
| TITS TGAATAYADSVKG (SEQ ID NO: 32) | SYATFDY (SEQ ID NO: 55) | AASYLQS (SEQ ID NO: 64) | QQAANSPDT (SEQ ID NO: 119) |
| AIDGTGYGTAYADSVKG (SEQ ID NO: 33) | SYDTFDY (SEQ ID NO: 56) | GASSLQS (SEQ ID NO: 84) | QQTSDYPNT (SEQ ID NO: 120) |
| SIANAGTATYYADSVKG (SEQ ID NO: 34) | SYSNFDY (SEQ ID NO: 57) | SASTLQS (SEQ ID NO: 66) | QQASTSPTT (SEQ ID NO: 121) |
| SIDSAGDSTYYADSVKG (SEQ ID NO: 35) | SYSYFDY (SEQ ID NO: 58) | TASYLQS (SEQ ID NO: 85) | QQASDYPTT (SEQ ID NO: 122) |
| SISSSGDTTYYADSVKG (SEQ ID NO: 36) | SYSYFDY (SEQ ID NO: 58) | TASTLQS (SEQ ID NO: 80) | QQSSSNPTT (SEQ ID NO: 123) |
| SIDTGGSYTDYADSVKG (SEQ ID NO: 37) | SYTTFDY (SEQ ID NO: 59) | SASYLQS (SEQ ID NO: 75) | QQGSNSPTT (SEQ ID NO: 124) |
| SIDTGGSYTDYADSVKG (SEQ ID NO: 37) | SYTTFDY (SEQ ID NO: 59) | SASYLQS (SEQ ID NO: 75) | QQGSNSPTT (SEQ ID NO: 124) |
| SIDTGGSYTDYADSVKG (SEQ ID NO: 37) | SYTTFDY (SEQ ID NO: 59) | SASYLQS (SEQ ID NO: 75) | QQGSNSPTT (SEQ ID NO: 124) |
| SIDTGGSYTDYADSVKG (SEQ ID NO: 37) | SYTTFDY (SEQ ID NO: 59) | SASYLQS (SEQ ID NO: 75) | QQGSNSPTT (SEQ ID NO: 124) |
| SIDASGANTAYADSVKG (SEQ ID NO: 38) | TYGTFDY (SEQ ID NO: 60) | SASYLQS (SEQ ID NO: 75) | QQSATTPDT (SEQ ID NO: 125) |

In one embodiment of the invention, the antibody may be an scFv selected from the group consisting of the following: 3-11A, 6-6E, 1-7G, 3-7B, 6-9D, 1-1C, 1-8D, 1-3G, 4-12C, 6-3E, 6-9A, 1-12A, 4-6A, 4-8A, 4-9F, 4-4H, 3-3A, 3-6F, 6-10H, 12E, 3-5G, 3-4D, 3-5D, 6-4E, 3-6B, 3-6G, 4-HF, 6-7H, 1-11E, 1-2F, 1-6H, 3-8D, 1-4D, 4-2F, 3-3B, 3-5C, 6-9C, 4G, 3-12F, 3-4G, 6-HF, 6-11H, 3-2C, 5B, 6-10G, 1-4H, 4-5A, 4-1B, 4-12D, 6-4B, 1-2E, 1-7F, 1-10F, 1-9G, 4-1C, 6-7G, 3-7H, 6-1F, 6-3B, 4H, 3-9A, 6-10D, 3-5H, 3-2F, 1-6G, 3-11H, 6-9F, 3-9D, 4-3H, 3-3E, 3-10C, 3-11E, 6-8C, 6-11D, 4-5H, 6-5F, 6-7F, 1-10D These scFvs are listed in Table 3 in the Examples below and comprise the CDRH2, CDRH3, CDRL2 and CDRL3 sequences shown in Table 1.

In one embodiment of the invention, the scFv may comprise a sequence as shown in Table 2.

pharmaceutically active moiety is a peptide or peptide-based molecule the conjugation may be by means of a peptide bond, including the insertion of one or more amino acid residues.

The conjugation of a peptide or a peptide-based molecule may be achieved by any generally convenient chemical means or biological means (see for example, Wu & Senter *Nature Biotechnology*, volume 23 (9) pages 1137-1146 (2005); "*Chemistry of Protein Conjugation and Crosslinking*" by S. S. Wong, CRC Press Inc. (1991)).

Chemical conjugation typically uses a bifunctional chemical reagent, for example glutaraldehyde can link molecules to the N-terminus of a peptide, carbodiimide can link

TABLE 2

| Clone I.D. | VH-CDR2 | VH-CDR3 | VL-CDR2 | VL-CDR3 |
|---|---|---|---|---|
| 1-2E | SITDSGDTTYYADSVKG (SEQ ID NO: 21) | NYSTFDY (SEQ ID NO: 49) | SASSLQS (SEQ ID NO: 79) | QQSNATPTT (SEQ ID NO: 108) |
| 1-11E | SIDDSGATTYYADSVKG (SEQ ID NO: 14) | NYSSFDY (SEQ ID NO: 48) | YASSLQS (SEQ ID NO: 73) | QQAANYPTT (SEQ ID NO: 100) |
| 1-4D | SIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| 1-12A | SISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| 12E | SINDSGTTTYYADSVKG (SEQ ID NO: 9) | NYSAFDY (SEQ ID NO: 46) | AASDLQS (SEQ ID NO: 67) | QQSDSAPTT (SEQ ID NO: 93) |
| 3-9A | TIDTAGSYTDYADSVKG (SEQ ID NO: 25) | NYSYFDY (SEQ ID NO: 50) | GASTLQS (SEQ ID NO: 81) | QQSTASPST (SEQ ID NO: 112) |
| 3-5C | SIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| 3-11E | SIDSAGDSTYYADSVKG (SEQ ID NO: 35) | SYSYFDY (SEQ ID NO: 58) | TASYLQS (SEQ ID NO: 85) | QQASDYPTT (SEQ ID NO: 122) |
| 3-2F | AIANTGSATNYADSVKG (SEQ ID NO: 28) | NYTAFDY (SEQ ID NO: 51) | DASTLQS (SEQ ID NO: 83) | QQRNTSPTT (SEQ ID NO: 115) |
| 3-6G | SINSNGTDTYYADSVKG (SEQ ID NO: 12) | NYSDFDY (SEQ ID NO: 47) | TASALQS (SEQ ID NO: 71) | QQGYGAPTT (SEQ ID NO: 98) |
| 3-9D | SIASSGTTTYYADSVKG (SEQ ID NO: 31) | SYADFDY (SEQ ID NO: 54) | AASNLQS (SEQ ID NO: 82) | QQADTYPTT (SEQ ID NO: 118) |
| 6-3B | SIATTGTSTTYADSVKG (SEQ ID NO: 24) | NYSYFDY (SEQ ID NO: 50) | TASSLQS (SEQ ID NO: 76) | QQGSTAPTT (SEQ ID NO: 111) |
| 6-11D | SIDTGGSYTDYADSVKG (SEQ ID NO: 37) | SYTTFDY (SEQ ID NO: 59) | SASYLQS (SEQ ID NO: 75) | QQGSNSPTT (SEQ ID NO: 124) |
| 6-9F | SINDTGYTTYYADSVKG (SEQ ID NO: 30) | NYTYFDY (SEQ ID NO: 53) | TASTLQS (SEQ ID NO: 80) | QQAYTAPTT (SEQ ID NO: 117) |
| 6-7G | SIATTGDNTYYADSVKG (SEQ ID NO: 22) | NYSYFDY (SEQ ID NO: 50) | TASTLQS (SEQ ID NO: 80) | QQAAGNPTT (SEQ ID NO: 109) |

Typically, the scFv is 1-11E.

Oxidised Collagen II (CII) is post-translationally modified Collagen II (CII) that has been oxidised by non enzymatic glycation or by reactive oxidant species (ROS) which may include superoxide radical ($O_2$), hydrogen peroxide ($H_2O_2$), hydroxyl radical (OH), hypochlorous acid (HOCl), nitric oxide (NO) and peroxynitrite (ONOO).

The antigen may therefore be HOCl-Collagen II or Ribose-Collagen II.

The antibody or fragment thereof is conjugated to the pharmaceutically active moiety which may be a peptide or peptide-based molecule by any suitable means. Where the molecules to the C-terminus of a peptide, succinimide esters (e.g. MBS, SMCC) can bind free amino groups and cysteine residues, benzidine links to tyrosine residues, periodate attaches to carbohydrate groups and isothiocyanate can also link molecules to antibodies.

Alternatively, a fusion protein may be synthesised using standard recombinant molecular biology techniques (see for example, Sambrook et al "*Molecular Cloning: A Laboratory Manual*", 3$^{rd}$ edition, CSHL Press, (2001); Trachsel et al *Arthritis Research & Therapy*, volume 9 (1) R9 (2007); Nagai *Arthritis & Rheumatism*, volume 54 (10) pages 3126-

3134 (2006)). Methods for producing fusion proteins are described in the Examples herein.

In certain embodiments of the invention, the insertion of additional amino acid residues between the antibody or fragment thereof and the pharmaceutically active moiety may represent a site for cleavage by a protease. The proteolytic cleavage site may comprise any protease specific cleavage site. The proteolytic cleavage site may include, but is not limited to, a matrix metalloproteinase (MMP) cleavage site, a serine protease cleavage site, a site cleavable by a parasitic protease derived from a pathogenic organism (Zhang et al., J. Mol. Biol. 289, 1239-1251 (1999); Voth et al., Molecular and Biochemical Parasitology, 93, 31-41 (1998); Yoshioka et al., Folia Pharmacologica Japonica, 110, 347-355 (1997); Tort et al., Advances in Parasitology, 43, 161-266 (1999); McKerrow, International Journal for Parasitology, 29, 833-837 (1999); Young et al., International Journal for Parasitology, 29, 861-867 (1999); Coombs and Mottram, Parasitology, 114, 61-80 (1997)) or a site cleavable by the proteins of the complement cascade (Carroll, Annu. Rev. Immunol. 16, 545-568 (1998); Williams et al., Ann. Allergy, 60, 293-300 (1988)).

The MMP cleavage site may comprise any amino acid sequence which is cleavable by a MMP. The amino acid sequence of the MMP cleavage site may be encoded by a nucleic acid sequence coding for an MMP sequence as shown in FIG. 5 or a sequence of nucleotides which has at least 50%, 60%, 70%, 80%, 90%, 95% or 99% identity, using the default parameters of the BLAST computer program provided by HGMP, thereto. Preferably, the nucleic acid sequence encoding the MMP cleavage site comprises the minimum number of residues required for recognition and cleavage by MMP.

A MMP cleavage site may comprise a number of amino acid residues recognisable by MMP. Moreover, the amino acids of the MMP site may be linked by one or more peptide bonds which are cleavable, proteolytically, by MMP. MMPs which may cleave the MMP site include, but are not limited to, MMP1, MMP2, MMP3, MMP7, MMP8, MMP9 or MMP10 (Yu and Stamenkovic, Genes and Dev. 14, 163-176 (2000); Nagase and Fields, Biopolymers, 40, 399-416 (1996); Massoya et al., J. Mol. Model. 3, 17-30 (1997); reviewed in Vu and Werb, Genes and Dev. 14, 2123-2133 (2000)). The sequences of the protein cleavage sites of MMP1, MMP2, MMP3, MMP7, MMP8, MMP9 and MMP10 are shown in FIG. 5.

Preferably, the proteolytic cleavage site of the present invention is cleaved at sites of inflammation and tissue remodeling. More preferably, the proteolytic cleavage site of the present invention is a MMP cleavage site e.g. any one or more of MMP1, MMP2, MMP3, MMP7, MMP8, MMP9 or MMP10 as shown in FIG. 5.

The pharmaceutically active moiety may comprise one or more molecules which may be the same or different, one or more radioisotopes which may be the same or different, or one or more non-radioactive elements which may be the same or different.

In some embodiments of the invention, the pharmaceutically active moiety may comprise a polypeptide or non-polypeptide molecule. References to a polypeptide include a peptide and vice versa unless the context specifies otherwise.

The polypeptide may be an antibody or a fragment thereof, such as an anti-TNFalpha monoclonal antibody (for example infliximab or adalimumab), a soluble p75 TNF receptor molecule (for example etanercept) or a IL-1 receptor antagonist (for example anakinra). In such embodiments of the invention, the composition will therefore comprise a bispecific antibody which may be a diabody (scFv with a linker which is too short to allow pairing between VH and VL and therefore the domains are forced to pair with the complementary domain of another scFv to create two antigen binding site), a minibody (composed of two scFv moieties linked via a constant heavy chain region (CH3)), a scFv-Fc molecule, or an intact antibody molecule containing the two separate binding regions.

For example, a bispecific antibody may comprise a first binding region specific for modified Collagen II (CII) and a second binding region specific for anti-TNFa.

In one embodiment, the polypeptide is a TNF receptor (TNFR) antibody fusion protein, typically a TNFR2-Fc fusion protein.

A bispecific antibody of the invention may also further comprise another pharmaceutically active moiety. For example, a composition of the invention may comprise a first binding region specific for modified Collagen II, a second binding region specific for CD64, and a toxin, such as Ricin A.

Alternatively, the polypeptide may be a growth factor (e.g. TGFβ, epidermal growth factor (EGF), platelet derived growth factor (PDGF), nerve growth factor (NGF), colony stimulating factor (CSF) granulocyte/macrophage colony stimulating factor (GM-CSF), hepatocyte growth factor, insulin-like growth factor, placenta growth factor); differentiation factor, cytokine molecule, for example an interleukin, (e.g. IL1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20 or IL-21, either α or β), an interferon (e.g. IFN-α, IFN-β and IFN-γ), tumour necrosis factor (TNF), IFN-γ inducing factor (IGIF), a bone morphogenetic protein (BMP); a chemokine (for example a MIP (Macrophage Inflammatory Protein) e.g. MIP1α and MIP1β; a MCP (Monocyte Chemotactic Protein) e.g. MCP1, 2 or 3; RANTES (regulated upon activation normal T-cell expressed and secreted)); a trophic factor; a cytokine inhibitor; a cytokine receptor (for example, CD20, CD40, CD40L, CD64); a free-radical scavenging enzyme (e.g. superoxide dismutase or catalase), or a toxin (for example Ricin A toxin, or *Pseudomonas* exotoxin A), or an active fragment or portion thereof. Typically, the polypeptide is an interferon, typically IFN-β.

See for example, Trachsel et al *Arthritis Research & Therapy*, volume 9 (1) R9 (2007) reporting antibody-IL10 fusion protein; Nagai *Arthritis & Rheumatism*, volume 54 (10) pages 3126-3134 (2006) reporting antibody-toxin fusion protein.

Other examples of antibody-fusion proteins, include but are not limited to, antibody-TNFalpha, antibody-GM-CSF, and antibody-IL2 fusion proteins The pharmaceutically active polypeptide may be derived from the species to be treated e.g. human origin for the treatment of humans.

The composition may also comprise further peptide sequences which can target the composition inside a cell. Such intracellular targeting sequences include, but are not limited to, the TAT sequence YGRKKRQRRR (SEQ ID NO: 126) (see for example, Cohen-Saidon et al *Blood*, volume 102 (7), pages 2506-2512 (2003)).

As used herein "peptide mimetics" includes, but is not limited to, agents having a desired peptide backbone conformation embedded into a non-peptide skeleton which holds the peptide in a particular conformation. Peptide mimetics, which do not have some of the drawbacks of peptides, are of interest in those cases where peptides are not suitable in medicine.

Peptide mimetics may comprise a peptide backbone which is of the L or D conformation. Examples of peptide mimetics include melanocortin, adrenocorticotrophin hormone (ACTH) and other peptide mimetic agents which play a role in the central nervous system, endocrine system, in signal transduction and in infection and immunity.

The pharmaceutically active agent may comprise a chemical compound such as a chemotherapeutic agent or other synthetic drug. Alternatively, the pharmaceutically active agent may comprise a peptide nucleic acid (PNA) sequence e.g. a poly-lysine sequence which binds to nucleic acids and permeabilises lipid bilayers (Wyman et al., Biological Chemistry, 379, 1045-1052 (1998)) or a KALA peptide which facilitates transfer through lipid bilayers (Wyman et al., Biochemistry, 36, 3008-3017 (1997)).

The non-polypeptide may be a glycosaminoglycan molecule, such as glucosamine (suitably, glucosamine HCl) or chondroitin. Alternatively, the non-polypeptide molecule may be a non-steroidal anti-inflammatory drug (NSAID) such as a non-selective NSAID or a selective NSAID. Examples of non-selective NSAIDs include aspirin, ibuprofen, and naproxen. Examples of selective NSAIDs (also called COX-2 inhibitors) include celecoxib (Celebrex®), rofecoxib (Vioxx®) and valdecoxib (Bextra®)). Other substances may include steroids, such as cortisol, or polymeric molecules such as sodium hyaluronate or hyaluronic acid (for example hyaluronan (Hyalgan®) and hylan-GF-20 (Synvisc®)), or drug substances such as colchicine or hydroxychloroquine (Plaquenil®).

Non-polypeptides may be conjugated to the antibody or fragment thereof using a linker that may be a labile bond in order to permit release of the pharmaceutically active substance. For example, a hydrazone bond may be used where the drug is released under acidic conditions, or a disulfide bond which is reduced to release the drug, or also a peptide bond which is cleaved enzymatically by a protease as described above.

In some embodiments, the composition may comprise a radioactive element or a non-radioactive element. The radioisotope may be an alpha particle-emitting radionuclide such as $^{213}$Bi or $^{211}$At, a beta particle-emitting radionuclide such as $^{131}$I, $^{90}$Y, $^{177}$Lu or $^{67}$Cu, a gamma radiation-emitting radionuclide such as $^{99m}$Tc, $^{123}$I or $^{111}$In or a positron-emitting radionuclide such as $^{18}$F, $^{64}$Cu, $^{68}$Ga, $^{86}$Y or $^{124}$I. Radioisotopes may be used in order to render the composition detectably labelled for diagnostic uses of the composition.

Alternatively, the non-radioactive element may be Au, Fe, Cu, Pt or Ag.

Combinations of the various elements and substances described above may also be included as desired.

According to a second aspect of the invention, there is provided a composition of the first aspect for use in medicine. This aspect of the invention includes a composition of the first aspect for use in the treatment of an arthropathy, such as rheumatoid arthritis (RA) and osteoarthritis (OA). This aspect of the invention therefore extends to a method of treatment of an arthropathy, such as rheumatoid arthritis (RA) and osteoarthritis (OA), comprising the step of administering to a subject a composition of the first aspect of the invention. The present invention therefore also includes the use of a composition of the first aspect of the invention in the manufacture of a medicament for the treatment of an arthropathy, such as rheumatoid arthritis (RA) and osteoarthritis (OA).

A composition of the first aspect of the invention may therefore be formulated as a pharmaceutical composition. Suitably, a pharmaceutical composition may comprise a diluent, excipient, adjuvant and/or physiologically acceptable buffer.

The pharmaceutical composition may be administered in any effective, convenient manner effective for treating a disease as described above including, for instance, administration by oral, topical, intravenous, intramuscular, intra-articular, intranasal, or intradermal routes among others. In therapy or as a prophylactic, the composition of the invention may be administered to an individual as an injectable composition, for example as a sterile aqueous dispersion, preferably isotonic. The injection may suitably be made into the joint affected by the disease.

For administration to mammals, and particularly humans, it is expected that the daily dosage of the composition of the invention will be from 0.01 mg/kg body weight, typically around 1 mg/kg. The physician in any event will determine the actual dosage which will be most suitable for an individual which will be dependant on factors including the age, weight, sex and response of the individual. The above dosages are exemplary of the average case. There can, of course, be instances where higher or lower dosages are merited, and such are within the scope of this invention According to a third aspect of the present invention, there is provided a method for the diagnosis of an arthropathy, such as rheumatoid arthritis (RA) and osteoarthritis (OA), comprising the steps of administering a detectably labelled composition comprising an antibody or fragment thereof against oxidised Collagen II (CII) to a subject and subsequently detecting the composition. This aspect of the invention therefore extends to a detectably labelled composition comprising an antibody or fragment thereof against oxidised Collagen II (CII) for use in the diagnosis of an arthropathy, such as rheumatoid arthritis (RA) and osteoarthritis (OA). Such embodiments also extend to the use of such compositions in the manufacture of an agent for the diagnosis of an arthropathy, such as rheumatoid arthritis (RA) and osteoarthritis (OA).

The detectable label may be a radioactive or a fluorescent label. In some embodiments the radioisotope may be an alpha particle-emitting radionuclide such as $^{213}$Bi or $^{211}$At, a beta particle-emitting radionuclide such as $^{131}$I, $^{90}$Y, $^{177}$Lu or $^{67}$Cu, a gamma radiation-emitting radionuclide such as $^{99m}$Tc, $^{123}$I or $^{111}$In or a positron-emitting radionuclide such as $^{18}$F, $^{64}$Cu, $^{68}$Ga, $^{86}$Y or $^{124}$I. Radioisotopes may be used in order to render the composition detectably labelled for diagnostic uses of the composition.

For diagnostic purposes, fluorescent dyes such as Alexa Fluor 488 or the Cy3 monofunctional N-hydroxysuccinimide (NHS) ester could also be used.

According to a fourth aspect of the invention, there is provided a composition comprising an antibody or fragment thereof against oxidised Collagen II (CII) and a detectable label.

RA is the most common chronic inflammatory autoimmune disease, with disability occurring usually within 10 years. Over activation of the inflammatory pathway leads to synovitis, joint damage and destruction. Key players in the joint inflammation are inflammatory cytokines such as TNFa and IL-1. The efficacy of anti-TNFa monoclonal antibodies (Infliximab and Adalimumab), soluble p75 TNF receptors (Etanercept) and IL-1 receptor antagonist (Anakinra) in the treatment of RA patients unresponsive to traditional therapy is now well established but unfortunately might be associated with an increase in serious infection and malignancies. It is therefore becoming very important to develop targeted delivery of anti-proinflammatory drugs to the inflamed joint rather than systemic administration because cytokines exert their function as auto or paracrine factors with high concentrations only in close vicinity of the producing cell. Systemic administration of sufficient blocking agents that can block the local high physiological concentration will likely cause severe side effects.

Although CII is the best candidate to target therapy to the joint one needs to find a way to target the drugs solely to the inflamed joints. The present studies show the development of a targeting antibody that will specifically recognise collagen type II that has been modified by ROS present in inflamed joint which then allows targeting to inflammatory damage joint independently of the aetiology.

By employing the phage display human antibody library, a panel of human scFvs was developed (FIG. 1) that bind only to CII which was modified in vitro by HOCl or glycation, known reactive oxidants in RA. Most importantly this scFv binds only to damaged cartilage but not to normal cartilage (FIG. 3) and inversely correlates with the staining of safranin-O for the integrity of cartilage-specific proteoglycan. Most importantly, when inflammation was induced in only one paw in CH3 mice with antigen induced arthritis model 1-11E diabody localized only to the inflamed paw without any background to any of the other healthy paws (FIG. 4). This strongly supports the specificity of 1-11E for damaged CII in vivo in inflammation setting and therefore have potential for targeting anti-TNFa, other pro-inflammatory cytokine blockade or cartilage regenerating factors to inflamed joints. This approach is significantly different from targeting citrullinated peptides that appear as a good biomarker for disease in RA but could not be used as a targeting molecule as its tissue expression is not joint specific.

Preferred features of the second and subsequent aspects of the invention are as for the first aspect mutatis mutandis.

In one embodiment, a composition of the invention comprises mouse interferon-beta (IFN-β), the scFv 1-11E and a MMP cleavage site. Such a composition can be produced by creating pFastBac1.AH by cutting out a BamHI/HindIII fragment containing multiple cloning sites (MCS) from pFastBac1 (Invitrogen) and replacing this fragment with a linker to give another MCS of BamHI-KpnI-HindIII-ApaI, cloning mouse interferon b (mIFNb) into the HindIII-EcoRI sites and cloning MMP and 1-11E into the NotI and ApaI site as shown in FIG. 10A.

Mouse interferon-beta is typically amplified using primers having the sequences shown in SEQ ID NO: 129 (forward) and SEQ ID NO: 130 (reverse). 1-11E is typically amplified using primers having the sequences shown in SEQ ID NO: 131 (forward) and SEQ ID NO: 132 (reverse), wherein 1-11E is amplified with NotI/ApaI ends to include a histidine (His) tag.

1-11E is typically then cloned into FastBac1.AH mIFN-b/MMP/SP/His and cut with Not/Apa to liberate SP/His. The mIFN-beta/His construct is typically cloned by amplifying mIFN-b with HindIII/ApaI using primers having the sequence shown in SEQ ID NO: 129 (forward) and SEQ ID NO: 133 (reverse).

The constructs are then typically transformed into DH10Bac cells (Invitrogen).

In another embodiment, a composition of the invention comprises TNF receptor 2-Fc (TNFR2Fc), an scFv (either 1-11E or C7 as a negative control) and a MMP cleavage site.

Such a composition can be produced by creating pFastBac1.AH from pFastBac1 (Invitrogen) by cutting out a BamHI/HindIII fragment containing multiple cloning sites (MCS), and replacing this fragment with a linker to give another MCS of BamHI-KpnI-HindIII-ApaI, cloning TNFR2Fc into the HindIII-EcoRI sites and cloning a MMP cleavage site and scFv (1-11E or C7) into the NotI and ApaI sites as shown in FIG. 10B.

Mouse TNFR2-Fc is typically amplified using primers having the sequences shown in SEQ ID NO: 141 (forward) and SEQ ID NO: 142 (reverse). 1-11E is typically amplified using primers having the sequences shown in SEQ ID NO: 131 (forward) and SEQ ID NO: 132 (reverse), wherein 1-11E is amplified with NotI/ApaI ends to include a histidine (His) tag.

Expression of the constructs is typically carried out using a protocol set out in FIG. 11. Such a protocol typically involves the following steps:

1. Transforming the constructs into competent DH10Bac cells (Invitrogen) to generate bacmid vectors.
2. Confirming recombinant bacmid vectors by blue-white screening and PCR, typically according to Invitrogen instructions.
3. Transfecting bacmid DNA into Sf9 insect cells using cellfectin, typically according to Invitrogen instructions.
4. Harvesting baculovirus (P1) from the supernatant of transfected cells.
5. Using the harvested baculovirus to infect fresh Sf9 cells to amplify the virus stocks.
6. Using P3 virus to infect High 5 insect cells, typically for 72 hours.

In one embodiment, infected High 5 cells are grown for 3 days at 27° C.

The supernatant is typically then collected and run on an SDS-PAGE gel. Recombinant proteins can be detected by Western blot, for example using anti-tetra-His antibody (Qiagen) and anti-mouse HRP (Sigma).

The invention will now be described by way of reference to the following Examples which are present for the purposes of illustration only and are not to be construed as being limiting on the present invention. Reference is also made in the Examples to the following drawings in which:

FIG. 5 shows the sequences of the protein cleavage sites of MMP1, MMP2, MMP3, MMP7, MMP8, MMP9 and MMP10.

FIG. 8 shows: (A) and (B) histological staining of the right paw; (C) and (D) 1-11E staining of cartilage in the paw; (E) staining with a non-relevant scFv; all in a mouse RA model.

FIG. 10 shows the construction of (A) an IFN-β/1-11E fusion protein; and (B) a TNFR2Fc/scFv fusion protein.

FIG. 12 is a Western blot of the IFN-β/1-11E fusion protein.

FIG. 13 is a Western blot of (A) and (B) TNFR2Fc/1-11E fusion proteins; (C) a TNFR2Fc/C7 fusion protein

EXAMPLE 1: PREPARATION AND MODIFICATION OF CII

Figure 1:
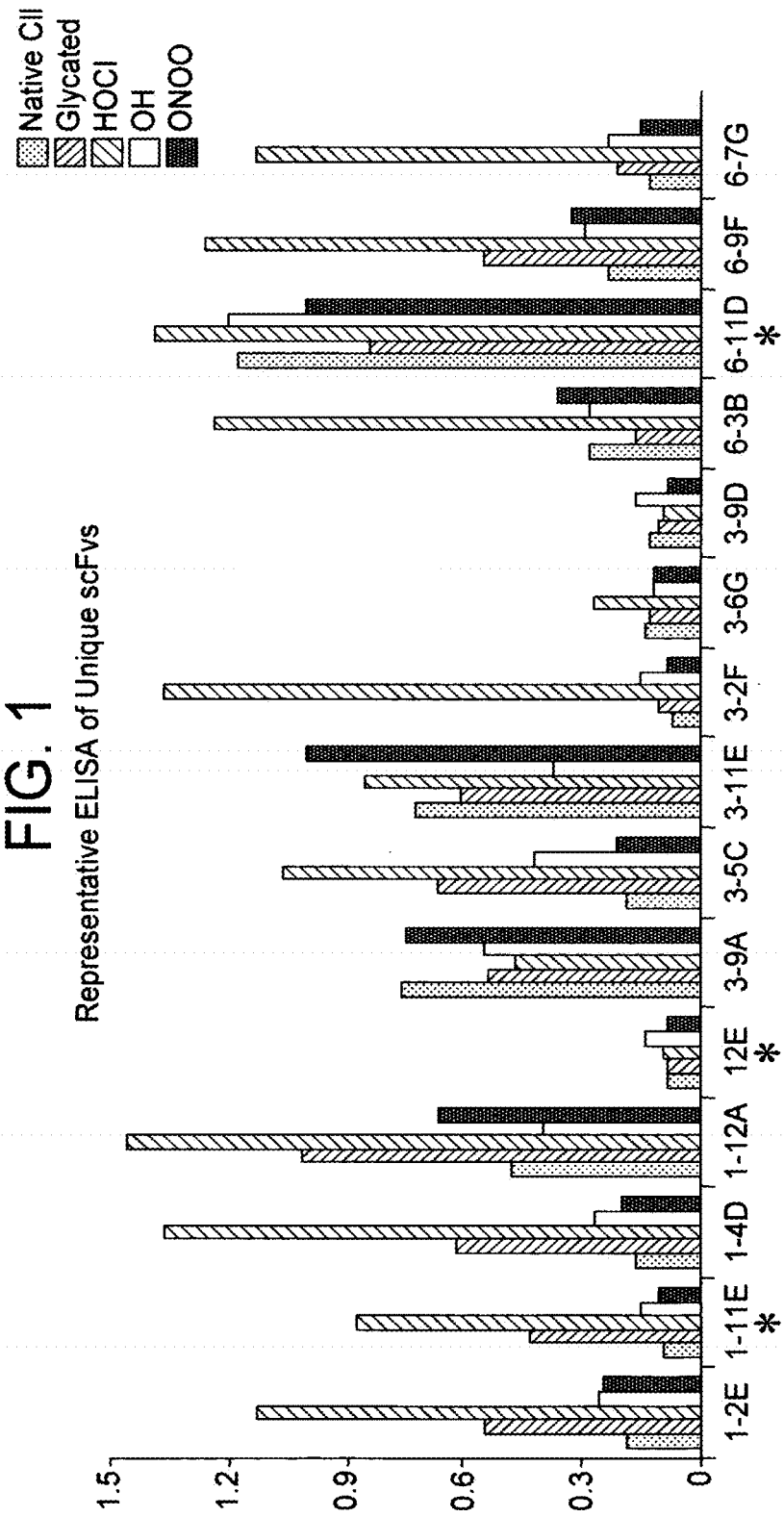
FIG. 1 shows representative ELISA of unique scFvs

CII was prepared from bovine cartilage as in Miller (Miller, Biochemistry 11(26): 4903-4909, 1972) and subsequently exposed to reactive oxygen generating systems as previously described (Nissim A, 2005). Briefly, CII was modified with (.OH), HOCl (Hawkins CL, 2001; Hawkins CL, 2002), (ONOO$^-$), or 2M ribose by ON incubation at 37° C. Bovine serum albumin (BSA, Sigma) was also modified as above and was used as control antigen.

EXAMPLE 2: SELECTION OF ANTI-MODIFIED CII SCFV FROM PHAGE-DISPLAY LIBRARY

Phage display antibody technology (Winter G et al, Annu. Rev. Immunol. 12: 433-455, 1994) was used to raise a single chain fragment variable (scFv) that binds only to CII that has been post-translationally modified by free radicals.

A human semi-synthetic scFv library constructed from a single human framework for $V_H$ (DP-47 and JH4) and $V_L$ (DPK9 and JK1) was employed, in which diversity was incorporated in CDR3 and CDR2 (de Wildt R. M et al, Nat. Biotechnol. 18(9): 989-994, 2000). To select for phage binding to modified CII and not to native non-modified CII, subtractive selection was performed using native non-modified CII for subtraction. HOCl modified CII was used as a target for panning as binding to HOCl modified CII was strongest in RA sera (Nissim A, 2005). Glycated CII was used in parallel. Briefly, immunotubes (Nunc-Immuno Tubes, Maxi-Sorp, Nunc, Denmark) were coated with 10 μg/ml CII in phosphate-buffered saline (PBS). After blocking with 2% marvel in PBS (MPBS) coated tubes were exposed for 2 hours to $10^{13}$ transforming units (tu) of the phage library in 2% MPBS. Unbound phage were then transferred to a second immunotube previously coated with HOCl or ribose-modified CII for a further 2 hours incubation at room temperature. Modified CII-bound phage were then used to infect *E. coli* TG-1 and rescued by helper phage as described (Harrison J. L, 1996). The panning process was repeated three times and *E coli* TG-1 was infected with the final phage eluted after the third round and individual ampicillin-resistant colonies (phage clones) were selected for further analysis.

EXAMPLE 3: SCREENING AND SEQUENCING OF MODIFIED CII-SPECIFIC PHAGE CLONES

Screening for positive anti-modified CII phage clones was first performed by enzyme-linked immunosorbent assay (ELISA), as previously described (Harrison J. L, 1996). Microtiter plate (Nunc, Paisley, UK) wells were coated with 10 μg/ml native or modified CII and incubated with 100 μl phage suspension for 90 minutes. In addition, native and modified BSA were used as negative control. After removal of the supernatants, the amount of bound phage was determined using peroxidase-labeled anti-M13 antibodies (GE Healthcare Little Chalfont, Buckinghamshire) and developed by using 100 mM 3,3'5,5' tetramethylbenzidine (TMB) as substrate. The reaction was monitored in an ELISA reader at 450 nm with a reference wavelength of 650 nm using GENios plate reader (TECAN, Theale Court, Reading UK) and Magellan software (TECAN, Theale Court, Reading UK)

The entire scFv DNA fragment of each modified CII bound phage clone was sequenced using the primers LMB-3 (5'-C AGGAAACAGCTATGAC) (SEQ ID NO: 127) and Fd-Seq (5'-GAATTTTCTGTATGAGG) (SEQ ID NO: 128). Sequences were analyzed using Chromas (Technelysium Pty Ltd) and VBASE (http://vbase.mrc-cpe.cam.ac.uk), to identify unique scFv sequences as shown in Table 3.

TABLE 3

| Clone | Antigen | CDRH2 | CDRH3 | CDRL2 | CDRL3 |
|---|---|---|---|---|---|
| 3-11A | HOCl-CII | DISSTGSYTAYADSVKG (SEQ ID NO: 1) | GAGSFDY (SEQ ID NO: 39) | AASALQS (SEQ ID NO: 61) | QQSSSTPTT (SEQ ID NO: 86) |
| 6-6E | HOCl-CII | AISAAGTATAYADSVKG (SEQ ID NO: 2) | GYDTFDY (SEQ ID NO: 40) | AASSLQS (SEQ ID NO: 62) | QQNYGYPNT (SEQ ID NO: 87) |
| 1-7G | Ribose-CII | SISNSGSYTDYADSVKG (SEQ ID NO: 3) | GYGSFDY (SEQ ID NO: 41) | AASTLQS (SEQ ID NO: 63) | QQANSSPDT (SEQ ID NO: 88) |
| 3-7B | HOCl-CII | SINNYGSNTAYADSVKG (SEQ ID NO: 4) | GYSSFDY (SEQ ID NO: 42) | AASYLQS (SEQ ID NO: 64) | QQTSSSPDT (SEQ ID NO: 89) |
| 6-9D | HOCl-CII | SINNYGSNTAYADSVKG (SEQ ID NO: 4) | GYSSFDY (SEQ ID NO: 42) | AASYLQS (SEQ ID NO: 64) | QQTSSSPDT (SEQ ID NO: 89) |
| 1-1C | Ribose-CII | ISISISYTGNSTDYADSVKG (SEQ ID NO: 5) | GYTAFDY (SEQ ID NO: 43) | YASYLQS (SEQ ID NO: 65) | QQADSTPTT (SEQ ID NO: 90) |
| 1-8D | Ribose-CII | ISISISYTGNSTDYADSVKG (SEQ ID NO: 5) | GYTAFDY (SEQ ID NO: 43) | YASYLQS (SEQ ID NO: 65) | QQADSTPTT (SEQ ID NO: 90) |

TABLE 3-continued

| Clone | Antigen | CDRH2 | CDRH3 | CDRL2 | CDRL3 |
|---|---|---|---|---|---|
| 1-3G | Ribose-CII | SISISYTGNSTDYADSVKG (SEQ ID NO: 5) | GYTAFDY (SEQ ID NO: 43) | YASYLQS (SEQ ID NO: 65) | QQADSTPTT (SEQ ID NO: 90) |
| 4-12C | Ribose-CII | SISISYTGNSTDYADSVKG (SEQ ID NO: 5) | GYTAFDY (SEQ ID NO: 43) | YASYLQS (SEQ ID NO: 65) | QQADSTPTT (SEQ ID NO: 90) |
| 6-3E | HOCl-CII | SISYTGNSTDYASVKG (SEQ ID NO: 5) | GYTAFDY (SEQ ID NO: 43) | YASYLQS (SEQ ID NO: 65) | QQADSTPTT (SEQ ID NO: 90) |
| 6-9A | HOCl-CII | NIATDGTTTYYADSVKG (SEQ ID NO: 6) | NSTYFDY (SEQ ID NO: 44) | SASTLQS (SEQ ID NO: 66) | QQAATSPTT (SEQ ID NO: 91) |
| 1-12A | Ribose-CII | SISISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| 4-6A | Ribose-CII | SISISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| 4-8A | Ribose-CII | SISISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| 4-9F | Ribose-CII | SISISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| 4-4H | Ribose-CII | SISISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| 3-3A | HOCl-CII | SISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| 3-6F | HOCl-CII | SISNSGTNTDYADSVKG (SEQ ID NO: 7) | NYASFDY (SEQ ID NO: 45) | YASYLQS (SEQ ID NO: 65) | QQGSASPST (SEQ ID NO: 92) |
| 6-10H | HOCl-CII | SISYTGDSTYYADSVKG (SEQ ID NO: 8) | NYSAFDY (SEQ ID NO: 46) | YASYLQS (SEQ ID NO: 65) | QQADSTPTT (SEQ ID NO: 90) |
| 12E | Unknown | SINDSGITTYYADSVKG (SEQ ID NO: 9) | NYSAFDY (SEQ ID NO: 46) | AASDLQS (SEQ ID NO: 67) | QQSDSAPTT (SEQ ID NO: 93) |
| 3-5G | HOCl-CII | SIDSAGASTYYADSVKG (SEQ ID NO: 10) | NYSAFDY (SEQ ID NO: 46) | NASSLQS (SEQ ID NO: 68) | QQSDTYPST (SEQ ID NO: 94) |
| 3-4D | HOCl-CII | SISYTGDSTYYADSVKG (SEQ ID NO: 8) | NYSAFDY (SEQ ID NO: 46) | TASNLQS (SEQ ID NO: 69) | QQSYASPTT (SEQ ID NO: 95) |
| 3-5D | HOCl-CII | SISYTGDSTYYADSVKG (SEQ ID NO: 8) | NYSAFDY (SEQ ID NO: 46) | TASNLQS (SEQ ID NO: 69) | QQSYASPTT (SEQ ID NO: 95) |
| 6-4E | HOCl-CII | SISYTGDSTYYADSVKG (SEQ ID NO: 8) | NYSAFDY (SEQ ID NO: 46) | TASNLQS (SEQ ID NO: 69) | QQTGSYPTT (SEQ ID NO: 96) |
| 3-6B | HOCl-CII | SINATGYGTYYADSVKG (SEQ ID NO: 11) | NYSDFDY (SEQ ID NO: 47) | SASALQS (SEQ ID NO: 70) | QQGDSYPTT (SEQ ID NO: 97) |
| 3-6G | HOCl-CII | SINSNGTDTYYADSVKG (SEQ ID NO: 12) | NYSDFDY (SEQ ID NO: 47) | TASALQS (SEQ ID NO: 71) | QQGYGAPTT (SEQ ID NO: 98) |

TABLE 3-continued

| Clone | Antigen | CDRH2 | CDRH3 | CDRL2 | CDRL3 |
|---|---|---|---|---|---|
| 4-11F | Ribose-CII | SISISATGSSTYYADSVKG (SEQ ID NO: 13) | NYSDFDY (SEQ ID NO: 47) | SASDLQS (SEQ ID NO: 72) | QQSSYTPTT (SEQ ID NO: 99) |
| 6-7H | HOCl-CII | SISATGSSTYYADSVKG (SEQ ID NO: 13) | NYSDFDY (SEQ ID NO: 47) | SASDLQS (SEQ ID NO: 72) | QQSSYTPTT (SEQ ID NO: 99) |
| 1-11E | Ribose-CII | SISIDDSGATTYYADSVKG (SEQ ID NO: 14) | NYSSFDY (SEQ ID NO: 48) | YASSLQS (SEQ ID NO: 73) | QQAANYPTT (SEQ ID NO: 100) |
| 1-2F | Ribose-CII | SISIDDSGATTYYADSVKG (SEQ ID NO: 14) | NYSSFDY (SEQ ID NO: 48) | YASSLQS (SEQ ID NO: 73) | QQAANYPTT (SEQ ID NO: 100) |
| 1-6H | Ribose-CII | SISIDDSGATTYYADSVKG (SEQ ID NO: 14) | NYSSFDY (SEQ ID NO: 48) | YASSLQS (SEQ ID NO: 73) | QQAANYPTT (SEQ ID NO: 100) |
| 3-8D | HOCl-II | SIDDSGATTYYADSVKG (SEQ ID NO: 14) | NYSSFDY (SEQ ID NO: 48) | YASSLQS (SEQ ID NO: 73) | QQAANYPTT (SEQ ID NO: 100) |
| 1-4D | Ribose-CII | SISIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| 4-2F | Ribose-CII | SISIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| 3-3B | HOCl-CII | SIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| 3-5C | HOCl-CII | SIASTGDSTYYADSVKG (SEQ ID NO: 15 ) | NYSSFDY (SEQ ID NO: 48) | SASALQS (SEQ ID NO: 70) | QQASNYPTT (SEQ ID NO: 101) |
| 6-9C | HOCl-CII | SIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| 4G | Unknown | SIASTGDSTYYADSVKG (SEQ ID NO: 15) | NYSSFDY (SEQ ID NO: 48) | SASALQS (SEQ ID NO: 70) | QQASNYPTT (SEQ ID NO: 101) |
| 3-12F | HOCl-CII | SISTNGSSTYYADSVKG (SEQ ID NO: 16) | NYSSFDY (SEQ ID NO: 48) | DASGLQS (SEQ ID NO: 74) | QQGDTSPTT (SEQ ID NO: 102) |
| 3-4G | HOCl-CII | SISTNGSSTYYADSVKG (SEQ ID NO: 16) | NYSSFDY (SEQ ID NO: 48) | DASGLQS (SEQ ID NO: 74) | QQGDTSPTT (SEQ ID NO: 102) |
| 6-11F | HOCl-CII | SISTNGSSTYYADSVKG (SEQ ID NO: 16) | NYSSFDY (SEQ ID NO: 48) | DASGLQS (SEQ ID NO: 74) | QQGDTSPTT (SEQ ID NO: 102) |
| 6-11H | HOCl-CII | SISTNGSSTYYADSVKG (SEQ ID NO: 16) | NYSSFDY (SEQ ID NO: 48) | DASGLQS (SEQ ID NO: 74) | QQGDTSPTT (SEQ ID NO: 102) |
| 3-2C | HOCl-CII | SIDTTGTTTYFADSVKG (SEQ ID NO: 17) | NYSSFDY (SEQ ID NO: 48) | SASYLQS (SEQ ID NO: 75) | QQGYSAPTT (SEQ ID NO: 103) |
| 5B | Unknown | TISYSGNNTYYADSVKG (SEQ ID NO: 18) | NYSSFDY (SEQ ID NO: 48) | TASSLQS (SEQ ID NO: 76) | QQGYTSPTT (SEQ ID NO: 104) |
| 6-10G | HOCl-CII | SIDAGGNGTYYADSVKG (SEQ ID NO: 19) | NYSSFDY (SEQ ID NO: 48) | TASNLQS (SEQ ID NO: 77) | QQNNYYPTT (SEQ ID NO: 105) |

TABLE 3-continued

| Clone | Antigen | CDRH2 | CDRH3 | CDRL2 | CDRL3 |
|---|---|---|---|---|---|
| 1-4H | Ribose-CII | SIDAGGNGTYYADSVKG (SEQ ID NO: 19) | NYSSFDY (SEQ ID NO: 48) | YASSLQS (SEQ ID NO: 73) | QQSDAYPTT (SEQ ID NO: 106) |
| 4-5A | HOCl-CII | SIDAGGNGTYYADSVKG (SEQ ID NO: 19) | NYSSFDY (SEQ ID NO: 48) | YASSLQS (SEQ ID NO: 73) | QQSDAYPTT (SEQ ID NO: 106) |
| 4-1B | HOCl-CII | SIDAGGNGTYYADSVKG (SEQ ID NO: 19) | NYSSFDY (SEQ ID NO: 48) | YASSLQS (SEQ ID NO: 73) | QQSDAYPTT (SEQ ID NO: 106) |
| 4-12D | HOCl-CII | SIDAGGNGTYYADSVKG (SEQ ID NO: 19) | NYSSFDY (SEQ ID NO: 48) | YASSLQS (SEQ ID NO: 73) | QQSDAYPTT (SEQ ID NO: 106) |
| 6-4B | HOCl-CII | SIDSAGNATYYADSVKG (SEQ ID NO: 20) | NYSSFDY (SEQ ID NO: 48) | AASTLQS (SEQ ID NO: 78) | TSNYPTTQQ (SEQ ID NO: 107) |
| 1-2E | Ribose-CII | SIISITDSGDTTYYADSVKG (SEQ ID NO: 21) | NYSTFDY (SEQ ID NO: 49) | SASSLQS (SEQ ID NO: 79) | QQSNATPTT (SEQ ID NO: 108) |
| 1-7F | Ribose-CII | SIISITDSGDTTYYADSVKG (SEQ ID NO: 21) | NYSTFDY (SEQ ID NO: 49) | SASSLQS (SEQ ID NO: 79) | QQSNATPTT (SEQ ID NO: 108) |
| 1-10F | Ribose-CII | SIISITDSGDTTYYADSVKG (SEQ ID NO: 21) | NYSTFDY (SEQ ID NO: 49) | SASSLQS (SEQ ID NO: 79) | QQSNATPTT (SEQ ID NO: 108) |
| 1-9G | Ribose-CII | SIISITDSGDTTYYADSVKG (SEQ ID NO: 21) | NYSTFDY (SEQ ID NO: 49) | SASSLQS (SEQ ID NO: 79) | QQSNATPTT (SEQ ID NO: 108) |
| 4-1C | Ribose-CII | SIISITDSGDTTYYADSVKG (SEQ ID NO: 21) | NYSTFDY (SEQ ID NO: 49) | SASSLQS (SEQ ID NO: 79) | QQSNATPTT (SEQ ID NO: 108) |
| 6-7G | HOCl-CII | SIATTGDNTYYADSVKG (SEQ ID NO: 22) | NYSYFDY (SEQ ID NO: 50) | TASTLQS (SEQ ID NO: 80) | QQAAGNPTT (SEQ ID NO: 109) |
| 3-7H | HOCl-CII | AINAYGGSTYYADSVKG (SEQ ID NO: 23) | NYSYFDY (SEQ ID NO: 50) | AASSLQS (SEQ ID NO: 62) | QQGSDYPTT (SEQ ID NO: 110) |
| 6-1F | HOCl-CII | AINAYGGSTYYADSVKG (SEQ ID NO: 23) | NYSYFDY (SEQ ID NO: 50) | AASSLQS (SEQ ID NO: 62) | QQGSDYPTT (SEQ ID NO: 110) |
| 6-3B | HOCl-CII | SIATTGTSTTYYADSVKG (SEQ ID NO: 24) | NYSYFDY (SEQ ID NO: 50) | TASSLQS (SEQ ID NO: 76) | QQGSTAPTT (SEQ ID NO: 111) |
| 4H | Unknown | SIATTGTSTTYYADSVKG (SEQ ID NO: 24) | NYSYFDY (SEQ ID NO: 50) | TASSLQS (SEQ ID NO: 76) | QQGSTAPTT (SEQ ID NO: 111) |
| 3-9A | HOCl-CII | TIDTAGSYTDYADSVKG (SEQ ID NO: 25) | NYSYFDY (SEQ ID NO: 50) | GASTLQS (SEQ ID NO: 81) | QQSTASPST (SEQ ID NO: 112) |
| 6-10D | HOCl-CII | SISNNGSSTYYADSVKG (SEQ ID NO: 26) | NYSYFDY (SEQ ID NO: 50) | AASNLQS (SEQ ID NO: 82) | QQTSSYPTT (SEQ ID NO: 113) |
| 3-5H | HOCl-CII | SIAYGGAGTDYADSVKG (SEQ ID NO: 27) | NYTAFDY (SEQ ID NO: 51) | AASYLQS (SEQ ID NO: 64) | QQGAGSPST (SEQ ID NO: 114) |
| 3-2F | HOCl-CII | AIANTGSATNYADSVKG (SEQ ID NO: 28) | NYTAFDY (SEQ ID NO: 51) | DASTLQS (SEQ ID NO: 83) | QQRNTSPTT (SEQ ID NO: 115) |

TABLE 3-continued

| Clone | Antigen | CDRH2 | CDRH3 | CDRL2 | CDRL3 |
|---|---|---|---|---|---|
| 1-6G | Ribose-CII | SISISTAGTYTDYADSVKG (SEQ ID NO: 29) | NYTDFDY (SEQ ID NO: 52) | SASYLQS (SEQ ID NO: 75) | QQSNTSPAT (SEQ ID NO: 116) |
| 3-11H | HOCl-CII | SISTAGTYTDYADSVKG (SEQ ID NO: 29) | NYTDFDY (SEQ ID NO: 52) | SASYLQS (SEQ ID NO: 75) | QQSNTSPAT (SEQ ID NO: 116) |
| 6-9F | HOCl-CII | SINDTGYTTYYADSVKG (SEQ ID NO: 30) | NYTYFDY (SEQ ID NO: 53) | TASTLQS (SEQ ID NO: 80) | QQAYTAPTT (SEQ ID NO: 117) |
| 3-9D | HOCl-CII | SIASSGTTTYYADSVKG (SEQ ID NO: 31) | SYADFDY (SEQ ID NO: 54) | AASNLQS (SEQ ID NO: 82) | QQADTYPTT (SEQ ID NO: 118) |
| 4-3H | Ribose-CII | IITITSTGAATAYADSVKG (SEQ ID NO: 32) | SYATFDY (SEQ ID NO: 55) | AASYLQS (SEQ ID NO: 64) | QQAANSPDT (SEQ ID NO: 119) |
| 3-3E | HOCl-CII | AIDGTGYGTAYADSVKG (SEQ ID NO: 33) | SYDTFDY (SEQ ID NO: 56) | GASSLQS (SEQ ID NO: 84) | QQTSDYPNT (SEQ ID NO: 120) |
| 3-10C | HOCl-CII | SIANAGTATYYADSVKG (SEQ ID NO: 34) | SYSNFDY (SEQ ID NO: 57) | SASTLQS (SEQ ID NO: 66) | QQASTSPTT (SEQ ID NO: 121) |
| 3-11E | HOCl-CII | SIDSAGDSTYYADSVKG (SEQ ID NO: 35) | SYSYFDY (SEQ ID NO: 58) | TASYLQS (SEQ ID NO: 85) | QQASDYPTT (SEQ ID NO: 122) |
| 6-8C | HOCl-CII | SISSSGDTTYYADSVKG (SEQ ID NO: 36) | SYSYFDY (SEQ ID NO: 58) | TASTLQS (SEQ ID NO: 80) | QQSSSNPTT (SEQ ID NO: 123) |
| 6-11D | HOCl-CII | SIDTGGSYTDYADSVKG (SEQ ID NO: 37) | SYTTFDY (SEQ ID NO: 59) | SASYLQS (SEQ ID NO: 75) | QQGSNSPTT (SEQ ID NO: 124) |
| 4-5H | Ribose-CII | SIDTGGSYTDYADSVKG (SEQ ID NO: 37) | SYTTFDY (SEQ ID NO: 59) | SASYLQS (SEQ ID NO: 75) | QQGSNSPTT (SEQ ID NO: 124) |
| 6-5F | HOCl-CII | SIDTGGSYTDYADSVKG (SEQ ID NO: 37) | SYTTFDY (SEQ ID NO: 59) | SASYLQS (SEQ ID NO: 75) | QQGSNSPTT (SEQ ID NO: 124) |
| 6-7F | HOCl-CII | SIDTGGSYTDYADSVKG (SEQ ID NO: 37) | SYTTFDY (SEQ ID NO: 59) | SASYLQS (SEQ ID NO: 75) | QQGSNSPTT (SEQ ID NO: 124) |
| 1-10D | Ribose-CII | IISIDASGANTAYADSVKG (SEQ ID NO: 38) | TYGTFDY (SEQ ID NO: 60) | SASYLQS (SEQ ID NO: 75) | QQSATTPDT (SEQ ID NO: 125) |

EXAMPLE 4: PRODUCTION AND PURIFICATION OF ANTI-MODIFIED CII-SCFV

The reactive phage clones obtained from *E coli* TG-1 bacteria were used to infect *E coli* HB2151 non-suppressor bacterial strain to obtain soluble scFv. After overnight induction with 1 mM IPTG at 30° C., the antibody fragments, derived from the $V_H3$ family, were harvested from the supernatant and periplasmic space as described (Harrison J. L, 1996) and purified on a protein A affinity column (GE Healthcare Ltd, Little Chalfont, Buckinghamshire). Binding of purified scFv to modified CII was first analyzed by ELISA as above except that mouse anti-myc tag antibody (Santa Cruz Biotechnology, INC, Wembley, UK) followed by anti-mouse-HRP conjugate (Sigma, Dorset, UK) were used to probe bound scFv.

Anti-Modified CII scFv Raised by Phage Display Human Antibody Library

After three rounds of subtractive selection 82 phage clones specific to either glycated CII or HOCl modified CII were selected out of which 42 clones had unique sequences. 15 representative clones with different binding patterns but with good expression were then studied for further analysis (FIG. 1 and Table 1). As shown in FIG. 1, out of these 15 clones there were 9 clones with stronger binding to modified CII, 3 clones bound to all forms of CII and and 3 clones had no binding reactivity to any form of CII. Three scFvs that have different binding characteristics were then further studied: Clone 1-11E binds to modified CII (glycated, HOCl and to some extent to peroxynitrated CII), clone 6-11D binds to both native and modified CII and clone 12E that does not bind to any form of CII. None of these scFv bound to native or free radical modified BSA, or to collagen type III (data not shown).

EXAMPLE 5: WESTERN BLOTTING

Western blot using scFv as probe and modified or native CII as target antigens was done as described (Nissim A, 2005). Briefly, modified and native CII (2 µg of each) were run on a 7.5% denaturing SDS gel and electroblotted into a nitrocellulose membrane. After blocking with 2% MPBS, membranes were incubated with 10 µg/ml purified scFv in 2% MPBS for 2 hr at room temperature, followed by incubation with mouse anti-myc tag (Santa Cruz Biotechnology, INC, Wembley, UK) and then with anti-mouse-HRP (Sigma, Dorset). Membranes were washed three times with 0.1% Tween PBS (5 min each) and three times with PBS (5 min each) before development with ECL (GE Healthcare Ltd. Little Chalfont, Buckinghamshire).

Figure 2:
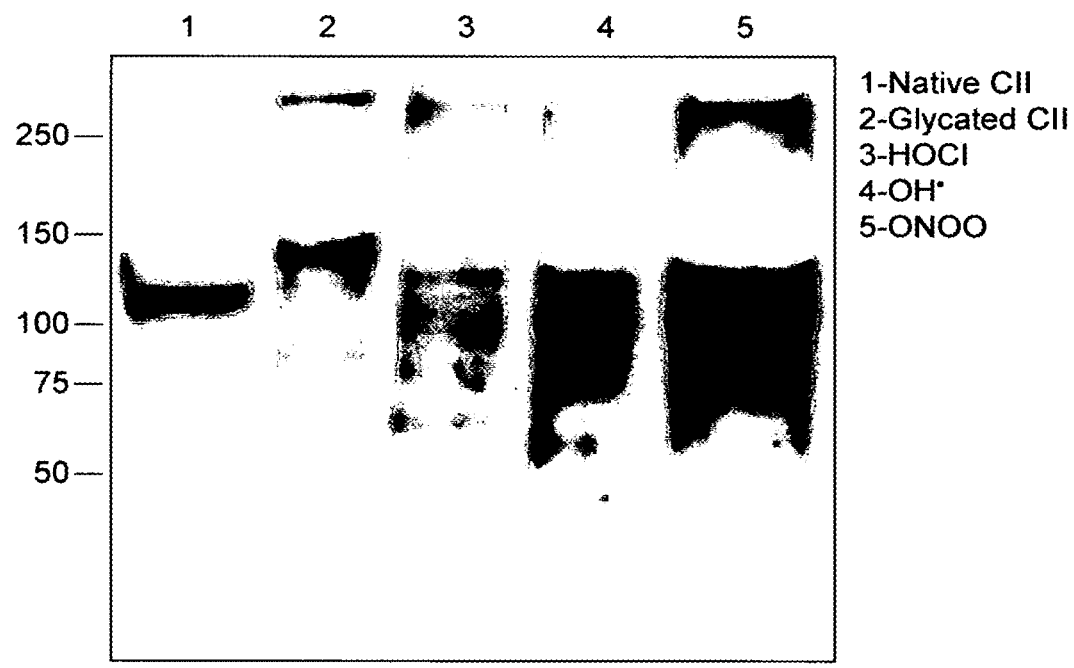
FIG. 2 shows Western Blotting with scFv 1-11E probe

Comparative Analysis of Human RA Serum and scFv Binding to CII by Western Blotting 1-11E binds several CII fragments between 50 and 150 kDa as well as to a band >250 kDa which resulted from CII cross linking due to the ROS reactivity (FIG. 2 lane 2-5). 1-11E also binds to native CII corresponding to a band below 150 KDa (FIG. 2 lane 1). Binding to native CII in Western blotting was also seen in sera from RA patients that did not bind to native CII in ELISA but only to ROS modified CII in ELISA (for example sera 33 (Nissim A, 2005)).

EXAMPLE 6: IMMUNOHISTOCHEMISTRY OF HUMAN OA AND RA CARTILAGE USING SELECTED ANTI-MODIFIED CII SCFV

One osteochondral sample was obtained from the femoral condyle of a patient (female, 63 years old) undergoing prosthetic knee replacement for OA. One sample of normal human cartilage was obtained post-mortem from a preserved area of a knee with unicompartimental OA undergoing joint replacement (female, 54 years old). In both cases, cartilage was fixed overnight at 4° C. in 4% paraformaldehyde, decalcified for 15 days in 0.5M EDTA at 4° C., washed in PBS, and embedded in paraffin according to standard protocols. Safranin 0 staining was performed according to standard protocols (Rosenberg, 1971). All samples were obtained in accordance with institutional policies and regulations.

For immunostaining, 5 mm thick sections were cut, deparaffinized and hydrated according to standard protocols. After endogenous peroxidase quenching in 0.5% hydrogen peroxide for 15 min antigen retrieval was done by 45 min incubation of slides with 3 mg/ml pepsin (Zymed, Chandlers Ford, Hampshire, UK) at 37° C. followed by two washes with PBS. Endogenous avidin activity was blocked using a commercially available kit (Vector Laboratories, Orton Southgate, Peterborough, UK) according to the manufacturer's instructions. This was followed by 30 min blocking with 0.5% BSA Immunostaining was performed using the selected scFv (10 µg/ml and 1 µg/ml) as well as control commercial mouse anti-CII antibodies (diluted 1:100 and 1:1000 dilution; Chemicon International, Chandlers Ford, Hampshire, UK) and polyclonal anti-CII antibodies (diluted 1:100, 1:1000) from collagen induced arthritis (CIA) mice. ScFv or control antibodies were added to the slide in blocking buffer (0.5% BSA in PBS plus 0.05% sodium azide) and left overnight at 4° C. When scFv were used for probing, next day slides were washed with PBS for 2 minutes and incubated for 30 minutes with anti-myc tag mouse antibodies to bind to the myc tag incorporated at the carboxy terminal end of the scFv (diluted 1:200, Santa Cruz Biotechnology Inc, Wembley, UK). After two washes as above anti-mouse biotinylated antibodies were added (Vector kit PK-6102) followed by two washes with PBS and development with DAB substrate (DAKO, Ely, Cambridgeshire, UK) and nuclear counterstaining with Mayer's haematoxylin. Slides were finally dehydrated and mounted with DPX mount (BDH, London, UK)

Figure 3:
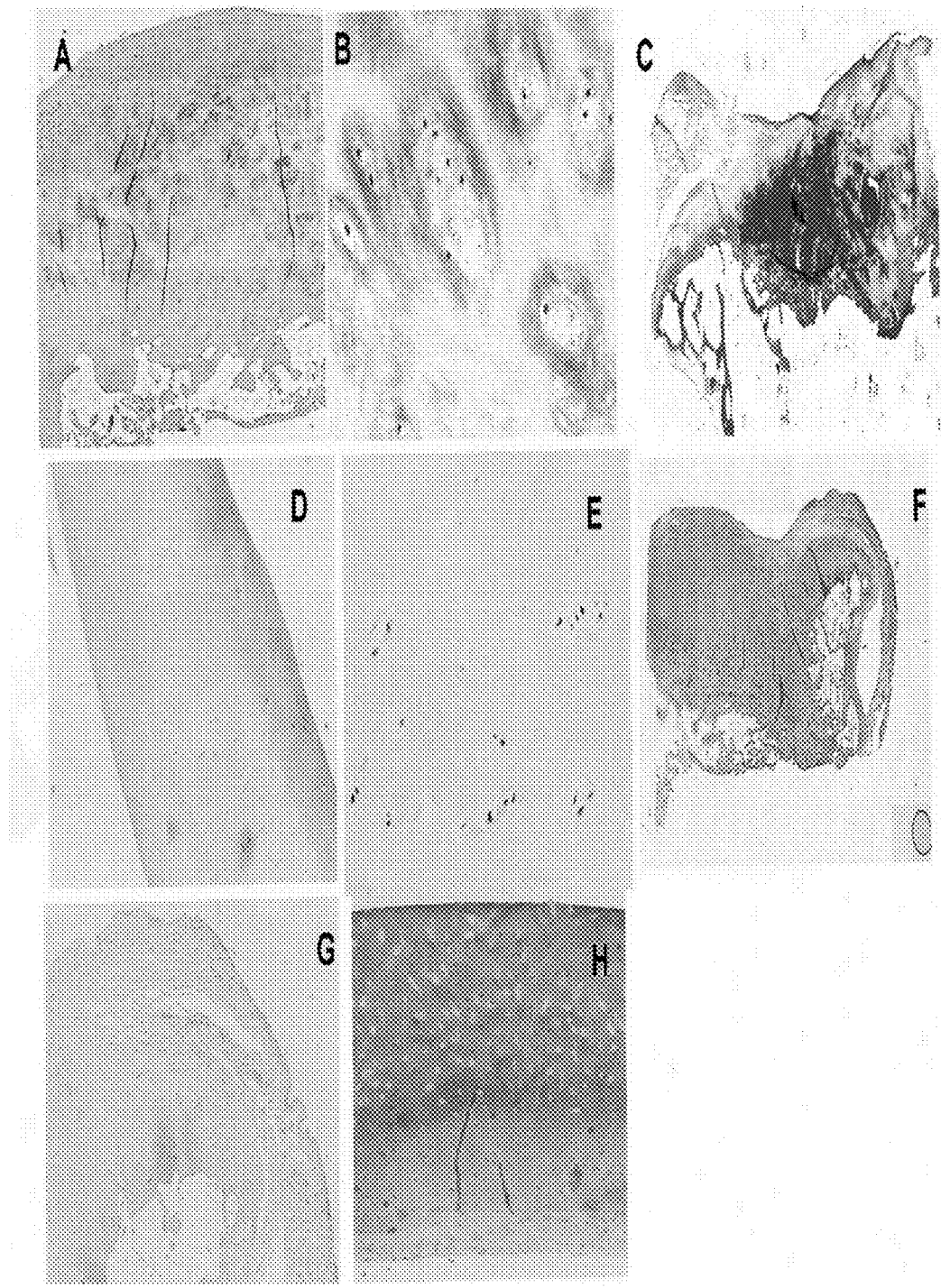
FIG. 3 shows specific binding to damaged human cartilage tissue by anti-ROS-modified CII scFv in patients with OA in photographs (A) to (H).

Specific Binding to Damaged Human Cartilage Tissue by Anti-ROS-Modified CII scFv The cartilage extracellular matrix is a complex structure where several molecules interact to form a structural and functional unit. There is therefore the chance that the tertiary and quaternary structure of collagens in the intact tissue may alter the specificity of binding of the phage antibodies that had been selected in vitro. To determine binding specificity in the intact tissue, the capacity of anti-ROS-modified CII scFv to bind to CII within the matrix complex structure and to present immunoreactivity with damaged OA cartilage as opposed to normal cartilage was tested. 1-11E stained the extracellular matrix of cartilage tissue that displayed marked features of OA (FIG. 3A, B) with mostly pericellular staining (FIG. 3 B), with severe damage of the extracellular matrix determined with reduced staining with safranin 0 (FIG. 3 C). No staining by scFv 1-11E was detected when using histologically normal cartilage from normal cartilage (FIG. 3 D, E). By contrast, polyclonal antibodies from CIA mice bound the OA cartilage in both the damaged and non-damaged regions strongly (FIG. 3 F) and weakly stained with safranin 0 (FIG. 3 C). A commercial anti-CII mAb did not stain the damaged cartilage areas stained by 1-11E on an adjacent section (FIG. 3 G) but intensely stained a histologically normal cartilage (FIG. 3 H), suggesting that the epitope recognised by the commercial antibody is lost in the OA section.

Figure 6:
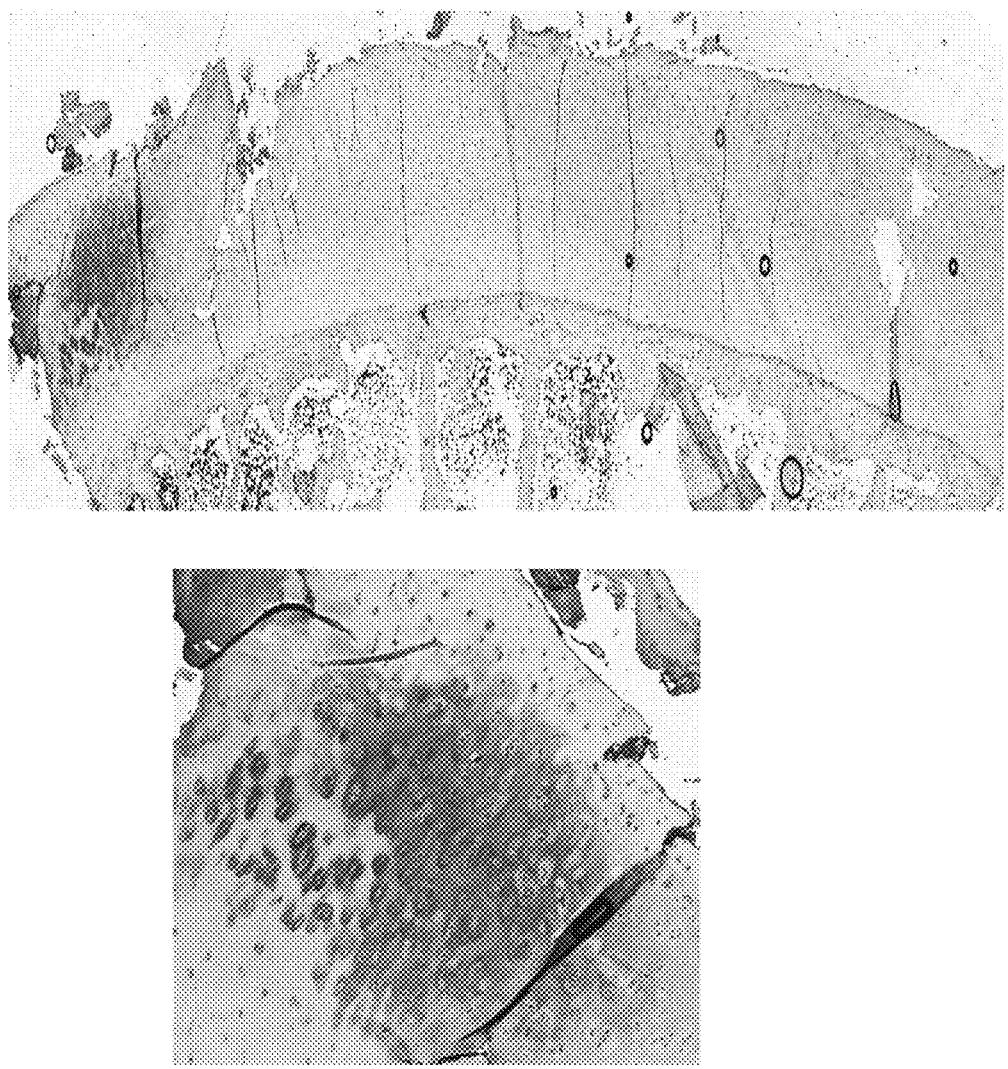
FIG. 6 shows specific binding to damaged human cartilage tissue by anti-ROS-modified CII scFv in patients with OA.

FIG. 6 also shows staining of OA cartilage. Although synovial inflammation in OA is not as extensive as in RA and inflammatory cells are not significant in numbers, low grade synovitis is nearly a constant feature in OA. Abnormal mechanical force appears to stimulate chrondocytes to produce some of the same inflammatory mediators and ROS as the infiltrating leukocytes present in inflamed RA joints, leading to post-translational modifications of CII in OA. FIG. 6 confirms the results shown in FIG. 3 and shows that staining of OA cartilage section is only pericellular, around the chrondocytes.

A further sample was obtained from a patient (female, 47 years old) undergoing total right knee replacement for RA. Fixing and staining protocols were as described above.

Figure 7:
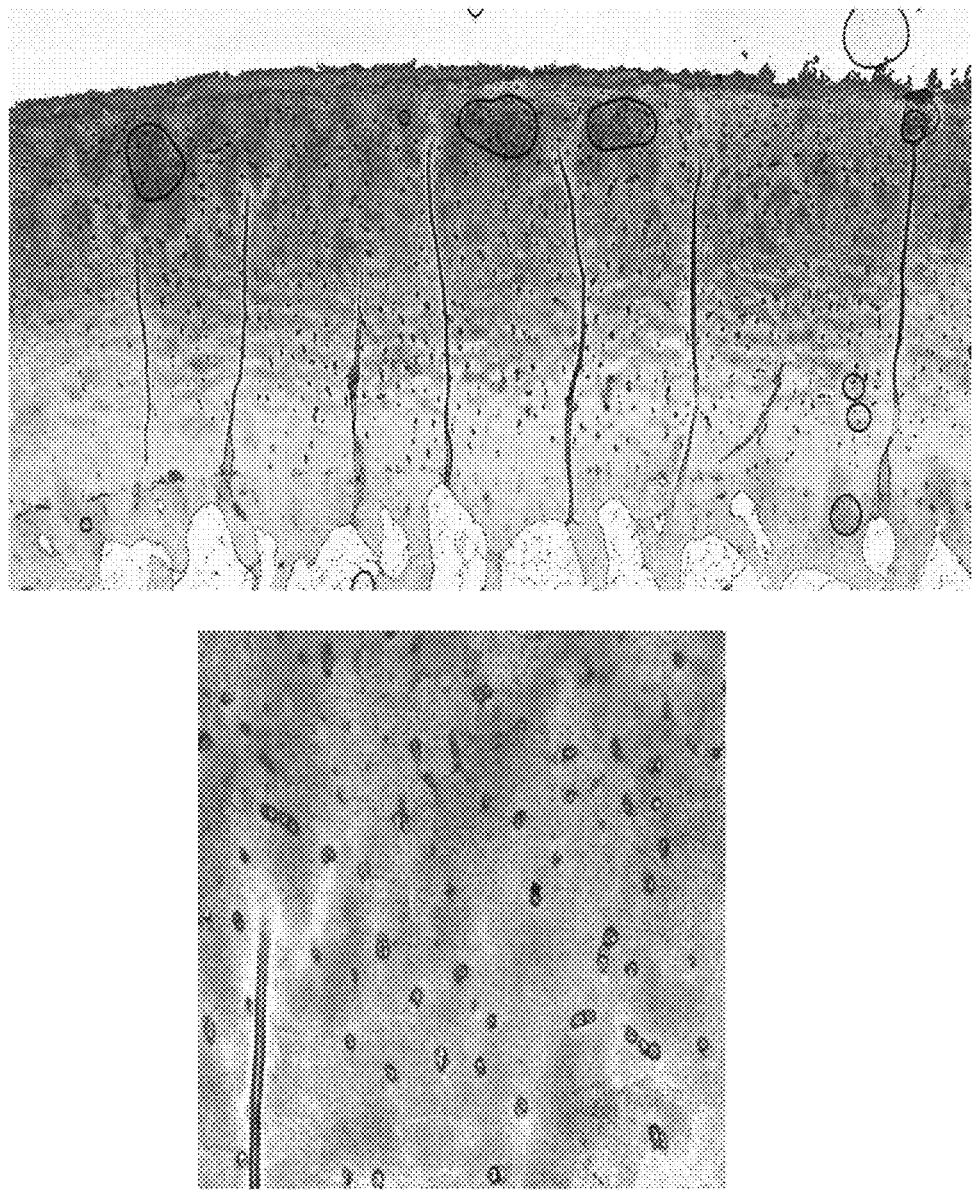
FIG. 7 shows specific binding to damaged human cartilage tissue by anti-ROS-modified CII scFv in patients with RA.

FIG. 7 shows staining of the RA cartilage. In RA, infiltrating inflammatory cells consume increased amounts of oxygen, resulting in the generation of reactive oxygen species (ROS), which may cause excessive degradation of the extracellular matrix leading to cartilage destruction and chemical post-translational modification of CII by ROS. FIG. 7 shows uniteral staining of RA cartilage across the section. This is due to the high influx of immune cells that produce high levels of ROS.

EXAMPLE 7: CONSTRUCTION AND EXPRESSION OF DIABODY

Out of the unique scFv assessed for specific binding to modified CII as well as best expression in bacteria, the most promising scFv, 1-11E of 25 kDa, was engineered to a larger fragment of 55 KDa. The linker between the $V_H$ and $V_L$ was shortened by digesting the phagemid vector with XhoI and SalI and relegation. This results in bivalent diabody, a superior molecule with an increased half life (Hudson, 2005) built from two scFv. Expression and screening of diabody binders was done as above. Molecular weight profile of the resulted expressed diabody was analyzed by gel filtration.

EXAMPLE 8: INDUCING ARTHRITIS IN THE ANIMAL MODELS

Male C3H mice (age 17-19 weeks) were used. 100 mg of dessicated non-viable T.B. strain H37RA (Difco 231141)

was added to 30 ml of incomplete Freunds adjuvant (IFA, Difco 263910) to form complete Freunds adjuvant (CFA). An equal volume of CFA was added to a 2 mg/ml solution (in PBS) of methylated BSA (mBSA) (Sigma A1009). The mixture was then emulsified on ice using an Ultra-Turrax T25 homogeniser at 13500-20500 rpm until a fluffy milky consistency was obtained. Mice were anaesthetised with Hypnorm, and 100 µl of 1 mg/ml (i.e. 100 µg) mBSA in CFA was injected over 2-3 separate sites intradermally. 1 week later, the immunisation was repeated as previously, except that no bacteria were added (i.e. IFA/mBSA). Two weeks after the 2nd immunisation, mice were anaesthetised with nitrous/oxygen and halothane, and inflammation was induced by injecting 50 µl of 1 mg/ml (i.e. 50 µg) mBSA in PBS into the animals' left hind paw. As a control, 50 µl PBS was injected into the right hind paw. Inflammation was measured using calipers to measure the paw thickness. Swelling was seen only in the right paws from 24 hours, and persisted until 1 week later. 2 weeks later, the swelling had totally subsided.

EXAMPLE 9: IMAGING OF ANTI-ROS MODIFIED CII LOCALIZATION

50 µg of 1-11E diabody was radiolabelled with 20 MBq of sodium [I-125] iodide (GE Healthcare, Amersham, UK) using the iodogen method (Perbio Science, Cramlingham, UK) and diluted in PBS to a final volume of 240 µl. Radiochemical purity was determined by thin-layer chromatography on silica gel (ITLC, Pall Corporation, Portsmouth, UK) using 85% methanol as mobile phase. A volume of 100 µl of the labeled diabody was injected intravenously via the tail vein into two arthritis-bearing C3H mice 24 hours after injection of the mBSA. Four and 22 hours later the mice were anaesthetized by ip injection of Ketamine/Xylazine. The mice were imaged on a NanoSPECT/CT scanner (Bioscan Inc, Washington, USA) using a four-detector/36x 1.4 mm pinhole configuration. 30-50,000 counts were acquired for the SPECT study over 20-50 minutes.

Imaging of 1-11E Localisation into the Inflamed Paw

Figure 4:
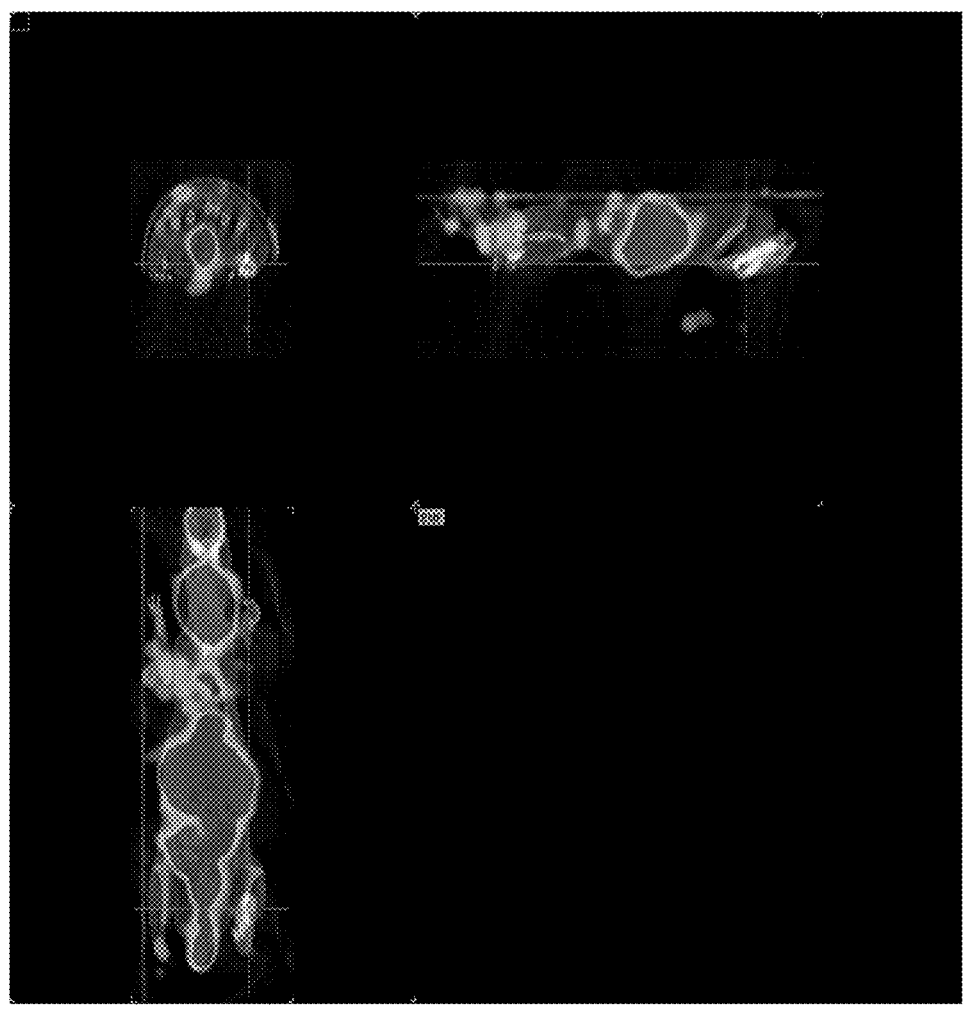
FIG. 4 shows the localisation of scFv 1-11E in inflamed paw.

SPECT and CT images from the NanoSPECT/CT camera were fused and displayed using PMOD software. FIG. 4 shows a representative image acquired 22 hours after injection of the radiotracer. Increased uptake of radioactivity is clearly seen in the rear left (inflamed) paw relative to the right (normal paw).

EXAMPLE 10: STAINING OF CARTILAGE IN MOUSE RA MODEL

Staining of cartilage was observed in the mouse mBSA model described in Example 8 above, except that C57BL mice were used.

Mice were sensitised with mBSA (100 µg) in CFA intradermally at the base of the tail, and challenged either intra-articularly (both knees) or intra-plantarly (right, saline left) with 500 µg mBSA in saline 14 days later.

Staining of cartilage is shown in FIG. 8.

Paw:

12 hours post challenge with mBSA, the right paw was grossly inflamed in the subplantar region (seen by haematoxylin and eosin (H&E) staining), as shown in FIGS. 8A and 8B. The cartilage in the mBSA paws is uniformly and strongly stained by 1-11E, as shown in FIGS. 8C and 8D. The left paw injected by saline had no subplantar inflammation. Some cartilage within the left paw joints was stained heterogeneously, perhaps associated with spontaneous osteoarthritis.

EXAMPLE 11: STAINING OF JOINT IN MOUSE OA MODEL

Staining was observed in mice with joint surface injury.

Seven week old C57BL/6 male mice were utilized for these experiments (Dell'Accio F et al, Arthritis Res Ther. 2006; 8(5):R139). The mice were anesthetized and subjected to medial para-patellar arthrotomy. The patellar groove was exposed by lateral patellar dislocation. A longitudinal full thickness injury was made in the patellar groove using a custom made device in which the length of a 26G needle was limited by a glass bead (injured knee). The patellar dislocation was then reduced and the joint capsule and the skin sutured in separate layers. The animals were killed after 4 weeks and the knees dissected for histological and histochemical analysis.

Staining methods are as set out in Example 6 above, except that rabbit anti-myc followed by anti-rabbit-HRP were used to avoid cross-reactivity with mouse antibody in the tissue.

Figure 9:
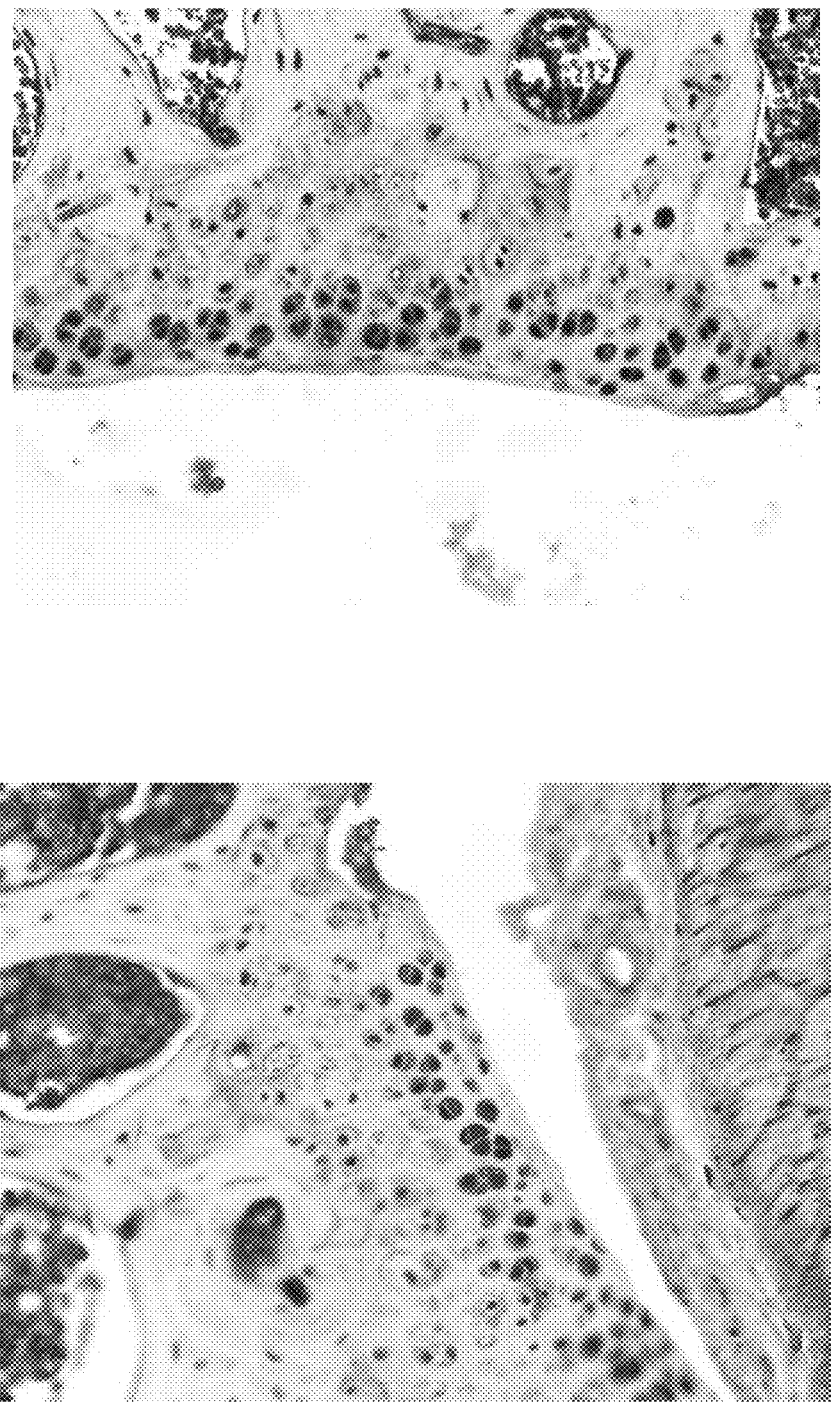
FIG. 9 shows staining of a joint surface injury in a mouse OA model.

As shown in FIG. 9, there is strong staining at the site of the injury.

EXAMPLE 12: PRODUCTION OF FUSION PROTEINS: 1-11E WITH ANTI-INFLAMMATORY CYTOKINES

Cloning of IFN-Beta/1-11E pFastBac1.AH was created from pFastBac1 (Invitrogen) by cutting out BamHI/HindIII fragment containing multiple cloning sites (MCS), and replacing with a linker to give another MCS of BamHI-KpnI-HindIII-ApaI.

Mouse interferon b (mIFNb) was cloned into the HindIII-EcoRI sites, followed by a MMP cleavage site and 1-11E which were cloned into the NotI and ApaI sites as shown in FIG. 10A. The MMP cleavage site can be cleaved by MPP-1 and MMP-3.

Mouse interferon-beta was amplified with the following primers:

```
forward:
mIFNBHindFOR
                                          (SEQ ID NO: 129)
5' gct aag ctt atg aac aac agg tgg atT 3'
    HindIII     Start                 * reverse:
mIFNBEcoRIREV
                                          (SEQ ID NO: 130)
5' CGC GAA TTC GTT TTG GAA GTT TCT GGT 3'
```

1-11E was amplified with the following primers:

```
forward:
NotI1-11Efor:
                                          (SEQ ID NO: 131)
5'cag GC GGC CGC a ATG GCC GAG GTG CAG CTG 3'
    NotI       * Start reverse:
1-11EApaRev
                                          (SEQ ID NO: 132)
5 'CTTGGGCCCTCAATGGTGGTGGTGATGGTGTCTAGACCGTTT

GATTTCCACCTT 3'
```

1-11E was amplified with NotI/ApaI ends to include a histidine (His) tag and then cloned into FastBac1.AH mIFN-b/MMP/SP/His and cut with Not/Apa to liberate SP/His.

The mIFN-beta/His construct was cloned by amplifying mIFN-b with HindIII/ApaI with the following primers:

forward (this primer is the same as the primer used for cloning IFN-b/MMP/1-11E/His):
mIFNBHindFOR (SEQ ID NO: 129)

5' gct aag ctt atg aac aac agg tgg atT 3'
   HindIII    Start              * reverse primer:
mIFN-bApaRev (SEQ ID NO: 133)

5' CTTGGGCCCTCAATGGTGGTGGTGATGGTGTCTAGAGTTTTGGA
AGTTTCTGGT 3'

These constructs were transformed into DH10Bac cells from Invitrogen and the sequence was confirmed as follows:

IFN-beta/MMP/1-11E/His (50.4 kDa)

(SEQ ID NO: 134)

```
MNNRWILHAAFLLCFSTTALSINYKQLQLQERTNIRKCQELLEQLNGKIN      50
LTYRADFKIPMEMTEKMQKSYTAFAIQEMLQNVFLVFRNNFSSTGWNETI     100
VVRLLDELHQQTVFLKTVLEEKQEERLTWEMSSTALHLKSYYWRVQRYLK     150
LMKYNSYAWMVVRAEIFRNFLIIRRLTRNFQNEFGGGGSPLGLWAGGGSA     200
AAMAEVQLLESGGGLVQPGGSLRLSCAASGFTFSSYAMSWVRQAPGKGLE     250
WVSSIDDSGATTYYADSVKGRFTISRDNSKNTLYLQMNSLRAEDTAVYYC     300
AKNYSSFDYWGQGTLVTVSSGGGGSGGGGSGGGGSTDIQMTQSPSSLSAS     350
VGDRVTITCRASQSISSYLNWYQQKPGKAPKLLIYYASSLQSGVPSRFSG     400
SGSGTDFTLTISSLQPEDFATYYCQQAANYPTTFGQGTKVEIKRDIHHHH     450
HH*
```

Within this sequence, the IFN-beta portion is from amino acids 1 to 182 as follows:

(SEQ ID NO: 135)

```
MNNRWILHAAFLLCFSTTALSINYKQLQLQERTNIRKCQELLEQLNGKIN      50
LTYRADFKIPMEMTEKMQKSYTAFAIQEMLQNVFLVFRNNFSSTGWNETI     100
VVRLLDELHQQTVFLKTVLEEKQEERLTWEMSSTALHLKSYYWRVQRYLK     150
LMKYNSYAWMVVRAEIFRNFLIIRRLTRNFQN
```

The MMP linker portion is from amino acids 183 to 202 as follows:

(SEQ ID NO: 136)

```
              EFGGGGSPLGLWAGGGSA     200
              AA
```

The 1-11E portion is from amino acids 203 to 446 as follows:

(SEQ ID NO: 137)

```
MAEVQLLESGGGLVQPGGSLRLSCAASGFTFSSYAMSWVRQAPGKGLE      250
WVSSIDDSGATTYYADSVKGRFTISRDNSKNTLYLQMNSLRAEDTAVYYC    300
AKNYSSFDYWGQGTLVTVSSGGGGSGGGGSGGGGSTDIQMTQSPSSLSAS    350
VGDRVTITCRASQSISSYLNWYQQKPGKAPKLLIYYASSLQSGVPSRFSG    400
SGSGTDFTLTISSLQPEDFATYYCQQAANYPTTFGQGTKVEIKRDI
```

The His tag is from amino acids 448 to 502 as follows:

```
                         (SEQ ID NO: 138)
        HHHH           450
                                          5
        HH*
```

IFN-Beta/his (23.2 kDa)

```
                                                    (SEQ ID NO: 139)
MNNRWILHAAFLLCFSTTALSINYKQLQLQERTNIRKCQELLEQLNGKIN           50

LTYRADFKIPMEMTEKMQKSYTAFAIQEMLQNVFLVFRNNFSSTGWNETI          100

VVRLLDELHQQTVFLKTVLEEKQEERLTWEMSSTALHLKSYYWRVQRYLK          150

LMKYNSYAWMVVRAEIFRNFLIIRRLTRNFQNDIHHHHHH*
```

Within this sequence, the IFN-beta portion is from amino acids 1 to 184 as follows:

```
                                                    (SEQ ID NO: 140)
MNNRWILHAAFLLCFSTTALSINYKQLQLQERTNIRKCQELLEQLNGKIN           50

LTYRADFKIPMEMTEKMQKSYTAFAIQEMLQNVFLVFRNNFSSTGWNETI          100

VVRLLDELHQQTVFLKTVLEEKQEERLTWEMSSTALHLKSYYWRVQRYLK          150

LMKYNSYAWMVVRAEIFRNFLIIRRLTRNFQNDI
```

The His tag is from amino acids 185 to 190 as follows:

```
                                       (SEQ ID NO: 138)
                HHHHHH*
```

Figure 11:
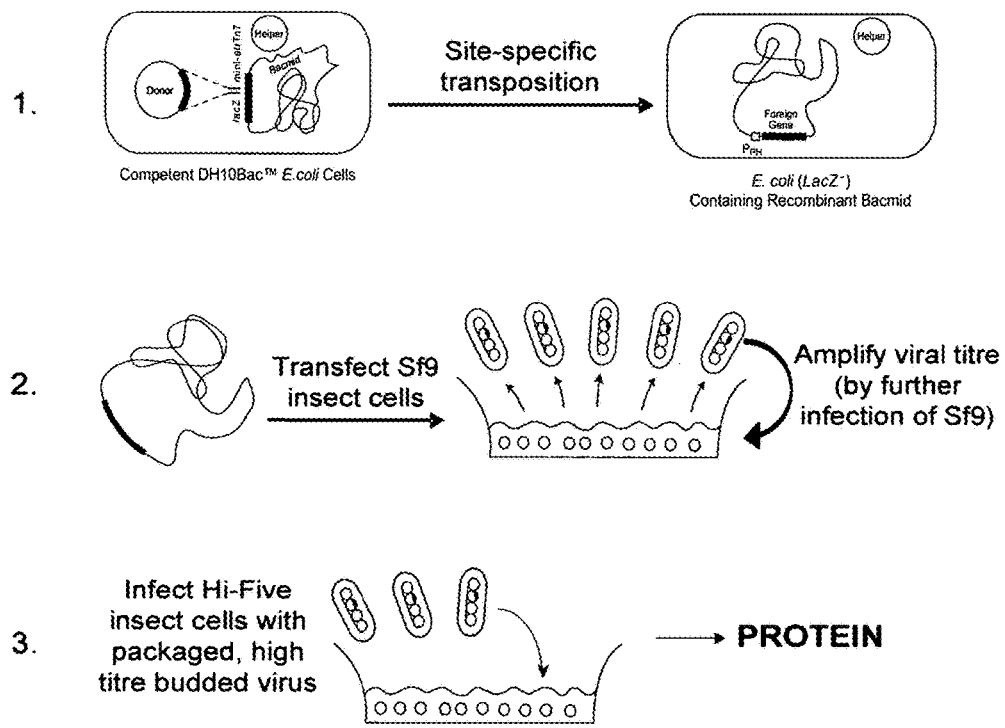
FIG. 11 shows the protocol used for expression of the IFN-β/1-11E fusion protein and the TNFR2Fc/scFv fusion protein.

The protocol for expression of the constructs is shown in FIG. 11.

Briefly, the constructs were transformed into competent DH10Bac cells (Invitrogen) to generate bacmid vectors. Recombinant bacmid vectors were confirmed by blue-white screening and PCR according to Invitrogen instructions. Bacmid DNA was transfected into Sf9 insect cells using cellfectin according to Invitrogen instructions.

Baculovirus (P1) was harvested from the supernatant of transfected cells, and used to infect fresh Sf9 cells to amplify the virus stocks. P3 virus was used to infect High 5 insect cells for 72 hours, and the supernatant was collected and run on an SDS-PAGE gel. Recombinant proteins were detected by Western blot using anti-tetra-His antibody (Qiagen) and anti-mouse HRP (Sigma).

The test expression of the fusion constructs is shown in FIG. 12.

Fusion Proteins: 1-11E/C7 with TNFR2-Fc

Cloning of TNFR2-Fc/1-11E and TNFR2-Fc/C7 pFastBac1.AH was created from pFastBac1 (Invitrogen) by cutting out BamHI/HindIII fragment containing multiple cloning sites (MCS), and replacing with a linker to give another MCS of BamHI-KpnI-HindIII-ApaI.

TNFR2Fc was cloned into the HindIII-EcoRI sites, followed by a MMP cleavage site and scFv (1-11E or C7) which were cloned into the NotI and ApaI sites as shown in FIG. 10B.

Mouse TNFR2-Fc was amplified with the following primers:

```
forward primer:
                                   (SEQ ID NO: 141)
5' GCT aag ctt ATG GCG CCC GCC GCC CTC 3'
```

```
reverse primer:
                                   (SEQ ID NO: 142)
5' CTTGAATTCTTTACCCAGAGACCGGGA 3'
```

1-11E was amplified with the same primers as above for the INFb.

The sequence of TNFR2Fc/MMP/1-11E is as follows:

```
                                   (SEQ ID NO: 143)
MAPAALWVALVFELQLWATGHTVPAQVVLTPYKPEPGYECQISQEYYDRK

AQMCCAKCPPGQYVKHFCNKTSDTVCADCEASMYTQVWNQFRTCLSCSSS

CTTDQVEIRACTKQQNRVCACEAGRYCALKTHSGSCRQCMRLSKCGPGFG

VASSRAPNGNVLCKACAPGTFSDTTSSTDVCRPHRICSILAIPGNASTDA

VCAPESDGSPPLKECPPCAAPDLLGGPSVFIFPPKIKDVLMISLSPMVTC

VVVDVSEDDPDVQISWFVNNVEVHTAQTQTHREDYNSTLRVVSALPIQHQ

DWMSGKEFKCKVNNRALPSPIEKTISKPRGPVRAPQVYVLPPPAEEMTKK

EFSLTCMITGFLPAEIAVDWTSNGRTEQNYKNTATVLDSDGSYFMYSKLR

VQKSTWERGSLFACSVVHEGLHNHLTTKTISRSLGK---EFGGGGSPLGL

WAGGGSAAA---MAEVQLLESGGGLVQPGGSLRLSCAASGFTFSSYAMSW

VRQAPGKGLEWVSSIDDSGATTYYADSVKGRFTISRDNSKNTLYLQMNSL

RAEDTAVYYCAKNYSSFDYWGQGTLVTVSSGGGGSGGGGSGGGGSTDIQM

TQSPSSLSASVGDRVTITCRASQSISSYLNWYQQKPGKAPKLLIYYASSL

QSGVPSRFSGSGSGTDFTLTISSLQPEDFATYYCQQAANYPTTFGQGTKV

EIKRDIHHHHHH
```

Of this sequence, the TNFR2Fc portion is as follows:

(SEQ ID NO: 144)
```
MAPAALWVALVFELQLWATGHTVPAQVVLTPYKPEPGYECQISQEYYDRK         50
AQMCCAKCPPGQYVKHFCNKTSDTVCADCEASMYTQVWNQFRTCLSCSSS        100
CTTDQVEIRACTKQQNRVCACEAGRYCALKTHSGSCRQCMRLSKCGPGFG        150
VASSRAPNGNVLCKACAPGTFSDTTSSTDVCRPHRICSILAIPGNASTDA        200
VCAPESDGSPPLKECPPCAAPDLLGGPSVFIFPPKIKDVLMISLSPMVTC        250
VVVDVSEDDPDVQISWFVNNVEVHTAQTQTHREDYNSTLRVVSALPIQHQ        300
DWMSGKEFKCKVNNRALPSPIEKTISKPRGPVRAPQVYVLPPPAEEMTKK        350
EFSLTCMITGFLPAEIAVDWTSNGRTEQNYKNTATVLDSDGSYFMYSKLR        400
VQKSTWERGSLFACSVVHEGLHNHLTTKTISRSLGK*
```

The MMP linker portion is as follows:

(SEQ ID NO: 136)
```
EFGGGGSPLGLWAGGGSAAA
```

The 1-11E portion is as follows:

(SEQ ID NO: 137)
```
MAEVQLLESGGGLVQPGGSLRLSCAASGFTFSSYAMSWVRQAPGKGLE
WVSSIDDSGATTYYADSVKGRFTISRDNSKNTLYLQMNSLRAEDTAVYYC
AKNYSSFDYWGQGTLVTVSSGGGGSGGGGSGGGGSTDIQMTQSPSSLSAS
VGDRVTITCRASQSISSYLNWYQQKPGKAPKLLIYYASSLQSGVPSRFSG
SGSGTDFTLTISSLQPEDFATYYCQQAANYPTTFGQGTKVEIKRDI
```

The His tag is as follows:

(SEQ ID NO: 138)
```
HHHHHH*
```

As a negative control a non specific scFv was developed that binds to Hen Egg Lysosyme (HEL). Clone C7 was the best expressed and was taken forward for TNFR2Fc fusion as done for 1-11E.

Sequence of TNFR2Fc/MMP/C7:

(SEQ ID NO: 147)
```
MAPAALWVALVFELQLWATGHTVPAQVVLTPYKPEPGYECQISQEYYDRK
AQMCCAKCPPGQYVKHFCNKTSDTVCADCEASMYTQVWNQFRTCLSCSSS
CTTDQVEIRACTKQQNRVCACEAGRYCALKTHSGSCRQCMRLSKCGPGFG
VASSRAPNGNVLCKACAPGTFSDTTSSTDVCRPHRICSILAIPGNASTDA
VCAPESDGSPPLKECPPCAAPDLLGGPSVFIFPPKIKDVLMISLSPMVTC
VVVDVSEDDPDVQISWFVNNVEVHTAQTQTHREDYNSTLRVVSALPIQHQ
DWMSGKEFKCKVNNRALPSPIEKTISKPRGPVRAPQVYVLPPPAEEMTKK
EFSLTCMITGFLPAEIAVDWTSNGRTEQNYKNTATVLDSDGSYFMYSKLR
VQKSTWERGSLFACSVVHEGLHNHLTTKTISRSLGKEFGGGGSPLGLWAG
GGSAAAMAEVQLLESGGGLVQPGGSLRLSCAASGFTFSSYAMSWVRQAPG
KGLEWVSTISYAGASTAYADSVKGRFTISRDNSKNTLYLQMNSLRAEDTA
VYYCAKTSTSFDYWGQGTLVTVSTDIQMTQSPSSLSASVGDRVTITCRAS
QSISSYLNWYQQKPGKAPKLLIYNASYLQSGVPSRFSGSGSGTDFTLTIS
SLQPEDFATYYCQQAYAGPYTFGQGTKVEIKRDIHHHHHH*
```

Of this sequence, the TNFR2Fc portion is as follows:

(SEQ ID NO: 148)
```
MAPAALWVALVFELQLWATGHTVPAQVVLTPYKPEPGYECQISQEYYDRK         50
AQMCCAKCPPGQYVKHFCNKTSDTVCADCEASMYTQVWNQFRTCLSCSSS        100
CTTDQVEIRACTKQQNRVCACEAGRYCALKTHSGSCRQCMRLSKCGPGFG        150
VASSRAPNGNVLCKACAPGTFSDTTSSTDVCRPHRICSILAIPGNASTDA        200
VCAPESDGSPPLKECPPCAAPDLLGGPSVFIFPPKIKDVLMISLSPMVTC        250
VVVDVSEDDPDVQISWFVNNVEVHTAQTQTHREDYNSTLRVVSALPIQHQ        300
DWMSGKEFKCKVNNRALPSPIEKTISKPRGPVRAPQVYVLPPPAEEMTKK        350
EFSLTCMITGFLPAEIAVDWTSNGRTEQNYKNTATVLDSDGSYFMYSKLR        400
VQKSTWERGSLFACSVVHEGLHNHLTTKTISRSLGK*
```

The MMP linker portion is as follows:

(SEQ ID NO: 149)
EFGGGGSPLGLWAGGGSAAA

The C7 portion is as follows:

(SEQ ID NO: 150)
MAEVQLLESGGGLVQPGGSLRLSCAASGFT
FSSYAMSWVRQAPGKGLEWVSTISYAGASTAYADSVKGRFTISRDNSKNT
LYLQMNSLRAEDTAVYYCAKTSTSFDYWGQGTLVTVSTDIQMTQSPSSLS
ASVGDRVTITCRASQSISSYLNWYQQKPGKAPKLLIYNASYLQSGVPSRF
SGSGSGTDFTLTISSLQPEDFATYYCQQAYAGPYTFGQGTKVEIKRDI

The His tag is as follows:

(SEQ ID NO: 138)
HHHHHH*

The protocol for expression of the constructs is shown in FIG. 11 and is as described above for the IFN-beta/1-11E fusion protein.

Infected Hi-5 cells were grown for 3 days at 27° C. After 3 days, different 100, 50, 25 and 12 microliter aliquots of cell supernatant were taken for Western blot analysis. Fusion protein was probed with anti-His tag antibodies. As shown in FIG. 13 the apparent molecular weight of the TNFR2Fc fusion proteins is slightly above 75 kDa which reflects the predicted 50 kDa TNFR2Fc plus 30 kDa scFv.

The invention claimed is:

1. A composition comprising an antibody or fragment thereof against oxidised collagen II (CII) in which the antibody or fragment thereof is conjugated to a pharmaceutically active moiety, wherein the antibody or fragment thereof comprises CDR sequences in the variable heavy (VH) chains and variable light (VL) chains as follows:
CDRH2: SIDDSGATTYYADSVKG (SEQ ID NO: 14),
CDRH3: NYSSFDY (SEQ ID NO: 48),
CDRL2: YASSLQS (SEQ ID NO: 73), and
CDRL3: QQAANYPTT (SEQ ID NO: 100),
wherein the CDRH1 and CDRL1 sequences are the same as those of scFv 1-11E.

2. A composition as claimed in claim 1, in which the antibody is a polyclonal antibody or a monoclonal antibody.

3. A composition as claimed in claim 1, in which the antibody fragment is a Fab, scFv, single domain (dAb) antibody, diabody, minibody, or scFv-Fc fragment.

4. A composition as claimed in claim 1, in which the antibody is the scFv 1-11E.

5. A composition as claimed in claim 1, in which the composition comprises a proteolytic cleavage site between the antibody or fragment thereof and the pharmaceutically active moiety.

6. A composition as claimed in claim 5, in which the proteolytic cleavage site is a matrix metalloproteinase (MMP) cleavage site, a serine protease cleavage site, or a site cleavable by a parasitic protease derived from a pathogenic organism.

7. A composition as claimed in claim 6, in which the proteolytic cleavage site is a MMP cleavage site.

8. A composition as claimed in claim 7, in which the MMP cleavage site is one or more of MMP1, MMP2, MMP3, MMP7, MMP8, MMP9 or MMP10 as shown in FIG. 5.

9. A composition as claimed in claim 1, in which the pharmaceutically active moiety is an antibody or a fragment thereof, a growth factor, a differentiation factor, a cytokine molecule, an interferon, a bone morphogenetic protein (BMP); a chemokine, a MCP (monocyte chemotactic protein), a cytokine inhibitor; a cytokine receptor, a free-radical scavenging enzyme or a toxin.

10. A composition as claimed in claim 9, in which the pharmaceutically active moiety is an interferon.

11. A composition as claimed in claim 10, in which the pharmaceutically active moiety is interferon beta (IFN-β).

12. A composition as claimed in claim 1, which composition comprises the scFv 1-11E, a MMP cleavage site and IFN-β.

13. A composition as claimed in claim 9, in which the pharmaceutically active moiety is a TNF receptor (TNFR) antibody fusion protein.

14. A composition as claimed in claim 13, in which the pharmaceutically active moiety is TNFR2-Fc.

15. A composition as claimed in claim 14, which composition comprises the scFv 1-11E, a MMP cleavage site and TNFR2-Fc.

16. A composition as claimed in claim 1, in which the pharmaceutically active moiety is a glycosaminoglycan molecule, chondroitin, a non-steroidal anti-inflammatory drug (NSAID), a steroid, sodium hyaluronate or hyaluronic acid, colchicine or hydroxychloroquine.

17. A composition comprising an antibody or fragment thereof against oxidised collagen II (CII) and a detectable label, wherein the antibody or fragment thereof comprises CDR sequences in the variable heavy (VH) chains and variable light (VL) chains as follows:
CDRH2: SIDDSGATTYYADSVKG (SEQ ID NO: 14)
CDRH3: NYSSFDY (SEQ ID NO: 48)
CDRL2: YASSLQS (SEQ ID NO: 73)
CDRL3: QQAANYPTT (SEQ ID NO: 100),
wherein the CDRH1 and CDRL1 sequences are the same as those of scFv 1-11E.

18. A composition as claimed in claim 17, in which the detectable label is a radionuclide or a dye.

19. A composition as claimed in claim 18, in which the detectable label is a dye.

20. A composition as claimed in claim 9, in which the pharmaceutically active moiety is IL-10.

21. A composition as claimed in claim 20, which composition comprises the scFv 1-11E, a MMP cleavage site, and IL-10.

* * * * *

SEQUENCE LISTING

```
<160> NUMBER OF SEQ ID NOS: 223

<210> SEQ ID NO 1
<211> LENGTH: 17
<212> TYPE: PRT
<213> ORGANISM: Homo sapiens

<400> SEQUENCE: 1

Asp Ile Ser Ser Thr Gly Ser Tyr Thr Ala Tyr Ala Asp Ser Val Lys
1               5                   10                  15
Gly

<210> SEQ ID NO 2
<211> LENGTH: 17
<212> TYPE: PRT
<213> ORGANISM: Homo sapiens

<400> SEQUENCE: 2

Ala Ile Ser Ala Ala Gly Thr Ala Thr Ala Tyr Ala Asp Ser Val Lys
1               5                   10                  15
Gly

<210> SEQ ID NO 3
<211> LENGTH: 17
<212> TYPE: PRT
<213> ORGANISM: Homo sapiens

<400> SEQUENCE: 3

Ser Ile Ser Asn Ser Gly Ser Tyr Thr Asp Tyr Ala Asp Ser Val Lys
1               5                   10                  15
Gly

<210> SEQ ID NO 4
<211> LENGTH: 17
<212> TYPE: PRT
<213> ORGANISM: Homo sapiens

<400> SEQUENCE: 4

Ser Ile Asn Asn Tyr Gly Ser Asn Thr Ala Tyr Ala Asp Ser Val Lys
1               5                   10                  15
Gly

<210> SEQ ID NO 5
<211> LENGTH: 17
```

```
<212> TYPE: PRT
<213> ORGANISM: Homo sapiens

<400> SEQUENCE: 5

Ser Ile Ser Tyr Thr Gly Asn Ser Thr Asp Tyr Ala Asp Ser Val Lys
1               5                   10                  15
Gly

<210> SEQ ID NO 6
<211> LENGTH: 17
<212> TYPE: PRT
<213> ORGANISM: Homo sapiens

<400> SEQUENCE: 6

Asn Ile Ala Thr Asp Gly Thr Thr Thr Tyr Tyr Ala Asp Ser Val Lys
1               5                   10                  15
Gly

<210> SEQ ID NO 7
<211> LENGTH: 17
<212> TYPE: PRT
<213> ORGANISM: Homo sapiens

<400> SEQUENCE: 7

Ser Ile Ser Asn Ser Gly Thr Asn Thr Asp Tyr Ala Asp Ser Val Lys
1               5                   10                  15
Gly

<210> SEQ ID NO 8
<211> LENGTH: 17
<212> TYPE: PRT
<213> ORGANISM: Homo sapiens

<400> SEQUENCE: 8

Ser Ile Ser Tyr Thr Gly Asp Ser Thr Tyr Tyr Ala Asp Ser Val Lys
1               5                   10                  15
Gly

<210> SEQ ID NO 9
<211> LENGTH: 17
<212> TYPE: PRT
<213> ORGANISM: Homo sapiens

<400> SEQUENCE: 9

Ser Ile Asn Asp Ser Gly Thr Thr Thr Tyr Tyr Ala Asp Ser Val Lys
1               5                   10                  15
Gly

<210> SEQ ID NO 10
<211> LENGTH: 17
<212> TYPE: PRT
<213> ORGANISM: Homo sapiens

<400> SEQUENCE: 10

Ser Ile Asp Ser Ala Gly Ala Ser Thr Tyr Tyr Ala Asp Ser Val Lys
1               5                   10                  15
Gly

<210> SEQ ID NO 11
<211> LENGTH: 17
<212> TYPE: PRT
```

<213> ORGANISM: Homo sapiens

<400> SEQUENCE: 11

Ser Ile Asn Ala Thr Gly Tyr Gly Thr Tyr Tyr Ala Asp Ser Val Lys
1               5                   10                  15

Gly

<210> SEQ ID NO 12
<211> LENGTH: 17
<212> TYPE: PRT
<213> ORGANISM: Homo sapiens

<400> SEQUENCE: 12

Ser Ile Asn Ser Asn Gly Thr Asp Thr Tyr Tyr Ala Asp Ser Val Lys
1               5                   10                  15

Gly

<210> SEQ ID NO 13
<211> LENGTH: 17
<212> TYPE: PRT
<213> ORGANISM: Homo sapiens

<400> SEQUENCE: 13

Ser Ile Ser Ala Thr Gly Ser Ser Thr Tyr Tyr Ala Asp Ser Val Lys
1               5                   10                  15

Gly

<210> SEQ ID NO 14
<211> LENGTH: 17
<212> TYPE: PRT
<213> ORGANISM: Homo sapiens

<400> SEQUENCE: 14

Ser Ile Asp Asp Ser Gly Ala Thr Thr Tyr Tyr Ala Asp Ser Val Lys
1               5                   10                  15

Gly

<210> SEQ ID NO 15
<211> LENGTH: 17
<212> TYPE: PRT
<213> ORGANISM: Homo sapiens

<400> SEQUENCE: 15

Ser Ile Ala Ser Thr Gly Asp Ser Thr Tyr Tyr Ala Asp Ser Val Lys
1               5                   10                  15

Gly

<210> SEQ ID NO 16
<211> LENGTH: 17
<212> TYPE: PRT
<213> ORGANISM: Homo sapiens

<400> SEQUENCE: 16

Ser Ile Ser Thr Asn Gly Ser Ser Thr Tyr Tyr Ala Asp Ser Val Lys
1               5                   10                  15

Gly

<210> SEQ ID NO 17
<211> LENGTH: 17
<212> TYPE: PRT
<213> ORGANISM: Homo sapiens

```
<400> SEQUENCE: 17

Ser Ile Asp Thr Thr Gly Thr Thr Tyr Phe Ala Asp Ser Val Lys
1               5                   10                  15

Gly

<210> SEQ ID NO 18
<211> LENGTH: 17
<212> TYPE: PRT
<213> ORGANISM: Homo sapiens

<400> SEQUENCE: 18

Thr Ile Ser Tyr Ser Gly Asn Asn Thr Tyr Tyr Ala Asp Ser Val Lys
1               5                   10                  15

Gly

<210> SEQ ID NO 19
<211> LENGTH: 17
<212> TYPE: PRT
<213> ORGANISM: Homo sapiens

<400> SEQUENCE: 19

Ser Ile Asp Ala Gly Gly Asn Gly Thr Tyr Tyr Ala Asp Ser Val Lys
1               5                   10                  15

Gly

<210> SEQ ID NO 20
<211> LENGTH: 17
<212> TYPE: PRT
<213> ORGANISM: Homo sapiens

<400> SEQUENCE: 20

Ser Ile Asp Ser Ala Gly Asn Ala Thr Tyr Tyr Ala Asp Ser Val Lys
1               5                   10                  15

Gly

<210> SEQ ID NO 21
<211> LENGTH: 17
<212> TYPE: PRT
<213> ORGANISM: Homo sapiens

<400> SEQUENCE: 21

Ser Ile Thr Asp Ser Gly Asp Thr Thr Tyr Tyr Ala Asp Ser Val Lys
1               5                   10                  15

Gly

<210> SEQ ID NO 22
<211> LENGTH: 17
<212> TYPE: PRT
<213> ORGANISM: Homo sapiens

<400> SEQUENCE: 22

Ser Ile Ala Thr Thr Gly Asp Asn Thr Tyr Tyr Ala Asp Ser Val Lys
1               5                   10                  15

Gly

<210> SEQ ID NO 23
<211> LENGTH: 17
<212> TYPE: PRT
<213> ORGANISM: Homo sapiens
```

```
<400> SEQUENCE: 23

Ala Ile Asn Ala Tyr Gly Gly Ser Thr Tyr Tyr Ala Asp Ser Val Lys
1               5                   10                  15

Gly

<210> SEQ ID NO 24
<211> LENGTH: 17
<212> TYPE: PRT
<213> ORGANISM: Homo sapiens

<400> SEQUENCE: 24

Ser Ile Ala Thr Thr Gly Thr Ser Thr Thr Tyr Ala Asp Ser Val Lys
1               5                   10                  15

Gly

<210> SEQ ID NO 25
<211> LENGTH: 17
<212> TYPE: PRT
<213> ORGANISM: Homo sapiens

<400> SEQUENCE: 25

Thr Ile Asp Thr Ala Gly Ser Tyr Thr Asp Tyr Ala Asp Ser Val Lys
1               5                   10                  15

Gly

<210> SEQ ID NO 26
<211> LENGTH: 17
<212> TYPE: PRT
<213> ORGANISM: Homo sapiens

<400> SEQUENCE: 26

Ser Ile Ser Asn Asn Gly Ser Ser Thr Tyr Tyr Ala Asp Ser Val Lys
1               5                   10                  15

Gly

<210> SEQ ID NO 27
<211> LENGTH: 17
<212> TYPE: PRT
<213> ORGANISM: Homo sapiens

<400> SEQUENCE: 27

Ser Ile Ala Tyr Gly Gly Ala Gly Thr Asp Tyr Ala Asp Ser Val Lys
1               5                   10                  15

Gly

<210> SEQ ID NO 28
<211> LENGTH: 17
<212> TYPE: PRT
<213> ORGANISM: Homo sapiens

<400> SEQUENCE: 28

Ala Ile Ala Asn Thr Gly Ser Ala Thr Asn Tyr Ala Asp Ser Val Lys
1               5                   10                  15

Gly

<210> SEQ ID NO 29
<211> LENGTH: 17
<212> TYPE: PRT
<213> ORGANISM: Homo sapiens

<400> SEQUENCE: 29
```

```
Ser Ile Ser Thr Ala Gly Thr Tyr Thr Asp Tyr Ala Asp Ser Val Lys
1               5                   10                  15
Gly

<210> SEQ ID NO 30
<211> LENGTH: 17
<212> TYPE: PRT
<213> ORGANISM: Homo sapiens

<400> SEQUENCE: 30

Ser Ile Asn Asp Thr Gly Tyr Thr Thr Tyr Tyr Ala Asp Ser Val Lys
1               5                   10                  15
Gly

<210> SEQ ID NO 31
<211> LENGTH: 17
<212> TYPE: PRT
<213> ORGANISM: Homo sapiens

<400> SEQUENCE: 31

Ser Ile Ala Ser Ser Gly Thr Thr Thr Tyr Tyr Ala Asp Ser Val Lys
1               5                   10                  15
Gly

<210> SEQ ID NO 32
<211> LENGTH: 17
<212> TYPE: PRT
<213> ORGANISM: Homo sapiens

<400> SEQUENCE: 32

Thr Ile Thr Ser Thr Gly Ala Ala Thr Ala Tyr Ala Asp Ser Val Lys
1               5                   10                  15
Gly

<210> SEQ ID NO 33
<211> LENGTH: 17
<212> TYPE: PRT
<213> ORGANISM: Homo sapiens

<400> SEQUENCE: 33

Ala Ile Asp Gly Thr Gly Tyr Gly Thr Ala Tyr Ala Asp Ser Val Lys
1               5                   10                  15
Gly

<210> SEQ ID NO 34
<211> LENGTH: 17
<212> TYPE: PRT
<213> ORGANISM: Homo sapiens

<400> SEQUENCE: 34

Ser Ile Ala Asn Ala Gly Thr Ala Thr Tyr Tyr Ala Asp Ser Val Lys
1               5                   10                  15
Gly

<210> SEQ ID NO 35
<211> LENGTH: 17
<212> TYPE: PRT
<213> ORGANISM: Homo sapiens

<400> SEQUENCE: 35
```

Ser Ile Asp Ser Ala Gly Asp Ser Thr Tyr Tyr Ala Asp Ser Val Lys
1               5                   10                  15

Gly

<210> SEQ ID NO 36
<211> LENGTH: 17
<212> TYPE: PRT
<213> ORGANISM: Homo sapiens

<400> SEQUENCE: 36

Ser Ile Ser Ser Ser Gly Asp Thr Thr Tyr Tyr Ala Asp Ser Val Lys
1               5                   10                  15

Gly

<210> SEQ ID NO 37
<211> LENGTH: 17
<212> TYPE: PRT
<213> ORGANISM: Homo sapiens

<400> SEQUENCE: 37

Ser Ile Asp Thr Gly Gly Ser Tyr Thr Asp Tyr Ala Asp Ser Val Lys
1               5                   10                  15

Gly

<210> SEQ ID NO 38
<211> LENGTH: 17
<212> TYPE: PRT
<213> ORGANISM: Homo sapiens

<400> SEQUENCE: 38

Ser Ile Asp Ala Ser Gly Ala Asn Thr Ala Tyr Ala Asp Ser Val Lys
1               5                   10                  15

Gly

<210> SEQ ID NO 39
<211> LENGTH: 7
<212> TYPE: PRT
<213> ORGANISM: Homo sapiens

<400> SEQUENCE: 39

Gly Ala Gly Ser Phe Asp Tyr
1               5

<210> SEQ ID NO 40
<211> LENGTH: 7
<212> TYPE: PRT
<213> ORGANISM: Homo sapiens

<400> SEQUENCE: 40

Gly Tyr Asp Thr Phe Asp Tyr
1               5

<210> SEQ ID NO 41
<211> LENGTH: 7
<212> TYPE: PRT
<213> ORGANISM: Homo sapiens

<400> SEQUENCE: 41

Gly Tyr Gly Ser Phe Asp Tyr
1               5

<210> SEQ ID NO 42

```
<211> LENGTH: 7
<212> TYPE: PRT
<213> ORGANISM: Homo sapiens

<400> SEQUENCE: 42

Gly Tyr Ser Ser Phe Asp Tyr
1               5

<210> SEQ ID NO 43
<211> LENGTH: 7
<212> TYPE: PRT
<213> ORGANISM: Homo sapiens

<400> SEQUENCE: 43

Gly Tyr Thr Ala Phe Asp Tyr
1               5

<210> SEQ ID NO 44
<211> LENGTH: 7
<212> TYPE: PRT
<213> ORGANISM: Homo sapiens

<400> SEQUENCE: 44

Asn Ser Thr Tyr Phe Asp Tyr
1               5

<210> SEQ ID NO 45
<211> LENGTH: 7
<212> TYPE: PRT
<213> ORGANISM: Homo sapiens

<400> SEQUENCE: 45

Asn Tyr Ala Ser Phe Asp Tyr
1               5

<210> SEQ ID NO 46
<211> LENGTH: 7
<212> TYPE: PRT
<213> ORGANISM: Homo sapiens

<400> SEQUENCE: 46

Asn Tyr Ser Ala Phe Asp Tyr
1               5

<210> SEQ ID NO 47
<211> LENGTH: 7
<212> TYPE: PRT
<213> ORGANISM: Homo sapiens

<400> SEQUENCE: 47

Asn Tyr Ser Asp Phe Asp Tyr
1               5

<210> SEQ ID NO 48
<211> LENGTH: 7
<212> TYPE: PRT
<213> ORGANISM: Homo sapiens

<400> SEQUENCE: 48

Asn Tyr Ser Ser Phe Asp Tyr
1               5

<210> SEQ ID NO 49
<211> LENGTH: 7
<212> TYPE: PRT
```

<213> ORGANISM: Homo sapiens

<400> SEQUENCE: 49

Asn Tyr Ser Thr Phe Asp Tyr
1               5

<210> SEQ ID NO 50
<211> LENGTH: 7
<212> TYPE: PRT
<213> ORGANISM: Homo sapiens

<400> SEQUENCE: 50

Asn Tyr Ser Tyr Phe Asp Tyr
1               5

<210> SEQ ID NO 51
<211> LENGTH: 7
<212> TYPE: PRT
<213> ORGANISM: Homo sapiens

<400> SEQUENCE: 51

Asn Tyr Thr Ala Phe Asp Tyr
1               5

<210> SEQ ID NO 52
<211> LENGTH: 7
<212> TYPE: PRT
<213> ORGANISM: Homo sapiens

<400> SEQUENCE: 52

Asn Tyr Thr Asp Phe Asp Tyr
1               5

<210> SEQ ID NO 53
<211> LENGTH: 7
<212> TYPE: PRT
<213> ORGANISM: Homo sapiens

<400> SEQUENCE: 53

Asn Tyr Thr Tyr Phe Asp Tyr
1               5

<210> SEQ ID NO 54
<211> LENGTH: 7
<212> TYPE: PRT
<213> ORGANISM: Homo sapiens

<400> SEQUENCE: 54

Ser Tyr Ala Asp Phe Asp Tyr
1               5

<210> SEQ ID NO 55
<211> LENGTH: 7
<212> TYPE: PRT
<213> ORGANISM: Homo sapiens

<400> SEQUENCE: 55

Ser Tyr Ala Thr Phe Asp Tyr
1               5

<210> SEQ ID NO 56
<211> LENGTH: 7
<212> TYPE: PRT
<213> ORGANISM: Homo sapiens

<400> SEQUENCE: 56

Ser Tyr Asp Thr Phe Asp Tyr
1               5

<210> SEQ ID NO 57
<211> LENGTH: 7
<212> TYPE: PRT
<213> ORGANISM: Homo sapiens

<400> SEQUENCE: 57

Ser Tyr Ser Asn Phe Asp Tyr
1               5

<210> SEQ ID NO 58
<211> LENGTH: 7
<212> TYPE: PRT
<213> ORGANISM: Homo sapiens

<400> SEQUENCE: 58

Ser Tyr Ser Tyr Phe Asp Tyr
1               5

<210> SEQ ID NO 59
<211> LENGTH: 7
<212> TYPE: PRT
<213> ORGANISM: Homo sapiens

<400> SEQUENCE: 59

Ser Tyr Thr Thr Phe Asp Tyr
1               5

<210> SEQ ID NO 60
<211> LENGTH: 7
<212> TYPE: PRT
<213> ORGANISM: Homo sapiens

<400> SEQUENCE: 60

Thr Tyr Gly Thr Phe Asp Tyr
1               5

<210> SEQ ID NO 61
<211> LENGTH: 7
<212> TYPE: PRT
<213> ORGANISM: Homo sapiens

<400> SEQUENCE: 61

Ala Ala Ser Ala Leu Gln Ser
1               5

<210> SEQ ID NO 62
<211> LENGTH: 7
<212> TYPE: PRT
<213> ORGANISM: Homo sapiens

<400> SEQUENCE: 62

Ala Ala Ser Ser Leu Gln Ser
1               5

<210> SEQ ID NO 63
<211> LENGTH: 7
<212> TYPE: PRT
<213> ORGANISM: Homo sapiens

<400> SEQUENCE: 63

Ala Ala Ser Thr Leu Gln Ser
1               5

<210> SEQ ID NO 64
<211> LENGTH: 7
<212> TYPE: PRT
<213> ORGANISM: Homo sapiens

<400> SEQUENCE: 64

Ala Ala Ser Tyr Leu Gln Ser
1               5

<210> SEQ ID NO 65
<211> LENGTH: 7
<212> TYPE: PRT
<213> ORGANISM: Homo sapiens

<400> SEQUENCE: 65

Tyr Ala Ser Tyr Leu Gln Ser
1               5

<210> SEQ ID NO 66
<211> LENGTH: 7
<212> TYPE: PRT
<213> ORGANISM: Homo sapiens

<400> SEQUENCE: 66

Ser Ala Ser Thr Leu Gln Ser
1               5

<210> SEQ ID NO 67
<211> LENGTH: 7
<212> TYPE: PRT
<213> ORGANISM: Homo sapiens

<400> SEQUENCE: 67

Ala Ala Ser Asp Leu Gln Ser
1               5

<210> SEQ ID NO 68
<211> LENGTH: 7
<212> TYPE: PRT
<213> ORGANISM: Homo sapiens

<400> SEQUENCE: 68

Asn Ala Ser Ser Leu Gln Ser
1               5

<210> SEQ ID NO 69
<211> LENGTH: 7
<212> TYPE: PRT
<213> ORGANISM: Homo sapiens

<400> SEQUENCE: 69

Thr Ala Ser Asn Leu Gln Ser
1               5

<210> SEQ ID NO 70
<211> LENGTH: 7
<212> TYPE: PRT
<213> ORGANISM: Homo sapiens

<400> SEQUENCE: 70

Ser Ala Ser Ala Leu Gln Ser
1               5

<210> SEQ ID NO 71
<211> LENGTH: 7
<212> TYPE: PRT
<213> ORGANISM: Homo sapiens

<400> SEQUENCE: 71

Thr Ala Ser Ala Leu Gln Ser
1               5

<210> SEQ ID NO 72
<211> LENGTH: 7
<212> TYPE: PRT
<213> ORGANISM: Homo sapiens

<400> SEQUENCE: 72

Ser Ala Ser Asp Leu Gln Ser
1               5

<210> SEQ ID NO 73
<211> LENGTH: 7
<212> TYPE: PRT
<213> ORGANISM: Homo sapiens

<400> SEQUENCE: 73

Tyr Ala Ser Ser Leu Gln Ser
1               5

<210> SEQ ID NO 74
<211> LENGTH: 7
<212> TYPE: PRT
<213> ORGANISM: Homo sapiens

<400> SEQUENCE: 74

Asp Ala Ser Gly Leu Gln Ser
1               5

<210> SEQ ID NO 75
<211> LENGTH: 7
<212> TYPE: PRT
<213> ORGANISM: Homo sapiens

<400> SEQUENCE: 75

Ser Ala Ser Tyr Leu Gln Ser
1               5

<210> SEQ ID NO 76
<211> LENGTH: 7
<212> TYPE: PRT
<213> ORGANISM: Homo sapiens

<400> SEQUENCE: 76

Thr Ala Ser Ser Leu Gln Ser
1               5

<210> SEQ ID NO 77
<211> LENGTH: 7
<212> TYPE: PRT
<213> ORGANISM: Homo sapiens

<400> SEQUENCE: 77

Thr Ala Ser Asn Leu Gln Ser
1               5

```
<210> SEQ ID NO 78
<211> LENGTH: 7
<212> TYPE: PRT
<213> ORGANISM: Homo sapiens

<400> SEQUENCE: 78

Ala Ala Ser Thr Leu Gln Ser
1               5

<210> SEQ ID NO 79
<211> LENGTH: 7
<212> TYPE: PRT
<213> ORGANISM: Homo sapiens

<400> SEQUENCE: 79

Ser Ala Ser Ser Leu Gln Ser
1               5

<210> SEQ ID NO 80
<211> LENGTH: 7
<212> TYPE: PRT
<213> ORGANISM: Homo sapiens

<400> SEQUENCE: 80

Thr Ala Ser Thr Leu Gln Ser
1               5

<210> SEQ ID NO 81
<211> LENGTH: 7
<212> TYPE: PRT
<213> ORGANISM: Homo sapiens

<400> SEQUENCE: 81

Gly Ala Ser Thr Leu Gln Ser
1               5

<210> SEQ ID NO 82
<211> LENGTH: 7
<212> TYPE: PRT
<213> ORGANISM: Homo sapiens

<400> SEQUENCE: 82

Ala Ala Ser Asn Leu Gln Ser
1               5

<210> SEQ ID NO 83
<211> LENGTH: 7
<212> TYPE: PRT
<213> ORGANISM: Homo sapiens

<400> SEQUENCE: 83

Asp Ala Ser Thr Leu Gln Ser
1               5

<210> SEQ ID NO 84
<211> LENGTH: 7
<212> TYPE: PRT
<213> ORGANISM: Homo sapiens

<400> SEQUENCE: 84

Gly Ala Ser Ser Leu Gln Ser
1               5

<210> SEQ ID NO 85
<211> LENGTH: 7
```

```
<212> TYPE: PRT
<213> ORGANISM: Homo sapiens

<400> SEQUENCE: 85

Thr Ala Ser Tyr Leu Gln Ser
1               5

<210> SEQ ID NO 86
<211> LENGTH: 9
<212> TYPE: PRT
<213> ORGANISM: Homo sapiens

<400> SEQUENCE: 86

Gln Gln Ser Ser Ser Thr Pro Thr Thr
1               5

<210> SEQ ID NO 87
<211> LENGTH: 9
<212> TYPE: PRT
<213> ORGANISM: Homo sapiens

<400> SEQUENCE: 87

Gln Gln Asn Tyr Gly Tyr Pro Asn Thr
1               5

<210> SEQ ID NO 88
<211> LENGTH: 9
<212> TYPE: PRT
<213> ORGANISM: Homo sapiens

<400> SEQUENCE: 88

Gln Gln Ala Asn Ser Ser Pro Asp Thr
1               5

<210> SEQ ID NO 89
<211> LENGTH: 9
<212> TYPE: PRT
<213> ORGANISM: Homo sapiens

<400> SEQUENCE: 89

Gln Gln Thr Ser Ser Ser Pro Asp Thr
1               5

<210> SEQ ID NO 90
<211> LENGTH: 9
<212> TYPE: PRT
<213> ORGANISM: Homo sapiens

<400> SEQUENCE: 90

Gln Gln Ala Asp Ser Thr Pro Thr Thr
1               5

<210> SEQ ID NO 91
<211> LENGTH: 9
<212> TYPE: PRT
<213> ORGANISM: Homo sapiens

<400> SEQUENCE: 91

Gln Gln Ala Ala Thr Ser Pro Thr Thr
1               5

<210> SEQ ID NO 92
<211> LENGTH: 9
<212> TYPE: PRT
<213> ORGANISM: Homo sapiens
```

<400> SEQUENCE: 92

Gln Gln Gly Ser Ala Ser Pro Ser Thr
1               5

<210> SEQ ID NO 93
<211> LENGTH: 9
<212> TYPE: PRT
<213> ORGANISM: Homo sapiens

<400> SEQUENCE: 93

Gln Gln Ser Asp Ser Ala Pro Thr Thr
1               5

<210> SEQ ID NO 94
<211> LENGTH: 9
<212> TYPE: PRT
<213> ORGANISM: Homo sapiens

<400> SEQUENCE: 94

Gln Gln Ser Asp Thr Tyr Pro Ser Thr
1               5

<210> SEQ ID NO 95
<211> LENGTH: 9
<212> TYPE: PRT
<213> ORGANISM: Homo sapiens

<400> SEQUENCE: 95

Gln Gln Ser Tyr Ala Ser Pro Thr Thr
1               5

<210> SEQ ID NO 96
<211> LENGTH: 9
<212> TYPE: PRT
<213> ORGANISM: Homo sapiens

<400> SEQUENCE: 96

Gln Gln Thr Gly Ser Tyr Pro Thr Thr
1               5

<210> SEQ ID NO 97
<211> LENGTH: 9
<212> TYPE: PRT
<213> ORGANISM: Homo sapiens

<400> SEQUENCE: 97

Gln Gln Gly Asp Ser Tyr Pro Thr Thr
1               5

<210> SEQ ID NO 98
<211> LENGTH: 9
<212> TYPE: PRT
<213> ORGANISM: Homo sapiens

<400> SEQUENCE: 98

Gln Gln Gly Tyr Gly Ala Pro Thr Thr
1               5

<210> SEQ ID NO 99
<211> LENGTH: 9
<212> TYPE: PRT
<213> ORGANISM: Homo sapiens

<400> SEQUENCE: 99

Gln Gln Ser Ser Tyr Thr Pro Thr Thr
1               5

<210> SEQ ID NO 100
<211> LENGTH: 9
<212> TYPE: PRT
<213> ORGANISM: Homo sapiens

<400> SEQUENCE: 100

Gln Gln Ala Ala Asn Tyr Pro Thr Thr
1               5

<210> SEQ ID NO 101
<211> LENGTH: 9
<212> TYPE: PRT
<213> ORGANISM: Homo sapiens

<400> SEQUENCE: 101

Gln Gln Ala Ser Asn Tyr Pro Thr Thr
1               5

<210> SEQ ID NO 102
<211> LENGTH: 9
<212> TYPE: PRT
<213> ORGANISM: Homo sapiens

<400> SEQUENCE: 102

Gln Gln Gly Asp Thr Ser Pro Thr Thr
1               5

<210> SEQ ID NO 103
<211> LENGTH: 9
<212> TYPE: PRT
<213> ORGANISM: Homo sapiens

<400> SEQUENCE: 103

Gln Gln Gly Tyr Ser Ala Pro Thr Thr
1               5

<210> SEQ ID NO 104
<211> LENGTH: 9
<212> TYPE: PRT
<213> ORGANISM: Homo sapiens

<400> SEQUENCE: 104

Gln Gln Gly Tyr Thr Ser Pro Thr Thr
1               5

<210> SEQ ID NO 105
<211> LENGTH: 9
<212> TYPE: PRT
<213> ORGANISM: Homo sapiens

<400> SEQUENCE: 105

Gln Gln Asn Asn Tyr Tyr Pro Thr Thr
1               5

<210> SEQ ID NO 106
<211> LENGTH: 9
<212> TYPE: PRT
<213> ORGANISM: Homo sapiens

<400> SEQUENCE: 106

Gln Gln Ser Asp Ala Tyr Pro Thr Thr

<210> SEQ ID NO 107
<211> LENGTH: 9
<212> TYPE: PRT
<213> ORGANISM: Homo sapiens

<400> SEQUENCE: 107

Thr Ser Asn Tyr Pro Thr Thr Gln Gln
1               5

<210> SEQ ID NO 108
<211> LENGTH: 9
<212> TYPE: PRT
<213> ORGANISM: Homo sapiens

<400> SEQUENCE: 108

Gln Gln Ser Asn Ala Thr Pro Thr Thr
1               5

<210> SEQ ID NO 109
<211> LENGTH: 9
<212> TYPE: PRT
<213> ORGANISM: Homo sapiens

<400> SEQUENCE: 109

Gln Gln Ala Ala Gly Asn Pro Thr Thr
1               5

<210> SEQ ID NO 110
<211> LENGTH: 9
<212> TYPE: PRT
<213> ORGANISM: Homo sapiens

<400> SEQUENCE: 110

Gln Gln Gly Ser Asp Tyr Pro Thr Thr
1               5

<210> SEQ ID NO 111
<211> LENGTH: 9
<212> TYPE: PRT
<213> ORGANISM: Homo sapiens

<400> SEQUENCE: 111

Gln Gln Gly Ser Thr Ala Pro Thr Thr
1               5

<210> SEQ ID NO 112
<211> LENGTH: 9
<212> TYPE: PRT
<213> ORGANISM: Homo sapiens

<400> SEQUENCE: 112

Gln Gln Ser Thr Ala Ser Pro Ser Thr
1               5

<210> SEQ ID NO 113
<211> LENGTH: 9
<212> TYPE: PRT
<213> ORGANISM: Homo sapiens

<400> SEQUENCE: 113

Gln Gln Thr Ser Ser Tyr Pro Thr Thr
1               5

<210> SEQ ID NO 114
<211> LENGTH: 9
<212> TYPE: PRT
<213> ORGANISM: Homo sapiens

<400> SEQUENCE: 114

Gln Gln Gly Ala Gly Ser Pro Ser Thr
1               5

<210> SEQ ID NO 115
<211> LENGTH: 9
<212> TYPE: PRT
<213> ORGANISM: Homo sapiens

<400> SEQUENCE: 115

Gln Gln Arg Asn Thr Ser Pro Thr Thr
1               5

<210> SEQ ID NO 116
<211> LENGTH: 9
<212> TYPE: PRT
<213> ORGANISM: Homo sapiens

<400> SEQUENCE: 116

Gln Gln Ser Asn Thr Ser Pro Ala Thr
1               5

<210> SEQ ID NO 117
<211> LENGTH: 9
<212> TYPE: PRT
<213> ORGANISM: Homo sapiens

<400> SEQUENCE: 117

Gln Gln Ala Tyr Thr Ala Pro Thr Thr
1               5

<210> SEQ ID NO 118
<211> LENGTH: 9
<212> TYPE: PRT
<213> ORGANISM: Homo sapiens

<400> SEQUENCE: 118

Gln Gln Ala Asp Thr Tyr Pro Thr Thr
1               5

<210> SEQ ID NO 119
<211> LENGTH: 9
<212> TYPE: PRT
<213> ORGANISM: Homo sapiens

<400> SEQUENCE: 119

Gln Gln Ala Ala Asn Ser Pro Asp Thr
1               5

<210> SEQ ID NO 120
<211> LENGTH: 9
<212> TYPE: PRT
<213> ORGANISM: Homo sapiens

<400> SEQUENCE: 120

Gln Gln Thr Ser Asp Tyr Pro Asn Thr
1               5

<210> SEQ ID NO 121

```
<211> LENGTH: 9
<212> TYPE: PRT
<213> ORGANISM: Homo sapiens

<400> SEQUENCE: 121

Gln Gln Ala Ser Thr Ser Pro Thr Thr
1               5

<210> SEQ ID NO 122
<211> LENGTH: 9
<212> TYPE: PRT
<213> ORGANISM: Homo sapiens

<400> SEQUENCE: 122

Gln Gln Ala Ser Asp Tyr Pro Thr Thr
1               5

<210> SEQ ID NO 123
<211> LENGTH: 9
<212> TYPE: PRT
<213> ORGANISM: Homo sapiens

<400> SEQUENCE: 123

Gln Gln Ser Ser Ser Asn Pro Thr Thr
1               5

<210> SEQ ID NO 124
<211> LENGTH: 9
<212> TYPE: PRT
<213> ORGANISM: Homo sapiens

<400> SEQUENCE: 124

Gln Gln Gly Ser Asn Ser Pro Thr Thr
1               5

<210> SEQ ID NO 125
<211> LENGTH: 9
<212> TYPE: PRT
<213> ORGANISM: Homo sapiens

<400> SEQUENCE: 125

Gln Gln Ser Ala Thr Thr Pro Asp Thr
1               5

<210> SEQ ID NO 126
<211> LENGTH: 10
<212> TYPE: PRT
<213> ORGANISM: Homo sapiens

<400> SEQUENCE: 126

Tyr Gly Arg Lys Lys Arg Gln Arg Arg Arg
1               5                   10

<210> SEQ ID NO 127
<211> LENGTH: 17
<212> TYPE: PRT
<213> ORGANISM: Artificial
<220> FEATURE:
<223> OTHER INFORMATION: Primer LMB-3

<400> SEQUENCE: 127

Cys Ala Gly Gly Ala Ala Ala Cys Ala Gly Cys Thr Ala Thr Gly Ala
1               5                   10                  15

Cys
```

<210> SEQ ID NO 128
<211> LENGTH: 17
<212> TYPE: PRT
<213> ORGANISM: Artificial
<220> FEATURE:
<223> OTHER INFORMATION: Primer Fd-Seq

<400> SEQUENCE: 128

Gly Ala Ala Thr Thr Thr Thr Cys Thr Gly Thr Ala Thr Gly Ala Gly
1               5                   10                  15

Gly

<210> SEQ ID NO 129
<211> LENGTH: 27
<212> TYPE: DNA
<213> ORGANISM: Artificial
<220> FEATURE:
<223> OTHER INFORMATION: Primer mIFNBHindFOR

<400> SEQUENCE: 129
gctaagctta tgaacaacag gtggatt                                      27

<210> SEQ ID NO 130
<211> LENGTH: 27
<212> TYPE: DNA
<213> ORGANISM: Artificial
<220> FEATURE:
<223> OTHER INFORMATION: Primer mIFNBEcoRIREV

<400> SEQUENCE: 130
cgcgaattcg ttttggaagt ttctggt                                      27

<210> SEQ ID NO 131
<211> LENGTH: 30
<212> TYPE: DNA
<213> ORGANISM: Artificial
<220> FEATURE:
<223> OTHER INFORMATION: Primer NotI1-11Efor

<400> SEQUENCE: 131
caggcggccg caatggccga ggtgcagctg                                   30

<210> SEQ ID NO 132
<211> LENGTH: 54
<212> TYPE: DNA
<213> ORGANISM: Artificial
<220> FEATURE:
<223> OTHER INFORMATION: Primer 1-11EApaRev

<400> SEQUENCE: 132
cttgggccct caatggtggt ggtgatggtg tctagaccgt tgatttcca cctt         54

<210> SEQ ID NO 133
<211> LENGTH: 54
<212> TYPE: DNA
<213> ORGANISM: Artificial
<220> FEATURE:
<223> OTHER INFORMATION: Primer mIFN-bApaRev

<400> SEQUENCE: 133
cttgggccct caatggtggt ggtgatggtg tctagagttt tggaagtttc tggt        54

<210> SEQ ID NO 134
<211> LENGTH: 452
<212> TYPE: PRT

<213> ORGANISM: Mus musculus

<400> SEQUENCE: 134

```
Met Asn Asn Arg Trp Ile Leu His Ala Ala Phe Leu Leu Cys Phe Ser
1               5                   10                  15

Thr Thr Ala Leu Ser Ile Asn Tyr Lys Gln Leu Gln Leu Gln Glu Arg
            20                  25                  30

Thr Asn Ile Arg Lys Cys Gln Glu Leu Leu Glu Gln Leu Asn Gly Lys
        35                  40                  45

Ile Asn Leu Thr Tyr Arg Ala Asp Phe Lys Ile Pro Met Glu Met Thr
    50                  55                  60

Glu Lys Met Gln Lys Ser Tyr Thr Ala Phe Ala Ile Gln Glu Met Leu
65                  70                  75                  80

Gln Asn Val Phe Leu Val Phe Arg Asn Asn Phe Ser Ser Thr Gly Trp
                85                  90                  95

Asn Glu Thr Ile Val Val Arg Leu Leu Asp Glu Leu His Gln Gln Thr
            100                 105                 110

Val Phe Leu Lys Thr Val Leu Glu Glu Lys Gln Glu Glu Arg Leu Thr
        115                 120                 125

Trp Glu Met Ser Ser Thr Ala Leu His Leu Lys Ser Tyr Tyr Trp Arg
130                 135                 140

Val Gln Arg Tyr Leu Lys Leu Met Lys Tyr Asn Ser Tyr Ala Trp Met
145                 150                 155                 160

Val Val Arg Ala Glu Ile Phe Arg Asn Phe Leu Ile Ile Arg Arg Leu
                165                 170                 175

Thr Arg Asn Phe Gln Asn Glu Phe Gly Gly Gly Ser Pro Leu Gly
            180                 185                 190

Leu Trp Ala Gly Gly Gly Ser Ala Ala Ala Met Ala Glu Val Gln Leu
        195                 200                 205

Leu Glu Ser Gly Gly Gly Leu Val Gln Pro Gly Gly Ser Leu Arg Leu
210                 215                 220

Ser Cys Ala Ala Ser Gly Phe Thr Phe Ser Ser Tyr Ala Met Ser Trp
225                 230                 235                 240

Val Arg Gln Ala Pro Gly Lys Gly Leu Glu Trp Val Ser Ser Ile Asp
                245                 250                 255

Asp Ser Gly Ala Thr Thr Tyr Tyr Ala Asp Ser Val Lys Gly Arg Phe
            260                 265                 270

Thr Ile Ser Arg Asp Asn Ser Lys Asn Thr Leu Tyr Leu Gln Met Asn
        275                 280                 285

Ser Leu Arg Ala Glu Asp Thr Ala Val Tyr Tyr Cys Ala Lys Asn Tyr
290                 295                 300

Ser Ser Phe Asp Tyr Trp Gly Gln Gly Thr Leu Val Thr Val Ser Ser
305                 310                 315                 320

Gly Gly Gly Gly Ser Gly Gly Gly Ser Gly Gly Gly Gly Ser Thr
                325                 330                 335

Asp Ile Gln Met Thr Gln Ser Pro Ser Ser Leu Ser Ala Ser Val Gly
            340                 345                 350

Asp Arg Val Thr Ile Thr Cys Arg Ala Ser Gln Ser Ile Ser Ser Tyr
        355                 360                 365

Leu Asn Trp Tyr Gln Gln Lys Pro Gly Lys Ala Pro Lys Leu Leu Ile
370                 375                 380

Tyr Tyr Ala Ser Ser Leu Gln Ser Gly Val Pro Ser Arg Phe Ser Gly
385                 390                 395                 400
```

```
Ser Gly Ser Gly Thr Asp Phe Thr Leu Thr Ile Ser Ser Leu Gln Pro
            405                 410                 415

Glu Asp Phe Ala Thr Tyr Tyr Cys Gln Gln Ala Ala Asn Tyr Pro Thr
            420                 425                 430

Thr Phe Gly Gln Gly Thr Lys Val Glu Ile Lys Arg Asp Ile His His
            435                 440                 445

His His His His
        450

<210> SEQ ID NO 135
<211> LENGTH: 182
<212> TYPE: PRT
<213> ORGANISM: Mus musculus

<400> SEQUENCE: 135

Met Asn Asn Arg Trp Ile Leu His Ala Ala Phe Leu Leu Cys Phe Ser
1               5                   10                  15

Thr Thr Ala Leu Ser Ile Asn Tyr Lys Gln Leu Gln Leu Gln Glu Arg
            20                  25                  30

Thr Asn Ile Arg Lys Cys Gln Glu Leu Leu Glu Gln Leu Asn Gly Lys
        35                  40                  45

Ile Asn Leu Thr Tyr Arg Ala Asp Phe Lys Ile Pro Met Glu Met Thr
    50                  55                  60

Glu Lys Met Gln Lys Ser Tyr Thr Ala Phe Ala Ile Gln Glu Met Leu
65                  70                  75                  80

Gln Asn Val Phe Leu Val Phe Arg Asn Asn Phe Ser Ser Thr Gly Trp
                85                  90                  95

Asn Glu Thr Ile Val Val Arg Leu Leu Asp Glu Leu His Gln Gln Thr
            100                 105                 110

Val Phe Leu Lys Thr Val Leu Glu Glu Lys Gln Glu Arg Leu Thr
        115                 120                 125

Trp Glu Met Ser Ser Thr Ala Leu His Leu Lys Ser Tyr Tyr Trp Arg
    130                 135                 140

Val Gln Arg Tyr Leu Lys Leu Met Lys Tyr Asn Ser Tyr Ala Trp Met
145                 150                 155                 160

Val Val Arg Ala Glu Ile Phe Arg Asn Phe Leu Ile Ile Arg Arg Leu
                165                 170                 175

Thr Arg Asn Phe Gln Asn
            180

<210> SEQ ID NO 136
<211> LENGTH: 20
<212> TYPE: PRT
<213> ORGANISM: Mus musculus

<400> SEQUENCE: 136

Glu Phe Gly Gly Gly Gly Ser Pro Leu Gly Leu Trp Ala Gly Gly Gly
1               5                   10                  15

Ser Ala Ala Ala
        20

<210> SEQ ID NO 137
<211> LENGTH: 244
<212> TYPE: PRT
<213> ORGANISM: Mus musculus

<400> SEQUENCE: 137

Met Ala Glu Val Gln Leu Leu Glu Ser Gly Gly Gly Leu Val Gln Pro
```

```
                1               5                  10                 15
Gly Gly Ser Leu Arg Leu Ser Cys Ala Ala Ser Gly Phe Thr Phe Ser
                20                  25                 30

Ser Tyr Ala Met Ser Trp Val Arg Gln Ala Pro Gly Lys Gly Leu Glu
                35                  40                 45

Trp Val Ser Ser Ile Asp Asp Ser Gly Ala Thr Thr Tyr Tyr Ala Asp
            50                  55                 60

Ser Val Lys Gly Arg Phe Thr Ile Ser Arg Asp Asn Ser Lys Asn Thr
65                  70                  75                 80

Leu Tyr Leu Gln Met Asn Ser Leu Arg Ala Glu Asp Thr Ala Val Tyr
                85                  90                 95

Tyr Cys Ala Lys Asn Tyr Ser Ser Phe Asp Tyr Trp Gly Gln Gly Thr
                100                 105                110

Leu Val Thr Val Ser Ser Gly Gly Gly Ser Gly Gly Gly Ser
                115                 120                125

Gly Gly Gly Gly Ser Thr Asp Ile Gln Met Thr Gln Ser Pro Ser Ser
        130                 135                 140

Leu Ser Ala Ser Val Gly Asp Arg Val Thr Ile Thr Cys Arg Ala Ser
145                 150                 155                160

Gln Ser Ile Ser Ser Tyr Leu Asn Trp Tyr Gln Gln Lys Pro Gly Lys
                165                 170                175

Ala Pro Lys Leu Leu Ile Tyr Tyr Ala Ser Ser Leu Gln Ser Gly Val
                180                 185                190

Pro Ser Arg Phe Ser Gly Ser Gly Ser Gly Thr Asp Phe Thr Leu Thr
                195                 200                205

Ile Ser Ser Leu Gln Pro Glu Asp Phe Ala Thr Tyr Tyr Cys Gln Gln
            210                 215                220

Ala Ala Asn Tyr Pro Thr Thr Phe Gly Gln Gly Thr Lys Val Glu Ile
225                 230                 235                240

Lys Arg Asp Ile

<210> SEQ ID NO 138
<211> LENGTH: 6
<212> TYPE: PRT
<213> ORGANISM: Mus musculus

<400> SEQUENCE: 138

His His His His His His
1               5

<210> SEQ ID NO 139
<211> LENGTH: 190
<212> TYPE: PRT
<213> ORGANISM: Mus musculus

<400> SEQUENCE: 139

Met Asn Asn Arg Trp Ile Leu His Ala Ala Phe Leu Leu Cys Phe Ser
1               5                   10                 15

Thr Thr Ala Leu Ser Ile Asn Tyr Lys Gln Leu Gln Leu Gln Glu Arg
                20                  25                 30

Thr Asn Ile Arg Lys Cys Gln Glu Leu Leu Glu Gln Leu Asn Gly Lys
                35                  40                 45

Ile Asn Leu Thr Tyr Arg Ala Asp Phe Lys Ile Pro Met Glu Met Thr
            50                  55                 60

Glu Lys Met Gln Lys Ser Tyr Thr Ala Phe Ala Ile Gln Glu Met Leu
65                  70                  75                 80
```

```
Gln Asn Val Phe Leu Val Phe Arg Asn Asn Phe Ser Ser Thr Gly Trp
                85                  90                  95

Asn Glu Thr Ile Val Val Arg Leu Leu Asp Glu Leu His Gln Gln Thr
            100                 105                 110

Val Phe Leu Lys Thr Val Leu Glu Glu Lys Gln Glu Glu Arg Leu Thr
        115                 120                 125

Trp Glu Met Ser Ser Thr Ala Leu His Leu Lys Ser Tyr Tyr Trp Arg
    130                 135                 140

Val Gln Arg Tyr Leu Lys Leu Met Lys Tyr Asn Ser Tyr Ala Trp Met
145                 150                 155                 160

Val Val Arg Ala Glu Ile Phe Arg Asn Phe Leu Ile Ile Arg Arg Leu
                165                 170                 175

Thr Arg Asn Phe Gln Asn Asp Ile His His His His His
            180                 185                 190

<210> SEQ ID NO 140
<211> LENGTH: 184
<212> TYPE: PRT
<213> ORGANISM: Mus musculus

<400> SEQUENCE: 140

Met Asn Asn Arg Trp Ile Leu His Ala Ala Phe Leu Leu Cys Phe Ser
1               5                   10                  15

Thr Thr Ala Leu Ser Ile Asn Tyr Lys Gln Leu Gln Leu Gln Glu Arg
            20                  25                  30

Thr Asn Ile Arg Lys Cys Gln Glu Leu Leu Glu Gln Leu Asn Gly Lys
        35                  40                  45

Ile Asn Leu Thr Tyr Arg Ala Asp Phe Lys Ile Pro Met Glu Met Thr
    50                  55                  60

Glu Lys Met Gln Lys Ser Tyr Thr Ala Phe Ala Ile Gln Glu Met Leu
65                  70                  75                  80

Gln Asn Val Phe Leu Val Phe Arg Asn Asn Phe Ser Ser Thr Gly Trp
                85                  90                  95

Asn Glu Thr Ile Val Val Arg Leu Leu Asp Glu Leu His Gln Gln Thr
            100                 105                 110

Val Phe Leu Lys Thr Val Leu Glu Glu Lys Gln Glu Glu Arg Leu Thr
        115                 120                 125

Trp Glu Met Ser Ser Thr Ala Leu His Leu Lys Ser Tyr Tyr Trp Arg
    130                 135                 140

Val Gln Arg Tyr Leu Lys Leu Met Lys Tyr Asn Ser Tyr Ala Trp Met
145                 150                 155                 160

Val Val Arg Ala Glu Ile Phe Arg Asn Phe Leu Ile Ile Arg Arg Leu
                165                 170                 175

Thr Arg Asn Phe Gln Asn Asp Ile
            180

<210> SEQ ID NO 141
<211> LENGTH: 27
<212> TYPE: DNA
<213> ORGANISM: Artificial
<220> FEATURE:
<223> OTHER INFORMATION: Forward Primer for Mouse TNFR2-Fc

<400> SEQUENCE: 141
gctaagctta tggcgcccgc cgccctc                                        27
```

```
<210> SEQ ID NO 142
<211> LENGTH: 27
<212> TYPE: DNA
<213> ORGANISM: Artificial
<220> FEATURE:
<223> OTHER INFORMATION: Reverse primer for Mouse TNFR2-Fc

<400> SEQUENCE: 142
cttgaattct ttacccagag accggga                                      27

<210> SEQ ID NO 143
<211> LENGTH: 706
<212> TYPE: PRT
<213> ORGANISM: Mus musculus

<400> SEQUENCE: 143
```

| | | | | | | | | | | | | | | |
|---|---|---|---|---|---|---|---|---|---|---|---|---|---|---|
| Met | Ala | Pro | Ala | Ala | Leu | Trp | Val | Ala | Leu | Val | Phe | Glu | Leu | Gln |
| 1 | | | | 5 | | | | | 10 | | | | | 15 |
| Leu | | | | | | | | | | | | | | |

| | | | | | | | | | | | | | | |
|---|---|---|---|---|---|---|---|---|---|---|---|---|---|---|
| Trp | Ala | Thr | Gly | His | Thr | Val | Pro | Ala | Gln | Val | Val | Leu | Thr | Pro |
| | | | 20 | | | | | 25 | | | | | 30 | |
| Tyr | | | | | | | | | | | | | | |

| | | | | | | | | | | | | | |
|---|---|---|---|---|---|---|---|---|---|---|---|---|---|
| Lys | Pro | Glu | Pro | Gly | Tyr | Glu | Cys | Gln | Ile | Ser | Gln | Glu | Tyr |
| | 35 | | | | | 40 | | | | | 45 | | |
| Tyr | Asp | | | | | | | | | | | | |

| | | | | | | | | | | | | |
|---|---|---|---|---|---|---|---|---|---|---|---|---|
| Arg | Lys | Ala | Gln | Met | Cys | Cys | Ala | Lys | Cys | Pro | Pro | Gly |
| | 50 | | | | | 55 | | | | | 60 | |
| Gln | Tyr | Val | | | | | | | | | | |

| | | | | | | | | | | | | | | |
|---|---|---|---|---|---|---|---|---|---|---|---|---|---|---|
| Lys | His | Phe | Cys | Asn | Lys | Thr | Ser | Asp | Thr | Val | Cys | Ala | Asp | Cys |
| 65 | | | | | 70 | | | | | 75 | | | | 80 |
| Glu | | | | | | | | | | | | | | |

| | | | | | | | | | | | | | | |
|---|---|---|---|---|---|---|---|---|---|---|---|---|---|---|
| Ala | Ser | Met | Tyr | Thr | Gln | Val | Trp | Asn | Gln | Phe | Arg | Thr | Cys | Leu |
| | | | | 85 | | | | | 90 | | | | | 95 |
| Ser | | | | | | | | | | | | | | |

| | | | | | | | | | | | | |
|---|---|---|---|---|---|---|---|---|---|---|---|---|
| Cys | Ser | Ser | Cys | Thr | Thr | Asp | Gln | Val | Glu | Ile | Arg | Ala |
| | | | | 100 | | | | | 105 | | | |
| Cys | Thr | | | | | | | | | | | |
| 110 | | | | | | | | | | | | |

| | | | | | | | | | | | |
|---|---|---|---|---|---|---|---|---|---|---|---|
| Lys | Gln | Gln | Asn | Arg | Val | Cys | Ala | Cys | Glu | Ala | Gly |
| | | 115 | | | | | 120 | | | | |
| Arg | Tyr | Cys | Ala | | | | | | | | |
| 125 | | | | | | | | | | | |

| | | | | | | | | | | | |
|---|---|---|---|---|---|---|---|---|---|---|---|
| Leu | Lys | Thr | His | Ser | Gly | Ser | Cys | Arg | Gln | Cys | Met |
| | | 130 | | | | | 135 | | | | |
| Arg | Leu | Ser | Lys | | | | | | | | |
| 140 | | | | | | | | | | | |

| | | | | | | | | | | | | | | |
|---|---|---|---|---|---|---|---|---|---|---|---|---|---|---|
| Cys | Gly | Pro | Gly | Phe | Gly | Val | Ala | Ser | Ser | Arg | Ala | Pro | Asn | Gly |
| 145 | | | | | 150 | | | | | 155 | | | | 160 |
| Asn | | | | | | | | | | | | | | |

| | | | | | | | | | | | | | | |
|---|---|---|---|---|---|---|---|---|---|---|---|---|---|---|
| Val | Leu | Cys | Lys | Ala | Cys | Ala | Pro | Gly | Thr | Phe | Ser | Asp | Thr | Thr |
| | | | | 165 | | | | | 170 | | | | | 175 |
| Ser | | | | | | | | | | | | | | |

| | | | | | | | | | | | | |
|---|---|---|---|---|---|---|---|---|---|---|---|---|
| Ser | Thr | Asp | Val | Cys | Arg | Pro | His | Arg | Ile | Cys | Ser | Ile |
| | | | 180 | | | | | 185 | | | | |
| Leu | Ala | Ile | | | | | | | | | | |
| 190 | | | | | | | | | | | | |

| | | | | | | | | | | | |
|---|---|---|---|---|---|---|---|---|---|---|---|
| Pro | Gly | Asn | Ala | Ser | Thr | Asp | Ala | Val | Cys | Ala | Pro |
| | | | 195 | | | | | 200 | | | |
| Glu | Ser | Asp | Gly | | | | | | | | |
| 205 | | | | | | | | | | | |

| | | | | | | | | | | | |
|---|---|---|---|---|---|---|---|---|---|---|---|
| Ser | Pro | Pro | Leu | Lys | Glu | Cys | Pro | Pro | Cys | Ala | Ala |
| | 210 | | | | | 215 | | | | | 220 |
| Pro | Asp | Leu | Leu | | | | | | | | |

| | | | | | | | | | | | | | | |
|---|---|---|---|---|---|---|---|---|---|---|---|---|---|---|
| Gly | Gly | Pro | Ser | Val | Phe | Ile | Phe | Pro | Pro | Lys | Ile | Lys | Asp | Val |
| 225 | | | | | 230 | | | | | 235 | | | | 240 |
| Leu | | | | | | | | | | | | | | |

| | | | | | | | | | | | | | | |
|---|---|---|---|---|---|---|---|---|---|---|---|---|---|---|
| Met | Ile | Ser | Leu | Ser | Pro | Met | Val | Thr | Cys | Val | Val | Val | Asp | Val |
| | | | | 245 | | | | | 250 | | | | | 255 |
| Ser | | | | | | | | | | | | | | |

| | | | | | | | | | | | | |
|---|---|---|---|---|---|---|---|---|---|---|---|---|
| Glu | Asp | Asp | Pro | Asp | Val | Gln | Ile | Ser | Trp | Phe | Val | Asn |
| | | | 260 | | | | | 265 | | | | |
| Asn | Val | Glu | | | | | | | | | | |
| 270 | | | | | | | | | | | | |

| | | | | | | | | | | | | |
|---|---|---|---|---|---|---|---|---|---|---|---|---|
| Val | His | Thr | Ala | Gln | Thr | Gln | Thr | His | Arg | Glu | Asp | Tyr |
| | | 275 | | | | | 280 | | | | | |
| Asn | Ser | Thr | | | | | | | | | | |
| 285 | | | | | | | | | | | | |

| | | | | | | | | | | | | |
|---|---|---|---|---|---|---|---|---|---|---|---|---|
| Leu | Arg | Val | Val | Ser | Ala | Leu | Pro | Ile | Gln | His | Gln | Asp |
| | 290 | | | | | 295 | | | | | 300 | |
| Trp | Met | Ser | | | | | | | | | | |

| | | | | | | | | | | | | | | |
|---|---|---|---|---|---|---|---|---|---|---|---|---|---|---|
| Gly | Lys | Glu | Phe | Lys | Cys | Lys | Val | Asn | Asn | Arg | Ala | Leu | Pro | Ser |
| 305 | | | | | 310 | | | | | 315 | | | | 320 |
| Pro | | | | | | | | | | | | | | |

```
Ile Glu Lys Thr Ile Ser Lys Pro Arg Gly Pro Val Arg Ala Pro Gln
            325                 330                 335

Val Tyr Val Leu Pro Pro Ala Glu Glu Met Thr Lys Lys Glu Phe
        340                 345                 350

Ser Leu Thr Cys Met Ile Thr Gly Phe Leu Pro Ala Glu Ile Ala Val
        355                 360                 365

Asp Trp Thr Ser Asn Gly Arg Thr Glu Gln Asn Tyr Lys Asn Thr Ala
370                 375                 380

Thr Val Leu Asp Ser Asp Gly Ser Tyr Phe Met Tyr Ser Lys Leu Arg
385                 390                 395                 400

Val Gln Lys Ser Thr Trp Glu Arg Gly Ser Leu Phe Ala Cys Ser Val
                405                 410                 415

Val His Glu Gly Leu His Asn His Leu Thr Thr Lys Thr Ile Ser Arg
            420                 425                 430

Ser Leu Gly Lys Glu Phe Gly Gly Gly Ser Pro Leu Gly Leu Trp
        435                 440                 445

Ala Gly Gly Gly Ser Ala Ala Met Ala Glu Val Gln Leu Leu Glu
    450                 455                 460

Ser Gly Gly Gly Leu Val Gln Pro Gly Gly Ser Leu Arg Leu Ser Cys
465                 470                 475                 480

Ala Ala Ser Gly Phe Thr Phe Ser Ser Tyr Ala Met Ser Trp Val Arg
                485                 490                 495

Gln Ala Pro Gly Lys Gly Leu Glu Trp Val Ser Ser Ile Asp Asp Ser
            500                 505                 510

Gly Ala Thr Thr Tyr Tyr Ala Asp Ser Val Lys Gly Arg Phe Thr Ile
        515                 520                 525

Ser Arg Asp Asn Ser Lys Asn Thr Leu Tyr Leu Gln Met Asn Ser Leu
530                 535                 540

Arg Ala Glu Asp Thr Ala Val Tyr Tyr Cys Ala Lys Asn Tyr Ser Ser
545                 550                 555                 560

Phe Asp Tyr Trp Gly Gln Gly Thr Leu Val Thr Val Ser Ser Gly Gly
                565                 570                 575

Gly Gly Ser Gly Gly Gly Gly Ser Gly Gly Gly Gly Ser Thr Asp Ile
            580                 585                 590

Gln Met Thr Gln Ser Pro Ser Ser Leu Ser Ala Ser Val Gly Asp Arg
        595                 600                 605

Val Thr Ile Thr Cys Arg Ala Ser Gln Ser Ile Ser Ser Tyr Leu Asn
        610                 615                 620

Trp Tyr Gln Gln Lys Pro Gly Lys Ala Pro Lys Leu Leu Ile Tyr Tyr
625                 630                 635                 640

Ala Ser Ser Leu Gln Ser Gly Val Pro Ser Arg Phe Ser Gly Ser Gly
                645                 650                 655

Ser Gly Thr Asp Phe Thr Leu Thr Ile Ser Ser Leu Gln Pro Glu Asp
            660                 665                 670

Phe Ala Thr Tyr Tyr Cys Gln Gln Ala Ala Asn Tyr Pro Thr Thr Phe
        675                 680                 685

Gly Gln Gly Thr Lys Val Glu Ile Lys Arg Asp Ile His His His His
        690                 695                 700

His His
705

<210> SEQ ID NO 144
<211> LENGTH: 436
<212> TYPE: PRT
```

<213> ORGANISM: Mus musculus

<400> SEQUENCE: 144

```
Met Ala Pro Ala Ala Leu Trp Val Ala Leu Val Phe Glu Leu Gln Leu
1               5                   10                  15

Trp Ala Thr Gly His Thr Val Pro Ala Gln Val Val Leu Thr Pro Tyr
            20                  25                  30

Lys Pro Glu Pro Gly Tyr Glu Cys Gln Ile Ser Gln Glu Tyr Tyr Asp
        35                  40                  45

Arg Lys Ala Gln Met Cys Cys Ala Lys Cys Pro Pro Gly Gln Tyr Val
    50                  55                  60

Lys His Phe Cys Asn Lys Thr Ser Asp Thr Val Cys Ala Asp Cys Glu
65                  70                  75                  80

Ala Ser Met Tyr Thr Gln Val Trp Asn Gln Phe Arg Thr Cys Leu Ser
                85                  90                  95

Cys Ser Ser Ser Cys Thr Thr Asp Gln Val Glu Ile Arg Ala Cys Thr
            100                 105                 110

Lys Gln Gln Asn Arg Val Cys Ala Cys Glu Ala Gly Arg Tyr Cys Ala
        115                 120                 125

Leu Lys Thr His Ser Gly Ser Cys Arg Gln Cys Met Arg Leu Ser Lys
    130                 135                 140

Cys Gly Pro Gly Phe Gly Val Ala Ser Ser Arg Ala Pro Asn Gly Asn
145                 150                 155                 160

Val Leu Cys Lys Ala Cys Ala Pro Gly Thr Phe Ser Asp Thr Thr Ser
                165                 170                 175

Ser Thr Asp Val Cys Arg Pro His Arg Ile Cys Ser Ile Leu Ala Ile
            180                 185                 190

Pro Gly Asn Ala Ser Thr Asp Ala Val Cys Ala Pro Glu Ser Asp Gly
        195                 200                 205

Ser Pro Pro Leu Lys Glu Cys Pro Pro Cys Ala Ala Pro Asp Leu Leu
    210                 215                 220

Gly Gly Pro Ser Val Phe Ile Phe Pro Pro Lys Ile Lys Asp Val Leu
225                 230                 235                 240

Met Ile Ser Leu Ser Pro Met Val Thr Cys Val Val Asp Val Ser
                245                 250                 255

Glu Asp Asp Pro Asp Val Gln Ile Ser Trp Phe Val Asn Asn Val Glu
            260                 265                 270

Val His Thr Ala Gln Thr Gln Thr His Arg Glu Asp Tyr Asn Ser Thr
        275                 280                 285

Leu Arg Val Val Ser Ala Leu Pro Ile Gln His Gln Asp Trp Met Ser
    290                 295                 300

Gly Lys Glu Phe Lys Cys Lys Val Asn Asn Arg Ala Leu Pro Ser Pro
305                 310                 315                 320

Ile Glu Lys Thr Ile Ser Lys Pro Arg Gly Pro Val Arg Ala Pro Gln
                325                 330                 335

Val Tyr Val Leu Pro Pro Pro Ala Glu Glu Met Thr Lys Lys Glu Phe
            340                 345                 350

Ser Leu Thr Cys Met Ile Thr Gly Phe Leu Pro Ala Glu Ile Ala Val
        355                 360                 365

Asp Trp Thr Ser Asn Gly Arg Thr Glu Gln Asn Tyr Lys Asn Thr Ala
    370                 375                 380

Thr Val Leu Asp Ser Asp Gly Ser Tyr Phe Met Tyr Ser Lys Leu Arg
385                 390                 395                 400
```

-continued

```
Val Gln Lys Ser Thr Trp Glu Arg Gly Ser Leu Phe Ala Cys Ser Val
            405                 410                 415

Val His Glu Gly Leu His Asn His Leu Thr Thr Lys Thr Ile Ser Arg
            420                 425                 430

Ser Leu Gly Lys
        435

<210> SEQ ID NO 145
<211> LENGTH: 20
<212> TYPE: PRT
<213> ORGANISM: Mus musculus

<400> SEQUENCE: 145

Glu Phe Gly Gly Gly Ser Pro Leu Gly Leu Trp Ala Gly Gly
1               5                   10                  15

Ser Ala Ala
        20

<210> SEQ ID NO 146
<211> LENGTH: 244
<212> TYPE: PRT
<213> ORGANISM: Mus musculus

<400> SEQUENCE: 146

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ser Ile Asp Asp Ser Gly Ala Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asn Tyr Ser Ser Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Tyr Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Ala Ala Asn Tyr Pro Thr Thr Phe Gly Gln Gly Thr Lys Val Glu Ile
225                 230                 235                 240

Lys Arg Asp Ile
```

<210> SEQ ID NO 147
<211> LENGTH: 690
<212> TYPE: PRT
<213> ORGANISM: Mus musculus

<400> SEQUENCE: 147

```
Met Ala Pro Ala Ala Leu Trp Val Ala Leu Val Phe Glu Leu Gln Leu
1               5                   10                  15

Trp Ala Thr Gly His Thr Val Pro Ala Gln Val Val Leu Thr Pro Tyr
            20                  25                  30

Lys Pro Glu Pro Gly Tyr Glu Cys Gln Ile Ser Gln Glu Tyr Tyr Asp
        35                  40                  45

Arg Lys Ala Gln Met Cys Cys Ala Lys Cys Pro Pro Gly Gln Tyr Val
50                  55                  60

Lys His Phe Cys Asn Lys Thr Ser Asp Thr Val Cys Ala Asp Cys Glu
65                  70                  75                  80

Ala Ser Met Tyr Thr Gln Val Trp Asn Gln Phe Arg Thr Cys Leu Ser
                85                  90                  95

Cys Ser Ser Cys Thr Thr Asp Gln Val Glu Ile Arg Ala Cys Thr
            100                 105                 110

Lys Gln Gln Asn Arg Val Cys Ala Cys Glu Ala Gly Arg Tyr Cys Ala
        115                 120                 125

Leu Lys Thr His Ser Gly Ser Cys Arg Gln Cys Met Arg Leu Ser Lys
130                 135                 140

Cys Gly Pro Gly Phe Gly Val Ala Ser Ser Arg Ala Pro Asn Gly Asn
145                 150                 155                 160

Val Leu Cys Lys Ala Cys Ala Pro Gly Thr Phe Ser Asp Thr Thr Ser
                165                 170                 175

Ser Thr Asp Val Cys Arg Pro His Arg Ile Cys Ser Ile Leu Ala Ile
            180                 185                 190

Pro Gly Asn Ala Ser Thr Asp Ala Val Cys Ala Pro Glu Ser Asp Gly
        195                 200                 205

Ser Pro Pro Leu Lys Glu Cys Pro Pro Cys Ala Ala Pro Asp Leu Leu
210                 215                 220

Gly Gly Pro Ser Val Phe Ile Phe Pro Pro Lys Ile Lys Asp Val Leu
225                 230                 235                 240

Met Ile Ser Leu Ser Pro Met Val Thr Cys Val Val Asp Val Ser
                245                 250                 255

Glu Asp Asp Pro Asp Val Gln Ile Ser Trp Phe Val Asn Asn Val Glu
            260                 265                 270

Val His Thr Ala Gln Thr Gln Thr His Arg Glu Asp Tyr Asn Ser Thr
        275                 280                 285

Leu Arg Val Val Ser Ala Leu Pro Ile Gln His Gln Asp Trp Met Ser
290                 295                 300

Gly Lys Glu Phe Lys Cys Lys Val Asn Asn Arg Ala Leu Pro Ser Pro
305                 310                 315                 320

Ile Glu Lys Thr Ile Ser Lys Pro Arg Gly Pro Val Arg Ala Pro Gln
                325                 330                 335

Val Tyr Val Leu Pro Pro Pro Ala Glu Glu Met Thr Lys Lys Glu Phe
            340                 345                 350

Ser Leu Thr Cys Met Ile Thr Gly Phe Leu Pro Ala Glu Ile Ala Val
        355                 360                 365

Asp Trp Thr Ser Asn Gly Arg Thr Glu Gln Asn Tyr Lys Asn Thr Ala
370                 375                 380
```

Thr Val Leu Asp Ser Asp Gly Ser Tyr Phe Met Tyr Ser Lys Leu Arg
385                 390                 395                 400

Val Gln Lys Ser Thr Trp Glu Arg Gly Ser Leu Phe Ala Cys Ser Val
            405                 410                 415

Val His Glu Gly Leu His Asn His Leu Thr Thr Lys Thr Ile Ser Arg
            420                 425                 430

Ser Leu Gly Lys Glu Phe Gly Gly Gly Ser Pro Leu Gly Leu Trp
        435                 440                 445

Ala Gly Gly Gly Ser Ala Ala Met Ala Val Gln Leu Leu Glu
    450                 455                 460

Ser Gly Gly Gly Leu Val Gln Pro Gly Gly Ser Leu Arg Leu Ser Cys
465                 470                 475                 480

Ala Ala Ser Gly Phe Thr Phe Ser Ser Tyr Ala Met Ser Trp Val Arg
                485                 490                 495

Gln Ala Pro Gly Lys Gly Leu Glu Trp Val Ser Thr Ile Ser Tyr Ala
                500                 505                 510

Gly Ala Ser Thr Ala Tyr Ala Asp Ser Val Lys Gly Arg Phe Thr Ile
            515                 520                 525

Ser Arg Asp Asn Ser Lys Asn Thr Leu Tyr Leu Gln Met Asn Ser Leu
530                 535                 540

Arg Ala Glu Asp Thr Ala Val Tyr Tyr Cys Ala Lys Thr Ser Thr Ser
545                 550                 555                 560

Phe Asp Tyr Trp Gly Gln Gly Thr Leu Val Thr Val Ser Thr Asp Ile
                565                 570                 575

Gln Met Thr Gln Ser Pro Ser Ser Leu Ser Ala Ser Val Gly Asp Arg
                580                 585                 590

Val Thr Ile Thr Cys Arg Ala Ser Gln Ser Ile Ser Ser Tyr Leu Asn
            595                 600                 605

Trp Tyr Gln Gln Lys Pro Gly Lys Ala Pro Lys Leu Leu Ile Tyr Asn
            610                 615                 620

Ala Ser Tyr Leu Gln Ser Gly Val Pro Ser Arg Phe Ser Gly Ser Gly
625                 630                 635                 640

Ser Gly Thr Asp Phe Thr Leu Thr Ile Ser Ser Leu Gln Pro Glu Asp
                645                 650                 655

Phe Ala Thr Tyr Tyr Cys Gln Gln Ala Tyr Ala Gly Pro Tyr Thr Phe
                660                 665                 670

Gly Gln Gly Thr Lys Val Glu Ile Lys Arg Asp Ile His His His His
            675                 680                 685

His His
    690

<210> SEQ ID NO 148
<211> LENGTH: 436
<212> TYPE: PRT
<213> ORGANISM: Mus musculus

<400> SEQUENCE: 148

Met Ala Pro Ala Ala Leu Trp Val Ala Leu Val Phe Glu Leu Gln Leu
1               5                   10                  15

Trp Ala Thr Gly His Thr Val Pro Ala Gln Val Val Leu Thr Pro Tyr
            20                  25                  30

Lys Pro Glu Pro Gly Tyr Glu Cys Gln Ile Ser Gln Glu Tyr Tyr Asp
        35                  40                  45

Arg Lys Ala Gln Met Cys Cys Ala Lys Cys Pro Pro Gly Gln Tyr Val
    50                  55                  60

Lys His Phe Cys Asn Lys Thr Ser Asp Thr Val Cys Ala Asp Cys Glu
65                  70                  75                  80

Ala Ser Met Tyr Thr Gln Val Trp Asn Gln Phe Arg Thr Cys Leu Ser
                85                  90                  95

Cys Ser Ser Cys Thr Thr Asp Gln Val Glu Ile Arg Ala Cys Thr
            100                 105                 110

Lys Gln Gln Asn Arg Val Cys Ala Cys Glu Ala Gly Arg Tyr Cys Ala
        115                 120                 125

Leu Lys Thr His Ser Gly Ser Cys Arg Gln Cys Met Arg Leu Ser Lys
    130                 135                 140

Cys Gly Pro Gly Phe Gly Val Ala Ser Ser Arg Ala Pro Asn Gly Asn
145                 150                 155                 160

Val Leu Cys Lys Ala Cys Ala Pro Gly Thr Phe Ser Asp Thr Thr Ser
                165                 170                 175

Ser Thr Asp Val Cys Arg Pro His Arg Ile Cys Ser Ile Leu Ala Ile
            180                 185                 190

Pro Gly Asn Ala Ser Thr Asp Ala Val Cys Ala Pro Glu Ser Asp Gly
        195                 200                 205

Ser Pro Pro Leu Lys Glu Cys Pro Pro Cys Ala Ala Pro Asp Leu Leu
210                 215                 220

Gly Gly Pro Ser Val Phe Ile Phe Pro Pro Lys Ile Lys Asp Val Leu
225                 230                 235                 240

Met Ile Ser Leu Ser Pro Met Val Thr Cys Val Val Asp Val Ser
                245                 250                 255

Glu Asp Asp Pro Asp Val Gln Ile Ser Trp Phe Val Asn Asn Val Glu
            260                 265                 270

Val His Thr Ala Gln Thr Gln Thr His Arg Glu Asp Tyr Asn Ser Thr
    275                 280                 285

Leu Arg Val Val Ser Ala Leu Pro Ile Gln His Gln Asp Trp Met Ser
290                 295                 300

Gly Lys Glu Phe Lys Cys Lys Val Asn Asn Arg Ala Leu Pro Ser Pro
305                 310                 315                 320

Ile Glu Lys Thr Ile Ser Lys Pro Arg Gly Pro Val Arg Ala Pro Gln
                325                 330                 335

Val Tyr Val Leu Pro Pro Pro Ala Glu Glu Met Thr Lys Lys Glu Phe
            340                 345                 350

Ser Leu Thr Cys Met Ile Thr Gly Phe Leu Pro Ala Glu Ile Ala Val
        355                 360                 365

Asp Trp Thr Ser Asn Gly Arg Thr Glu Gln Asn Tyr Lys Asn Thr Ala
    370                 375                 380

Thr Val Leu Asp Ser Asp Gly Ser Tyr Phe Met Tyr Ser Lys Leu Arg
385                 390                 395                 400

Val Gln Lys Ser Thr Trp Glu Arg Gly Ser Leu Phe Ala Cys Ser Val
                405                 410                 415

Val His Glu Gly Leu His Asn His Leu Thr Thr Lys Thr Ile Ser Arg
            420                 425                 430

Ser Leu Gly Lys
        435

<210> SEQ ID NO 149
<211> LENGTH: 20
<212> TYPE: PRT
<213> ORGANISM: Mus musculus

```
<400> SEQUENCE: 149

Glu Phe Gly Gly Gly Gly Ser Pro Leu Gly Leu Trp Ala Gly Gly
1               5                   10                  15

Ser Ala Ala Ala
            20

<210> SEQ ID NO 150
<211> LENGTH: 228
<212> TYPE: PRT
<213> ORGANISM: Mus musculus

<400> SEQUENCE: 150

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Thr Ile Ser Tyr Ala Gly Ala Ser Thr Ala Tyr Ala Asp
50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Thr Ser Thr Ser Phe Asp Tyr Trp Gly Gln Gly Thr
            100                 105                 110

Leu Val Thr Val Ser Thr Asp Ile Gln Met Thr Gln Ser Pro Ser Ser
        115                 120                 125

Leu Ser Ala Ser Val Gly Asp Arg Val Thr Ile Thr Cys Arg Ala Ser
130                 135                 140

Gln Ser Ile Ser Ser Tyr Leu Asn Trp Tyr Gln Gln Lys Pro Gly Lys
145                 150                 155                 160

Ala Pro Lys Leu Leu Ile Tyr Asn Ala Ser Tyr Leu Gln Ser Gly Val
                165                 170                 175

Pro Ser Arg Phe Ser Gly Ser Gly Ser Gly Thr Asp Phe Thr Leu Thr
            180                 185                 190

Ile Ser Ser Leu Gln Pro Glu Asp Phe Ala Thr Tyr Tyr Cys Gln Gln
        195                 200                 205

Ala Tyr Ala Gly Pro Tyr Thr Phe Gly Gln Gly Thr Lys Val Glu Ile
    210                 215                 220

Lys Arg Asp Ile
225

<210> SEQ ID NO 151
<211> LENGTH: 8
<212> TYPE: PRT
<213> ORGANISM: Homo sapiens

<400> SEQUENCE: 151

Ala Pro Gln Gly Ile Ala Gly Gln
1               5

<210> SEQ ID NO 152
<211> LENGTH: 8
<212> TYPE: PRT
<213> ORGANISM: Homo sapiens

<400> SEQUENCE: 152
```

Gly Pro Gln Gly Leu Leu Gly Ala
1               5

<210> SEQ ID NO 153
<211> LENGTH: 8
<212> TYPE: PRT
<213> ORGANISM: Homo sapiens

<400> SEQUENCE: 153

Gly Pro Gln Gly Leu Ala Gly Gln
1               5

<210> SEQ ID NO 154
<211> LENGTH: 8
<212> TYPE: PRT
<213> ORGANISM: Homo sapiens

<400> SEQUENCE: 154

Gly Pro Leu Gly Ile Ala Gly Ile
1               5

<210> SEQ ID NO 155
<211> LENGTH: 8
<212> TYPE: PRT
<213> ORGANISM: Homo sapiens

<400> SEQUENCE: 155

Gly Pro Glu Gly Leu Arg Val Gly
1               5

<210> SEQ ID NO 156
<211> LENGTH: 8
<212> TYPE: PRT
<213> ORGANISM: Rattus sp.
<220> FEATURE:
<221> NAME/KEY: MOD_RES
<222> LOCATION: (8)..(8)
<223> OTHER INFORMATION: Glutamate

<400> SEQUENCE: 156

Ala Ala Tyr His Leu Val Ser Xaa
1               5

<210> SEQ ID NO 157
<211> LENGTH: 8
<212> TYPE: PRT
<213> ORGANISM: Rattus sp.

<400> SEQUENCE: 157

Met Asp Ala Phe Leu Glu Ser Ser
1               5

<210> SEQ ID NO 158
<211> LENGTH: 8
<212> TYPE: PRT
<213> ORGANISM: Rattus sp.

<400> SEQUENCE: 158

Glu Pro Gln Ala Leu Ala Met Ser
1               5

<210> SEQ ID NO 159
<211> LENGTH: 8
<212> TYPE: PRT
<213> ORGANISM: Rattus sp.

<400> SEQUENCE: 159

Gln Ala Leu Ala Met Ser Ala Ile
1               5

<210> SEQ ID NO 160
<211> LENGTH: 8
<212> TYPE: PRT
<213> ORGANISM: Gallus sp.

<400> SEQUENCE: 160

Pro Ser Tyr Phe Leu Asn Ala Gly
1               5

<210> SEQ ID NO 161
<211> LENGTH: 8
<212> TYPE: PRT
<213> ORGANISM: Homo sapiens

<400> SEQUENCE: 161

Tyr Glu Ala Gly Leu Gly Val Val
1               5

<210> SEQ ID NO 162
<211> LENGTH: 8
<212> TYPE: PRT
<213> ORGANISM: Homo sapiens

<400> SEQUENCE: 162

Ala Gly Leu Gly Val Val Glu Arg
1               5

<210> SEQ ID NO 163
<211> LENGTH: 8
<212> TYPE: PRT
<213> ORGANISM: Homo sapiens

<400> SEQUENCE: 163

Ala Gly Leu Gly Ile Ser Ser Thr
1               5

<210> SEQ ID NO 164
<211> LENGTH: 8
<212> TYPE: PRT
<213> ORGANISM: Homo sapiens

<400> SEQUENCE: 164

Gly Ala Met Phe Leu Glu Ala Ile
1               5

<210> SEQ ID NO 165
<211> LENGTH: 8
<212> TYPE: PRT
<213> ORGANISM: Homo sapiens

<400> SEQUENCE: 165

Ile Pro Glu Asn Phe Phe Gly Val
1               5

<210> SEQ ID NO 166
<211> LENGTH: 8
<212> TYPE: PRT
<213> ORGANISM: Homo sapiens

<400> SEQUENCE: 166

Thr Glu Gly Glu Ala Arg Gly Ser
1               5

<210> SEQ ID NO 167
<211> LENGTH: 8
<212> TYPE: PRT
<213> ORGANISM: Homo sapiens

<400> SEQUENCE: 167

Arg Ala Ile His Ile Gln Ala Glu
1               5

<210> SEQ ID NO 168
<211> LENGTH: 8
<212> TYPE: PRT
<213> ORGANISM: Homo sapiens

<400> SEQUENCE: 168

Leu Arg Ala Tyr Leu Leu Pro Ala
1               5

<210> SEQ ID NO 169
<211> LENGTH: 8
<212> TYPE: PRT
<213> ORGANISM: Cavia porcellus
<220> FEATURE:
<221> NAME/KEY: MOD_RES
<222> LOCATION: (3)..(3)
<223> OTHER INFORMATION: Hydroxyproline Hyp
<220> FEATURE:
<221> NAME/KEY: MOD_RES
<222> LOCATION: (6)..(6)
<223> OTHER INFORMATION: Glutamate or Glutamine Glx

<400> SEQUENCE: 169

Gly Ala Xaa Gly Leu Xaa Gly His
1               5

<210> SEQ ID NO 170
<211> LENGTH: 8
<212> TYPE: PRT
<213> ORGANISM: Rattus sp.

<400> SEQUENCE: 170

Gly Pro Gln Gly Val Arg Gly Glu
1               5

<210> SEQ ID NO 171
<211> LENGTH: 8
<212> TYPE: PRT
<213> ORGANISM: Rattus sp.

<400> SEQUENCE: 171

Gly Pro Ala Gly Val Gln Gly Pro
1               5

<210> SEQ ID NO 172
<211> LENGTH: 8
<212> TYPE: PRT
<213> ORGANISM: Rattus sp.
<220> FEATURE:
<221> NAME/KEY: MOD_RES
<222> LOCATION: (6)..(6)
<223> OTHER INFORMATION: Hydroxyproline Hyp

<400> SEQUENCE: 172

```
Gly Pro Ser Gly Leu Xaa Gly Pro
1               5

<210> SEQ ID NO 173
<211> LENGTH: 8
<212> TYPE: PRT
<213> ORGANISM: Rattus sp.

<400> SEQUENCE: 173

Gly Pro Ala Gly Glu Arg Gly Ser
1               5

<210> SEQ ID NO 174
<211> LENGTH: 8
<212> TYPE: PRT
<213> ORGANISM: Rattus sp.

<400> SEQUENCE: 174

Gly Ala Lys Gly Leu Thr Gly Ser
1               5

<210> SEQ ID NO 175
<211> LENGTH: 8
<212> TYPE: PRT
<213> ORGANISM: Rattus sp.

<400> SEQUENCE: 175

Gly Pro Ala Gly Gln Asp Gly Pro
1               5

<210> SEQ ID NO 176
<211> LENGTH: 8
<212> TYPE: PRT
<213> ORGANISM: Rattus sp.

<400> SEQUENCE: 176

Gly Pro Ala Gly Phe Ala Gly Pro
1               5

<210> SEQ ID NO 177
<211> LENGTH: 8
<212> TYPE: PRT
<213> ORGANISM: Rattus sp.

<400> SEQUENCE: 177

Gly Pro Ile Gly Asn Val Gly Ala
1               5

<210> SEQ ID NO 178
<211> LENGTH: 8
<212> TYPE: PRT
<213> ORGANISM: Rattus sp.
<220> FEATURE:
<221> NAME/KEY: MOD_RES
<222> LOCATION: (3)..(3)
<223> OTHER INFORMATION: Hydroxylysine Hyl

<400> SEQUENCE: 178

Gly Pro Xaa Gly Ser Arg Gly Ala
1               5

<210> SEQ ID NO 179
<211> LENGTH: 8
<212> TYPE: PRT
<213> ORGANISM: Bos sp.
```

<400> SEQUENCE: 179

Gly Pro Gln Gly Ile Ala Gly Gln
1               5

<210> SEQ ID NO 180
<211> LENGTH: 8
<212> TYPE: PRT
<213> ORGANISM: Bos sp.

<400> SEQUENCE: 180

Gly Pro Gly Gly Leu Leu Gly Ala
1               5

<210> SEQ ID NO 181
<211> LENGTH: 8
<212> TYPE: PRT
<213> ORGANISM: Homo sapiens

<400> SEQUENCE: 181

Ile Pro Glu Asn Phe Phe Gly Val
1               5

<210> SEQ ID NO 182
<211> LENGTH: 8
<212> TYPE: PRT
<213> ORGANISM: Homo sapiens

<400> SEQUENCE: 182

Pro Pro Gly Ala Tyr His Gly Ala
1               5

<210> SEQ ID NO 183
<211> LENGTH: 8
<212> TYPE: PRT
<213> ORGANISM: Homo sapiens

<400> SEQUENCE: 183

Arg Ala Ile His Ile Gln Ala Glu
1               5

<210> SEQ ID NO 184
<211> LENGTH: 8
<212> TYPE: PRT
<213> ORGANISM: Homo sapiens

<400> SEQUENCE: 184

Gly Pro His Leu Leu Val Glu Ala
1               5

<210> SEQ ID NO 185
<211> LENGTH: 8
<212> TYPE: PRT
<213> ORGANISM: Homo sapiens

<400> SEQUENCE: 185

Leu Arg Ala Tyr Leu Leu Pro Ala
1               5

<210> SEQ ID NO 186
<211> LENGTH: 8
<212> TYPE: PRT
<213> ORGANISM: Homo sapiens

<400> SEQUENCE: 186

Gly Pro Glu Gly Leu Arg Val Gly
1               5

<210> SEQ ID NO 187
<211> LENGTH: 8
<212> TYPE: PRT
<213> ORGANISM: Homo sapiens

<400> SEQUENCE: 187

Arg Val Gly Phe Tyr Glu Ser Asp
1               5

<210> SEQ ID NO 188
<211> LENGTH: 8
<212> TYPE: PRT
<213> ORGANISM: Homo sapiens

<400> SEQUENCE: 188

Leu Leu Ser Ala Leu Val Glu Thr
1               5

<210> SEQ ID NO 189
<211> LENGTH: 8
<212> TYPE: PRT
<213> ORGANISM: Homo sapiens

<400> SEQUENCE: 189

Glu Ala Ile Pro Met Ser Ile Pro
1               5

<210> SEQ ID NO 190
<211> LENGTH: 8
<212> TYPE: PRT
<213> ORGANISM: Homo sapiens

<400> SEQUENCE: 190

Ile Ala Gly Arg Ser Leu Asn Pro
1               5

<210> SEQ ID NO 191
<211> LENGTH: 8
<212> TYPE: PRT
<213> ORGANISM: Gallus sp.

<400> SEQUENCE: 191

Leu Asn Ala Gly Phe Thr Ala Ser
1               5

<210> SEQ ID NO 192
<211> LENGTH: 8
<212> TYPE: PRT
<213> ORGANISM: Homo sapiens

<400> SEQUENCE: 192

Ile Pro Glu Asn Phe Phe Gly Val
1               5

<210> SEQ ID NO 193
<211> LENGTH: 8
<212> TYPE: PRT
<213> ORGANISM: Homo sapiens

<400> SEQUENCE: 193

Lys Pro Gln Gln Phe Phe Gly Leu
1               5

```
<210> SEQ ID NO 194
<211> LENGTH: 8
<212> TYPE: PRT
<213> ORGANISM: Homo sapiens

<400> SEQUENCE: 194

Asp Val Ala Gln Phe Val Leu Thr
1               5

<210> SEQ ID NO 195
<211> LENGTH: 8
<212> TYPE: PRT
<213> ORGANISM: Homo sapiens

<400> SEQUENCE: 195

Asp Thr Leu Glu Val Met Arg Lys
1               5

<210> SEQ ID NO 196
<211> LENGTH: 8
<212> TYPE: PRT
<213> ORGANISM: Homo sapiens

<400> SEQUENCE: 196

Asp Val Gly His Phe Arg Thr Phe
1               5

<210> SEQ ID NO 197
<211> LENGTH: 8
<212> TYPE: PRT
<213> ORGANISM: Homo sapiens

<400> SEQUENCE: 197

Asp Ser Gly Gly Phe Met Leu Thr
1               5

<210> SEQ ID NO 198
<211> LENGTH: 8
<212> TYPE: PRT
<213> ORGANISM: Homo sapiens

<400> SEQUENCE: 198

Arg Val Ala Glu Met Arg Gly Glu
1               5

<210> SEQ ID NO 199
<211> LENGTH: 8
<212> TYPE: PRT
<213> ORGANISM: Homo sapiens

<400> SEQUENCE: 199

Asp Leu Gly Arg Phe Gln Thr Phe
1               5

<210> SEQ ID NO 200
<211> LENGTH: 8
<212> TYPE: PRT
<213> ORGANISM: Homo sapiens

<400> SEQUENCE: 200

Pro Phe Ser Pro Leu Val Ala Thr
1               5
```

<210> SEQ ID NO 201
<211> LENGTH: 8
<212> TYPE: PRT
<213> ORGANISM: Homo sapiens

<400> SEQUENCE: 201

Leu Arg Ala Tyr Leu Leu Pro Ala
1               5

<210> SEQ ID NO 202
<211> LENGTH: 8
<212> TYPE: PRT
<213> ORGANISM: Homo sapiens

<400> SEQUENCE: 202

Ala Pro Gly Asn Ala Ser Glu Ser
1               5

<210> SEQ ID NO 203
<211> LENGTH: 8
<212> TYPE: PRT
<213> ORGANISM: Homo sapiens

<400> SEQUENCE: 203

Phe Ser Ser Glu Ser Lys Arg Glu
1               5

<210> SEQ ID NO 204
<211> LENGTH: 8
<212> TYPE: PRT
<213> ORGANISM: Bos sp.

<400> SEQUENCE: 204

Ala Gly Gly Ala Gln Met Gly Val
1               5

<210> SEQ ID NO 205
<211> LENGTH: 8
<212> TYPE: PRT
<213> ORGANISM: Bos sp.

<400> SEQUENCE: 205

Gln Met Gly Val Met Gln Gly Pro
1               5

<210> SEQ ID NO 206
<211> LENGTH: 8
<212> TYPE: PRT
<213> ORGANISM: Bos sp.

<400> SEQUENCE: 206

Met Ala Ala Ser Leu Lys Arg Pro
1               5

<210> SEQ ID NO 207
<211> LENGTH: 4
<212> TYPE: PRT
<213> ORGANISM: Bos sp.

<400> SEQUENCE: 207

Ala Lys Arg Glu
1

<210> SEQ ID NO 208
<211> LENGTH: 4

```
<212> TYPE: PRT
<213> ORGANISM: Bos sp.

<400> SEQUENCE: 208

Leu Arg Lys Pro
1

<210> SEQ ID NO 209
<211> LENGTH: 8
<212> TYPE: PRT
<213> ORGANISM: Bos sp.

<400> SEQUENCE: 209

Gln Ala Gln Ala Ile Leu Gln Gln
1               5

<210> SEQ ID NO 210
<211> LENGTH: 8
<212> TYPE: PRT
<213> ORGANISM: Homo sapiens

<400> SEQUENCE: 210

Arg Ala Ile His Ile Gln Ala Glu
1               5

<210> SEQ ID NO 211
<211> LENGTH: 8
<212> TYPE: PRT
<213> ORGANISM: Bos sp.

<400> SEQUENCE: 211

Leu Val Glu Ala Leu Tyr Leu Val
1               5

<210> SEQ ID NO 212
<211> LENGTH: 8
<212> TYPE: PRT
<213> ORGANISM: Bos sp.

<400> SEQUENCE: 212

Glu Ala Leu Tyr Leu Val Cys Gly
1               5

<210> SEQ ID NO 213
<211> LENGTH: 8
<212> TYPE: PRT
<213> ORGANISM: Homo sapiens

<400> SEQUENCE: 213

Ile Pro Glu Asn Phe Phe Gly Val
1               5

<210> SEQ ID NO 214
<211> LENGTH: 8
<212> TYPE: PRT
<213> ORGANISM: Homo sapiens

<400> SEQUENCE: 214

Gly Pro His Leu Leu Val Glu Ala
1               5

<210> SEQ ID NO 215
<211> LENGTH: 8
<212> TYPE: PRT
<213> ORGANISM: Homo sapiens
```

<400> SEQUENCE: 215

Pro Pro Glu Glu Leu Lys Phe Gln
1               5

<210> SEQ ID NO 216
<211> LENGTH: 8
<212> TYPE: PRT
<213> ORGANISM: Homo sapiens

<400> SEQUENCE: 216

Gly Pro Pro Gly Val Val Gly Pro
1               5

<210> SEQ ID NO 217
<211> LENGTH: 8
<212> TYPE: PRT
<213> ORGANISM: Homo sapiens

<400> SEQUENCE: 217

Gly Pro Pro Gly Leu Arg Gly Glu
1               5

<210> SEQ ID NO 218
<211> LENGTH: 8
<212> TYPE: PRT
<213> ORGANISM: Homo sapiens

<400> SEQUENCE: 218

Gly Pro Gly Gly Val Val Gly Pro
1               5

<210> SEQ ID NO 219
<211> LENGTH: 8
<212> TYPE: PRT
<213> ORGANISM: Homo sapiens

<400> SEQUENCE: 219

Ile Pro Glu Asn Phe Phe Gly Val
1               5

<210> SEQ ID NO 220
<211> LENGTH: 8
<212> TYPE: PRT
<213> ORGANISM: Homo sapiens

<400> SEQUENCE: 220

Pro Pro Gly Ala Tyr His Gly Ala
1               5

<210> SEQ ID NO 221
<211> LENGTH: 8
<212> TYPE: PRT
<213> ORGANISM: Homo sapiens

<400> SEQUENCE: 221

Arg Ala Ile His Ile Gln Ala Glu
1               5

<210> SEQ ID NO 222
<211> LENGTH: 8
<212> TYPE: PRT
<213> ORGANISM: Homo sapiens

<400> SEQUENCE: 222

```
Arg Ala Ile His Ile Gln Ala Glu
1               5

<210> SEQ ID NO 223
<211> LENGTH: 8
<212> TYPE: PRT
<213> ORGANISM: Homo sapiens

<400> SEQUENCE: 223

Gly Pro His Leu Leu Val Glu Ala
1               5
```